(12) United States Patent
Samsoondar

(10) Patent No.: US 6,689,612 B2
(45) Date of Patent: Feb. 10, 2004

(54) INDICATOR OF HEMOLYSIS

(75) Inventor: James Samsoondar, Cambridge (CA)

(73) Assignee: Spectromedical Inc., Cambridge (CA)

( * ) Notice: Subject to any disclaimer, the term of this patent is extended or adjusted under 35 U.S.C. 154(b) by 50 days.

(21) Appl. No.: 10/137,379

(22) Filed: May 3, 2002

(65) Prior Publication Data

US 2003/0027341 A1 Feb. 6, 2003

Related U.S. Application Data

(62) Division of application No. 10/023,869, filed on Dec. 21, 2001.

(51) Int. Cl.⁷ .............................................. G01N 31/00
(52) U.S. Cl. .............................. 436/8; 436/66; 436/69; 702/19
(58) Field of Search ................................ 436/8, 11, 12, 436/16, 19, 66, 69; 702/19

(56) References Cited

U.S. PATENT DOCUMENTS

| | | | |
|---|---|---|---|
| 4,001,142 A | 1/1977 | Turner | 252/408 |
| 4,069,016 A | 1/1978 | Wu | 23/230 B |
| 4,116,336 A | 9/1978 | Sorensen et al. | 206/524.8 |
| 4,297,143 A | 10/1981 | Kleinschmit et al. | 501/103 |
| 4,603,044 A | 7/1986 | Geho et al. | 424/9 |
| 4,772,561 A | 9/1988 | Genshaw | 436/169 |
| 5,134,284 A | 7/1992 | Volgyesi | 250/252.1 |
| 5,278,073 A | 1/1994 | Grandjean | 436/12 |
| 5,310,679 A | 5/1994 | Artiss et al. | 436/18 |
| 5,447,838 A | 9/1995 | Meiklejohn et al. | 435/5 |
| 5,846,492 A | 12/1998 | Jacobs et al. | 422/67 |
| 6,064,474 A * | 5/2000 | Lee et al. | 356/39 |
| 6,268,910 B1 | 7/2001 | Samsoondar et al. | 356/39 |
| 6,353,471 B1 * | 3/2002 | Samsoondar et al. | 356/40 |
| 6,372,503 B1 * | 4/2002 | Samsoondar | 436/8 |
| 6,470,279 B1 * | 10/2002 | Samsoondar | 702/28 |
| 6,512,937 B2 * | 1/2003 | Blank et al. | 600/322 |
| 6,611,777 B2 * | 8/2003 | Samsoondar | 702/104 |
| 6,615,151 B1 * | 9/2003 | Scecina et al. | 702/85 |
| 2002/0167667 A1 * | 11/2002 | Samsoondar | 356/436 |
| 2003/0068822 A1 | 4/2003 | Jacobs et al. | 436/15 |
| 2003/0078746 A1 * | 4/2003 | Samsoondar | 702/66 |
| 2003/0093230 A1 * | 5/2003 | Samsoondar | 702/28 |
| 2003/0129754 A1 * | 7/2003 | Samsoondar | 436/8 |
| 2003/0138960 A1 * | 7/2003 | Samsoondar | 436/66 |
| 2003/0157719 A1 * | 8/2003 | Samsoondar | 436/8 |
| 2003/0158685 A1 * | 8/2003 | Samsoondar | 702/104 |

FOREIGN PATENT DOCUMENTS

| | | |
|---|---|---|
| EP | 0 132 399 A1 | 1/1985 |
| WO | WO 87/06343 | 10/1987 |
| WO | WO 97/47972 | 12/1997 |
| WO | WO 98/38961 | 9/1998 |
| WO | WO 98/39634 | 9/1998 |

OTHER PUBLICATIONS

Ozdemir, et al., "Hybrid Calibration Models: An Alternative to Calibration Transfer" *Applied Spectroscopy*, vol. 52, No. 4 (1998) pp. 599–603.

Bouveresse, et al., "Calibration transfer across near–infrared spectrometric instruments using Shenk's algorithm: effects of different standarisation samples" *Analytica Chimica Acta*, vol. 297 (1994) pp. 405–416.

Bank, et al., "Transfer of Near–Infrared Multivariate Calibration without Standards" *Analytical Chemistry*, vol. 68, No. 17 (1996) pp. 2987–2995.

Blanco, et al., "Wavelength Calibration Transfer between Diode Array UV–Visible Spectrophotometers" *Applied Spectroscopy*, vol. 49, No. 5 (1995) pp. 593–597.

Wang, et al., "Multivariate Instrument Standarization" *Analytical Chemistry*, vol. 63, No. 23 (1991) pp. 2750–2756.

Gemperline, et al., "Appearance of Discontinuities in Spectra Transformed by the Piecewise Direct Instrument Standarization Procedure" *Analytical Chemistry*, vol. 68, No. 17 (1996) pp. 2913–2915.

Tietz Textbook of Clinical Chemistry, 2$^{nd}$ Edition, "Measurement of Hemoglobin Concentration in Whole Blood," pp. 2020–2025, 2069, 1994.

M. Harboe, "A Method For Determination Of Hemoglobin In Plasma By Near–Ultraviolet Spectrophotometry," Scandinav. J. Clin. & Lab. Investigation 11:66–70, 1959.

\* cited by examiner

*Primary Examiner*—Maureen M. Wallenhorst
(74) *Attorney, Agent, or Firm*—Katten Muchin Zavis Rosenman

(57) ABSTRACT

The invention provides a method of monitoring calibration of a spectrophotometric apparatus including one or more calibration algorithms for one or more analytes. This method includes measuring absorbance of a quality control material with the apparatus to obtain a measurement, where the quality control material exhibits an absorbance spectra having a negative slope for a continuous spectral segment from about 5 nm to about 200 nm in length, and where the spectral segment includes a principal calibration wavelength for the one or more analytes. The method then involves calculating one or more concentration values from the measurement using the one or more calibration algorithms, followed by comparing the one or more concentration values with an assigned value given to the quality control material for each of the one or more analytes, and determining if there is a violation of a pre-established quality control rule. In this way one or more calibration algorithms of the apparatus may be monitored.

12 Claims, 39 Drawing Sheets

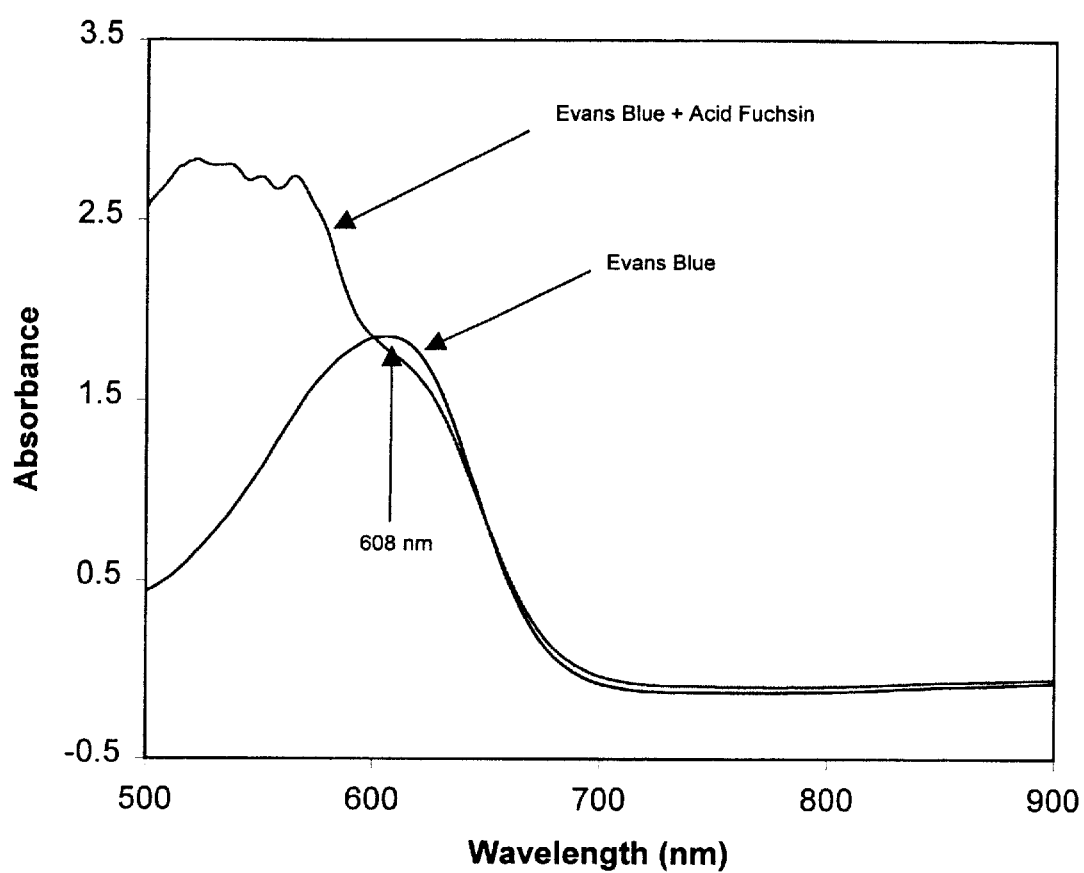

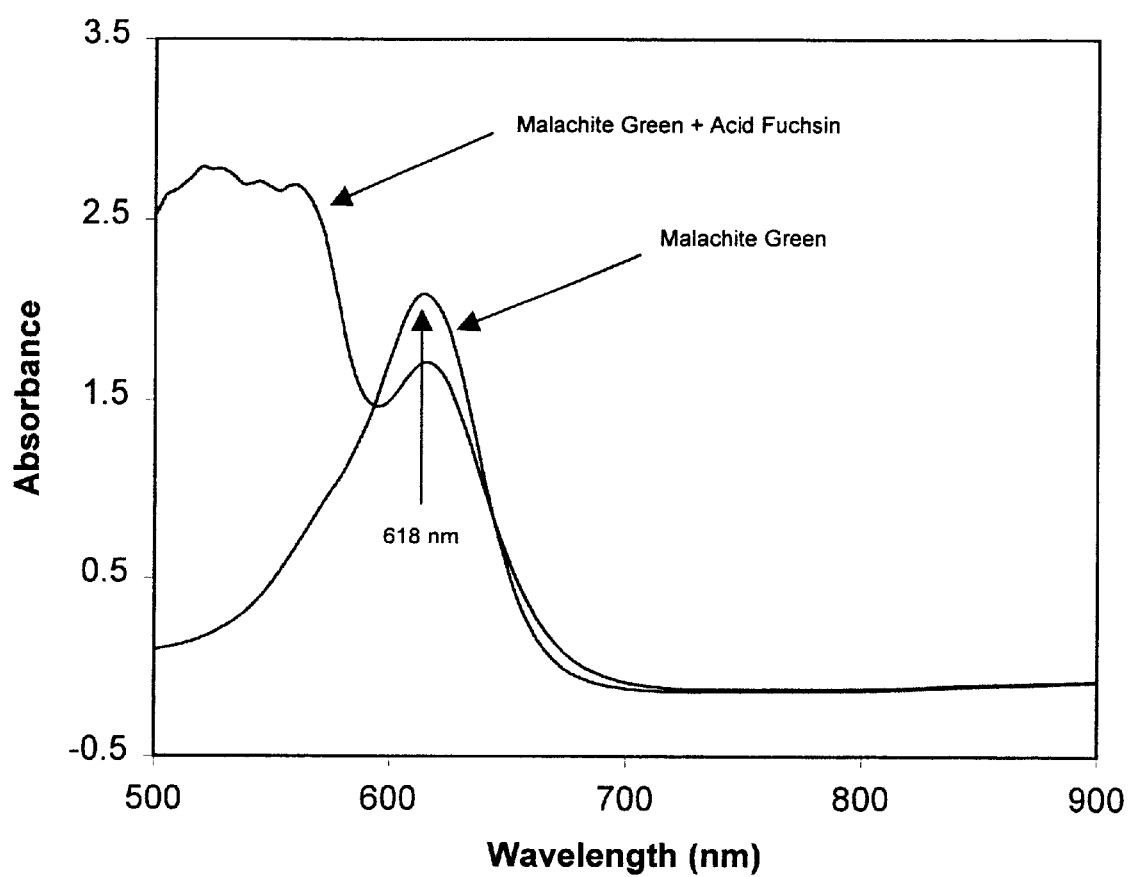

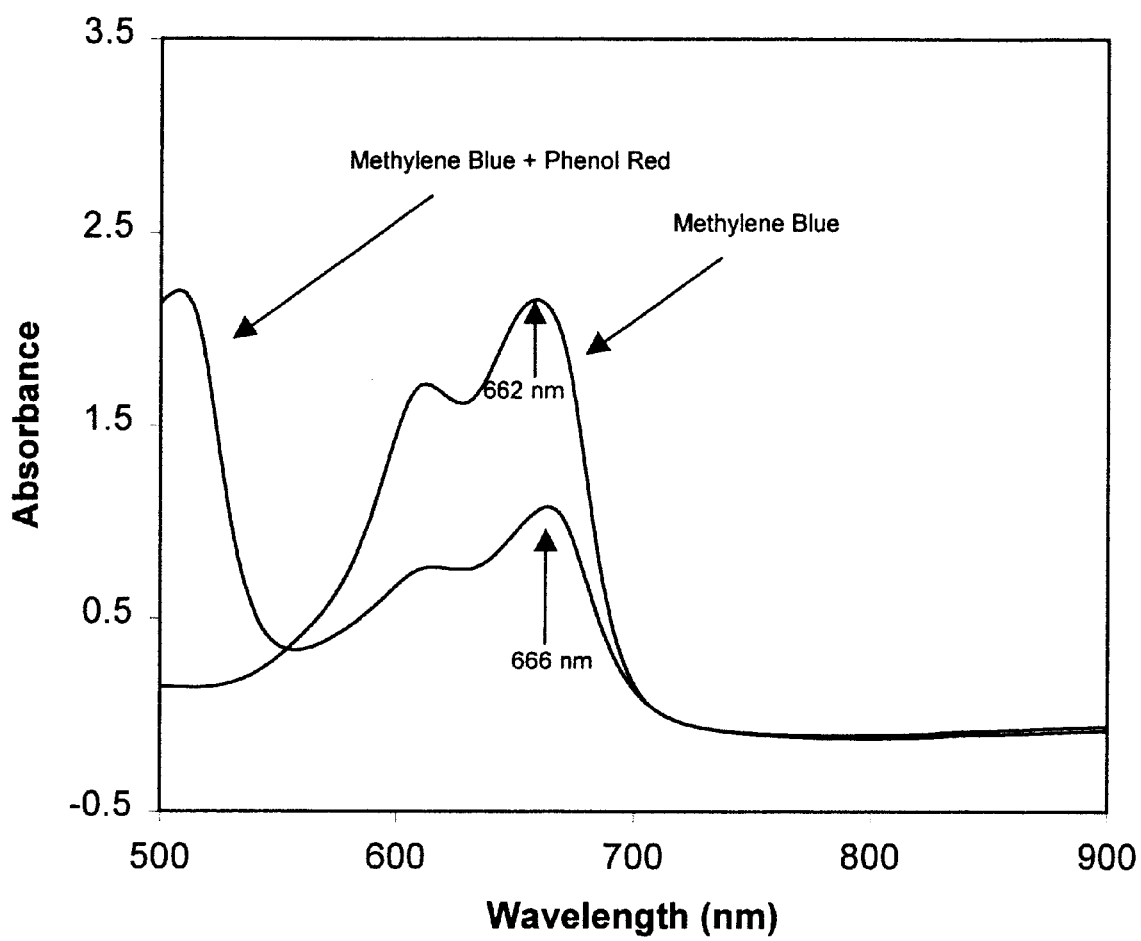

INDICATOR OF HEMOLYSIS

This application is a divisional of U.S. patent application Ser. No. 10/023,869, filed on Dec. 21, 2001. The contents of this application is incorporated by reference in its entirety.

FIELD OF INVENTION

This invention relates to the field of reagentless spectrophotometric measurements of analytes in biological and non-biological samples. More specifically, the invention relates to the calibration and monitoring of calibration algorithm(s) of spectrophotometric apparatus used for analyte measurements.

BACKGROUND

Clinical laboratory tests are routinely performed on the serum or plasma of whole blood. In a routine assay, red blood cells (RBC) are separated from plasma by centrifugation, or RBC's and various plasma proteins are separated from serum by clotting prior to centrifugation. Hemoglobin (Hb), light-scattering substances like lipid particles, and bile pigments bilirubin (BR) and biliverdin (BV) are typical blood components which will interfere with and affect spectrophotometric and other blood analytical measurements of blood analytes. Such components are referred to as interferents, and they can be measured by spectrophotometric methods. The presence of such interferents affects the ability to perform tests on the serum or plasma and as such can be said to compromise sample integrity.

Spectrophotometric measurements of blood analytes require proper calibration which can be monitored using quality control materials (QCM). QCM for blood analysis have been described in the prior art. For example U.S. Pat. No. 4,116,336 discloses the use of Amaranth or Ponceau 4 R as calibrators that mimic Hb, but these liquids must be enclosed in a flexible gas-tight container, at sub-atmospheric pressure. There is no teaching that this method is effective under atmospheric conditions. Furthermore, Amaranth and Ponceau 4 R were used separately to mimic Hb.

European Patent No. 0132399 suggests the use of one or more dyes (Acid Rhodamine B, Levafix Brilliant Yellow E-3G and Phloxine B; Phloxine Rhodamine and Atanyl Yellow 4NGL), which mimic the spectral response of whole blood and various levels of Hb in whole blood. There is no teaching of any substance or substances used to mimic an indicator of hemolysis or any analyte in serum or plasma.

WO 87/06343 discloses the use of a combination of Acid Red Dye #27 (CI 16185) and Acid Blue Dye #9 (CI 42090) and also a combination of Ponceau 3R Red Dye (CI 16155) and Acid Blue Dye #9 that simulate samples of whole blood having various levels of the fractions of Hb and of total Hb. There is no teaching of any substance or substances used to simulate an indicator of hemolysis or any analyte in serum or plasma.

Despite the fact that a number of QCM have been identified for various blood components, QCM for reagentless methods for measuring other components such as BR, BV, IL etc. are still needed. Furthermore no reliable method for selecting QCM has been described.

Warren (2001, Clinical Chemistry, Vol 47, No. 6, Supplement 2001) discloses the use of a serum pool for estimating the precision of several calibration algorithms. The use of the serum pool in monitoring the calibration algorithms is not taught.

WO-98/39634 and U.S. Pat. No. 6,268,910 B1 and U.S. Pat. No. 5,846,492 disclose methods for measuring Hb, IL, BR and BV in the presence of Hb, Hb-based blood substitute, IL, BR and BV, methods for measuring Hb-based blood substitute in the presence of Hb, IL, BR and BV, and methods for measuring Hb, IL, BR, BV and MB in the presence of Hb, IL, BR, BV and MB. However, they do not discuss QCM for monitoring calibration for any of the analytes.

It is an object of the present invention to overcome disadvantages of the prior art. This object is met by a combination of the features of the main claims. The subclaims disclose further advantageous embodiments of the invention.

SUMMARY OF INVENTION

This invention relates to the field of reagentless spectrophotometric measurements of analytes. More specifically, the invention relates to the calibration and monitoring of calibration algorithm(s) of spectrophotometric apparatus used for analyte measurements.

The present invention relates to a method (method A) of monitoring calibration of a spectrophotometirc apparatus comprising one or more calibration algorithms for one or more analytes comprising:

i) measuring absorbance of a quality control material with the apparatus to obtain a measurement, the quality control material exhibiting an absorbance spectra characterized as having a negative slope for a continuous spectral segment from about 5 nm to about 200 nm in length, the spectral segment including a principal calibration wavelength for the one or more analytes;

ii) calculating one or more concentration values from the measurement using the one or more calibration algorithms;

iii) comparing the one or more concentration values with an assigned value given to the quality control material for each of the one or more analytes; and iv) determining if there is a violation of a pre-established quality control rule, thereby monitoring the one or more calibration algorithms of the apparatus The present invention also provides the method as just defined (method A), wherein the one or more analytes is one or more analytes in a biological fluid selected from the group consisting of serum, plasma, urine, synovial fluid and cerebrospinal fluid. If the one or more analytes is:

bilirubin, then in the step of measuring (step i)) the spectral segment is selected from wavelengths of the absorbance spectra of from about 450 nm to about 600 nm;

an indicator of hemolysis, then in the step of measuring (step i)) the spectral segment is selected from wavelengths of the absorbance spectra of from about 550 nm to about 650 nm, and the indicator of hemolysis selected from the group consisting of total Hb, Oxy-Hb, and "total Hb minus met-Hb";

a hemoglobin-based blood substitute, then in the step of measuring (step i)) the spectral segment is selected from wavelengths of the absorbance spectra of from about 550 nm to about 700 nm;

met-hemoglobin, then in the step of measuring (step i)) the spectral segment is selected from wavelengths of the absorbance spectra of from about 610 nm to about 690 nm;

methylene blue, the in the step of measuring (step i)) the spectral segment is selected from wavelengths of the absorbance spectra of from about 650 nm to about 750 nm;

biliverdin, the in the step of measuring (step i)) the spectral segment is selected from wavelengths of the absorbance spectra of from about 650 run to about 800 nm.

The present invention also pertains to the method as just described (method A) wherein the quality control material comprises one or more substances selected from the group consisting of a dye, copper sulfate, total Hb, Oxy-Hb, carboxy-Hb, "total Hb minus met-Hb", cyanmet-Hb, a Hb-based blood substitute, Intralipid and a perflurocarbon-like blood substitute. Furthermore, the absorbance spectra of the one or more substances may be altered by adding a modifier. Preferably the modifier causes a spectral shift in the absorbance spectra. The modifer may be selected from the group consisting of a polymer, a protein, amaranth, and a combination thereof.

The present invention also relates to a method of monitoring calibration of a spectrophotometric apparatus comprising one or more calibration algorithms for a perflurocarbon-like blood substitute, turbidity, or a combination thereof, comprising:
i) measuring absorbance of a quality control material with the apparatus to obtain a measurement, the quality control material exhibiting an absorbance spectra from about 700 nm to about 1100 nm;
ii) calculating one or more concentration values from the measurement using the one or more calibration algorithms;
iii) comparing the one or more concentration values with an assigned value given to the quality control material for each of the perflurocarbon-like blood substitute, turbidity, or a combination thereof; and
iv) determining if there is a violation of a pre-established quality control rule, thereby monitoring the one or more calibration algorithms of the apparatus The present invention also provides a method (method B) for determining the concentration of one or more analytes in a sample in a spectrophotometirc apparatus comprising at least one primary calibration algorithm comprising:
i) monitoring calibration of the apparatus as defined above (method A);
ii) establishing that there is no violation of a pre-established quality control rule:
iii) measuring absorbance values of the sample;
iv) calculating an order derivative of absorbance of the sample; and
v) determining a concentration of the one or more analytes in the sample, by applying the primary calibration algorithm to the order derivative of absorbance value.

The present invention relates to the method as just defined (method B), wherein the one or more analytes is one or more blood analytes. If the one or more blood analytes is:
bilirubin, then in the step of measuring (step I), Method A) the spectral segment is selected from wavelengths of the absorbance spectra of from about 450 nm to about 600 nm;
an indicator of hemolysis, then in the step of measuring (step i), Method A) the spectral segment is selected from wavelengths of the absorbance spectra of from about 550 nm to about 650 nm, and the indicator of hemolysis selected from the group consisting of total Hb, Oxy-Hb, and "total Hb minus met-Hb";
a hemoglobin-based blood substitute, then in the step of measuring (step i), Method A) the spectral segment is selected from wavelengths of the absorbance spectra of from about 550 nm to about 700 nm;

met-hemoglobin, then in the step of measuring (step i), Method A) the spectral segment is selected from wavelengths of the absorbance spectra of from about 610 nm to about 690 nm;
methylene blue, the in the step of measuring (step i), Method A) the spectral segment is selected from wavelengths of the absorbance spectra of from about 650 nm to about 750 nm;
biliverdin, the in the step of measuring (step i), Method A) the spectral segment is selected from wavelengths of the absorbance spectra of from about 650 nm to about 800 nm.

The present invention also pertains to the method as just described (method B) wherein the quality control material comprises one or more substances selected from the group consisting of a dye, copper sulfate, total Hb, Oxy-Hb, carboxy-Hb, "total Hb minus met-Hb", cyanmet-Hb, a Hb-based blood substitute, Intralipid and a perflurocarbon-like blood substitute. Furthermore, the absorbance spectra of the one or more substances may be altered by adding a modifier. Preferably the modifier causes a spectral shift in the absorbance spectra. The modifer may be selected from the group consisting of a polymer, a protein, amaranth, and a combination thereof.

Furthermore, the present invention relates to method for determining the concentration of one or more analytes in a sample in a spectrophotometric apparatus comprising at least one primary calibration algorithm comprising:
i) monitoring calibration of the apparatus as defined in Method A;
ii) establishing that there is no violation of a pre-established quality control rule:
iii) measuring absorbance values of the sample;
iv) calculating an order derivative of absorbance of the sample; and
v) calculating a concentration of a perflurocarbon-like blood substitute, turbidity, or a combination thereof in terms of a lipid emulsion in the sample, by applying said primary calibration algorithm to said order derivative of absorbance value.

In one aspect of the invention there is provided method (Method C) for selecting one or more substances as a quality control material for monitoring at least one primary calibration algorithm on an apparatus comprising:
i) identifying a principal calibration wavelength for each of one or more of an analyte;
ii) screening absorption spectra of the one or more substances; and
iii) selecting one or more of the substances exhibiting a negative slope of the absorbance spectra, for a continuous spectral segment from about 5 nm to about 200 nm, the spectral segment including the principal calibration wavelength.

The present invention relates to the method as just defined (method C), wherein the one or more of an analyte is one or more analyte in a biological fluid selected from the group consisting of serum, plasma, urine, synovial fluid and cerebrospinal fluidis. If the one or more analyte is:
bilirubin, then in the step of (selecting, step iii)) the spectral segment is selected from wavelengths of the absorbance spectra of from about 450 nm to about 600 nm;
an indicator of hemolysis, then in the step of (selecting, step iii)), the spectral segment is selected from wavelengths of the absorbance spectra of from about 550 nm to about 650 nm, and the indicator of hemolysis selected from the group consisting of total Hb, Oxy-Hb, and "total Hb minus met-Hb";

a hemoglobin-based blood substitute, then in the step of (selecting, step iii)), the spectral segment is selected from wavelengths of the absorbance spectra of from about 550 nm to about 700 nm;

met-hemoglobin, then in the step of (selecting, step iii)), the spectral segment is selected from wavelengths of the absorbance spectra of from about 610 nm to about 690 nm;

methylene blue, the in the step of (selecting, step iii)), the spectral segment is selected from wavelengths of the absorbance spectra of from about 650 nm to about 750 nm;

biliverdin, the in the step of (selecting, step iii)), the spectral segment is selected from wavelengths of the absorbance spectra of from about 650 nm to about 800 nm.

The present invention also pertains to the method as just described (method C) wherein the one or more substances is selected from the group consisting of a dye, copper sulfate, total Hb, Oxy-Hb, carboxy-Hb, "total Hb minus met-Hb", cyanmet-Hb, a Hb-based blood substitute, Intralipid and a perflurocarbon-like blood substitute. Furthermore, the absorbance spectra of the one or more substances may be altered by adding a modifier. Preferably the modifier causes a spectral shift in the absorbance spectra. The modifer may be selected from the group consisting of a polymer, a protein, amaranth, and a combination thereof.

Also provided in the present invention is a method for selecting one or more substances as a quality control material for monitoring at least one primary calibration algorithm on a spectrophotometric apparatus for one or more of a perflurocarbon-like blood substitute and turbidity, wherein turbidity is measured in terms of concentration units of a lipid emulsion, comprising:

i) identifying a principal calibration wavelength for each of one or more of of the perflurocarbon-like blood substitute and the turbidity;

ii) screening absorption spectra of the one or more substances; and iii) selecting one or more of the substances exhibiting absorbance within the range from about 700 nm to about 1100 nm.

Furthermore the present invention pertains to the method as just defioned wherein the step of selecting (step iii)) is replaced within the following step of selecting:

iii) selecting one or more of the substances exhibiting absorbance spectra as having a negative slope for a continuous spectral segment from about 5 nm to about 400 nm within the range of wavelengths from about 700 nm to about 1100 nm.

The present invention provides a method (D) of monitoring the calibration of a reagentless spectrophotometric apparatus comprising one or more calibration algorithms for one or more analytes in a sample, comprising:

i) measuring absorbance of a quality control material with the spectrophotometric apparatus to obtain one or more measurements, the quality control material comprising one or more substances that absorb electromagnetic radiation, whereby predicted values for the one or more analytes can be obtained;

ii) calculating one or more of the predicted values from the one or more measurements;

iii) comparing the one or more of the predicted values with one or more assigned values given to the quality control material for the one or more analytes; and iv) determining if there is a violation of a pre-established quality control rule, thereby monitoring the calibration algorithms of the spectrophotometric apparatus.

Furthermore, the step of measuring (step i)) can be performed in any transparent or translucent vessel, and wherein the one or more wavelengths used in the one or more calibration algorithms is selected from the range from about 450 nm to 3000 nm.

The present invention also pertains to method (D) wherein the sample is a biological fluid, non-biological fluid, semi-solid, or a soft solid, and wherein the one or more calibration algorithms are developed using a statistical technique selected from the group consisting of simple linear regression, multiple linear regression, partial least squares and principal component analysis. Also included in the present invention, is the method (D), wherein the one or more analytes are selected from the group consisting of a simulator of turbidity, a perfluorocarbon-like blood substitute, bilirubin, an indicator of hemolysis, a Hb-based blood substitute, methylene blue, met-Hb and biliverdin, and the sample is selected from the group consisting of whole blood, serum, plasma, urine, synovial fluid and cerebrospinal fluid.

In yet another aspect of the invention there is provided a quality control material for mimicking two or more analytes comprising, one or more substances having a combined absorption spectrum exhibiting a negative slope for a continuous spectral segment from about 5 nm to 200 nm in a portion of an absorption spectrum, including a principal calibration wavelength, for the two or more analytes. The present invention also provides a quality control material as just described, wherein the two or more analytes are selected from the group consisting of whole blood, serum, plasma, synovial fluid, cerebrospinal fluid, urine, mucus, lymphatic fluid, semen and feces, and wherein one of the two or more analytes is:

bilirubin, and the spectral segment is selected from wavelengths of absorbance spectra of from about 450 nm to about 600 nm;

an indicator of hemolysis, and the spectral segment is selected from wavelengths of absorbance spectra of from about 550 m to about 650 nm, indicator of hemolysis selected from the group consisting of total Hb, Oxy-Hb, and "total Hb minus met-Hb";

hemoglobin-based blood substitute, and the spectral segment is selected from wavelengths of the absorbance spectra of from about 550 nm to about 700 nm;

met-hemoglobin, and the spectral segment is selected from wavelengths of the absorbance spectra of from about 610 nm to about 690 nm;

methylene blue, and the spectral segment is selected from wavelengths of the absorbance spectra of from about 650 nm to about 750 nm;

biliverdin, and the spectral segment is selected from wavelengths of the absorbance spectra of from about 650 nm to about 800 nm;

either a simulator of turbidity, or a perflurocarbon-like blood substitute characterized as having an absorbance spectra of from about 700 nm to about 1100 nm;

either a simulator of turbidity or a perflurocarbon-like blood substitute, characterized as having a negative slope for a continuous spectral segment from about 5 nm to about 400 nm within the range of from about 700 nm to about 1100 nm.

The quality control material as just described may also comprise a dye, copper sulfate, total Hb, Oxy-Hb, carboxy-Hb, "total Hb minus met-Hb", cyanmet-Hb, a Hb-based blood substitute, a lipid emulsion and a perflurocarbon-like blood substitute, or a combination thereof. Furthermore, the absorbance spectra of the quality control material may be altered by adding a modifier. Preferably the modifier causes a spectral shift in the absorbance spectra. The modifer may be selected from the group consisting of a polymer, a protein, amaranth, and a combination thereof.

The present invention embraces a quality control material for use in a reagentless spectrophotometric apparatus, comprising, one or more substances that mimic one or more analytes in serum, plasma, urine, synovial fluid or cerebrospinal fluid. The one or more analytes of the quality control material may be selected from the group consisting of a simulator of turbidity, a perfluorocarbon-like blood substitute, bilirubin, an indicator of hemolysis, a Hb-based blood substitute, methylene blue, met-Hb and biliverdin. When the one or more analytes is an indicator of hemolysis in serum or plasma, the indicator of hemolysis is one of total Hb, oxy-Hb or "total Hb minus met-Hb," and the quality control material is exposed to atmospheric conditions. The present invention pertains to the quality control material as just above, wherein the one or more substances are selected from the group consisting of amaranth, acid fuchsin, basic fuchsin, ponceau S, chromotrope 2R, phenol red, crystal ponceau, methyl orange, a Hb-based blood substitute, total Hb, oxy-Hb, carboxy-Hb, cyanmet-Hb, a polymer, and a protein. The present invention also provides a quality control material as just defined for use in a reagentless spectrophotometric apparatus, comprising, one or more substances that mimics an indicator of hemolysis, wherein the indicator of hemolysis is selected from the group consisting of oxy-Hb and "total Hb minus met-Hb," and wherein the quality control material is exposed to atmospheric conditions. Preferably the quality control material is not supplemented with bilirubin.

The present invention pertains to a quality control material for use in a reagentless spectrophotometric apparatus, comprising, one or more substances that mimics an indicator of hemolysis, wherein the one or more substances are selected from the group consisting of total Hb, oxy-Hb, "total Hb minus met-Hb," cyanmet-Hb, amaranth, acid fuchsin, basic fuchsin, ponceau S, chromotrope 2R, phenol red, crystal ponceau, methyl orange, a Hb-based blood substitute, oxy-Hb, carboxy-Hb, cyanmet-Hb, a polymer, and a protein., and wherein the quality control material is exposed to atmospheric conditions. Preferably the quality control material is not supplemented with bilirubin.

Also, the present invention is directed to a quality control material for use in a reagentless spectrophotometric apparatus, comprising, one or more substances that mimics an indicator of hemolysis, wherein the one or more substances are selected from the group consisting of total Hb, oxy-Hb, "total Hb minus met-Hb," cyanmet-Hb, acid fuchsin, basic fuchsin, ponceau S, chromotrope 2R, phenol red, crystal ponceau, methyl orange, a Hb-based blood substitute, oxy-Hb, carboxy-Hb, cyanmet-Hb, a polymer, and a protein. Preferably the quality control material is not supplemented with bilirubin.

The present invention embraces a quality control material for use in a reagentless spectrophotometric apparatus, comprising, one or more substances that mimic an indicator of hemolysis, wherein the indicator of hemolysis is selected from the group consisting of oxy-Hb and "total Hb minus met-Hb". Preferably the quality control material is not supplemented with bilirubin.

The present invention also provides a quality control material for use in a reagentless spectrophotometric apparatus, comprising, one or more substances that mimics one or more of, biliverdin, bilirubin, methelene blue, met-Hb, a simulator of turbidity, a perflurocarbon-like blood substitute, a Hb-based blood substitute.

The present invention includes a quality control material for use in a reagentless spectrophotometric apparatus, comprising, one or more substances that mimics one or more of, an indicator of hemolysis, biliverdin, bilirubin, methelene blue, met-Hb, a simulator of turbidity, a perflurocarbon-like blood substitute, a Hb-based blood substitute wherein said indicator of hemolysis is selected from the group consisting of oxy-Hb and "total Hb minus met-Hb". Preferably the quality control material is not supplemented with bilirubin.

The present invention also pertains to a quality control material for use in a reagentless spectrophotometric apparatus, comprising, one or more substances that mimics an indicator of hemolysis, wherein the substance is selected from the group consiting of total-Hb and oxy-Hb, wherein the oxy-Hb accounts for about 95% of total Hb, or the total-Hb comprises about 95% oxy-Hb, and wherein the quality control material is exposed to atmospheric conditions. Preferably the quality control material is not supplemented with bilirubin.

The present invention also provides a method (E) for producing a corrected predicted value for an indicator of hemolysis in a sample, in the presence of met-Hb, the method comprising the steps of:

i) developing a first primary calibration algorithm for one of a total Hb, or an oxy-Hb, for predicting a first value for either the total Hb or the oxy-Hb in said sample;

ii) deriving a second primary calibration algorithm for the met-Hb, for predicting a second value for the met-Hb in the sample; and iii) adding the predicted second value for the met-Hb to either the predicted first value for total Hb or the predicted first value for oxy-Hb, to a produce a the corrected predicted value for an indicator of hemolysis.

Furthermore, the present invention pertains to the method as just described (method (E)), wherein the step of developing (step i)) and the step of deriving (step ii)), each comprises the steps of:

a) collecting an absorbance measurement for each calibration sample in a primary calibration set, the calibration sample having known reference values for each analyte;

b) calculating an order derivative of absorbance for each of the calibration sample; and c) creating a primary calibration algorithm for each of the indicator of hemolysis and the met-Hb using the derivative of absorbance, the known reference values, and a statistical technique.

The present invention also includes the above method (method (E)), wherein in the step of collecting (step a)), the reference values for either the total Hb or the oxy-Hb, are obtained from the measured amounts of the total Hb or the oxy-Hb, in the presence of one or more of oxy-Hb, deoxy-Hb, carboxy-Hb and met-Hb in the calibration samples. Preferably, the oxy-Hb accounts for about 95% of total Hb, or the total-Hb comprises about 95% oxy-Hb, and the sample is one of serum, plasma, urine, synovial fluid or cerebrospinal fluid.

The present invention also embraces a method (F) for flagging a predicted value for an indicator of hemolysis in a sample, in the presence of met-Hb, comprising:

i) developing a first primary calibration algorithms for one of a total Hb or an oxy-Hb, for predicting a value for either the total Hb or the oxy-Hb in said sample;

ii) deriving a second primary calibration algorithm for the met-Hb, for predicting a second value for the met-Hb in said sample;

iii) determining if the predicted met-Hb value exceeds a pre-determined value; and iv) flagging the predicted value for the total Hb, said oxy-Hb or a combination thereof, when the predicted met-Hb value exceeds said pre-determined value.

Furthermore, the present invention provides the method (F) defined above wherein the steps of developing (step i)) and deriving (step ii)), each comprises the steps of:

a) collecting an absorbance measurement for each calibration sample in a primary calibration set, the calibration sample having known reference values for each analyte;

b) calculating an order derivative of absorbance for each of the calibration sample; and c) creating a primary calibration algorithm for each of the indicator of hemolysis and the met-Hb using the derivative of absorbance, the known reference values, and a statistical technique.

Preferably, in the step of collecting (step a)), the reference values for each of the total Hb or the oxy-Hb are obtained from the measured amounts of the total Hb or the oxy-Hb, in the presence of one or more of oxy-Hb, deoxy-Hb, carboxy-Hb and met-Hb in the calibration samples, and wherein the oxy-Hb accounts for about 95% of total Hb, or wherein the total-Hb comprises about 95% oxy-Hb. Furthermore, the invention includes the above method wherein sample is one of serum, plasma, urine, synovial fluid or cerebrospinal fluid.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

Figure 1:
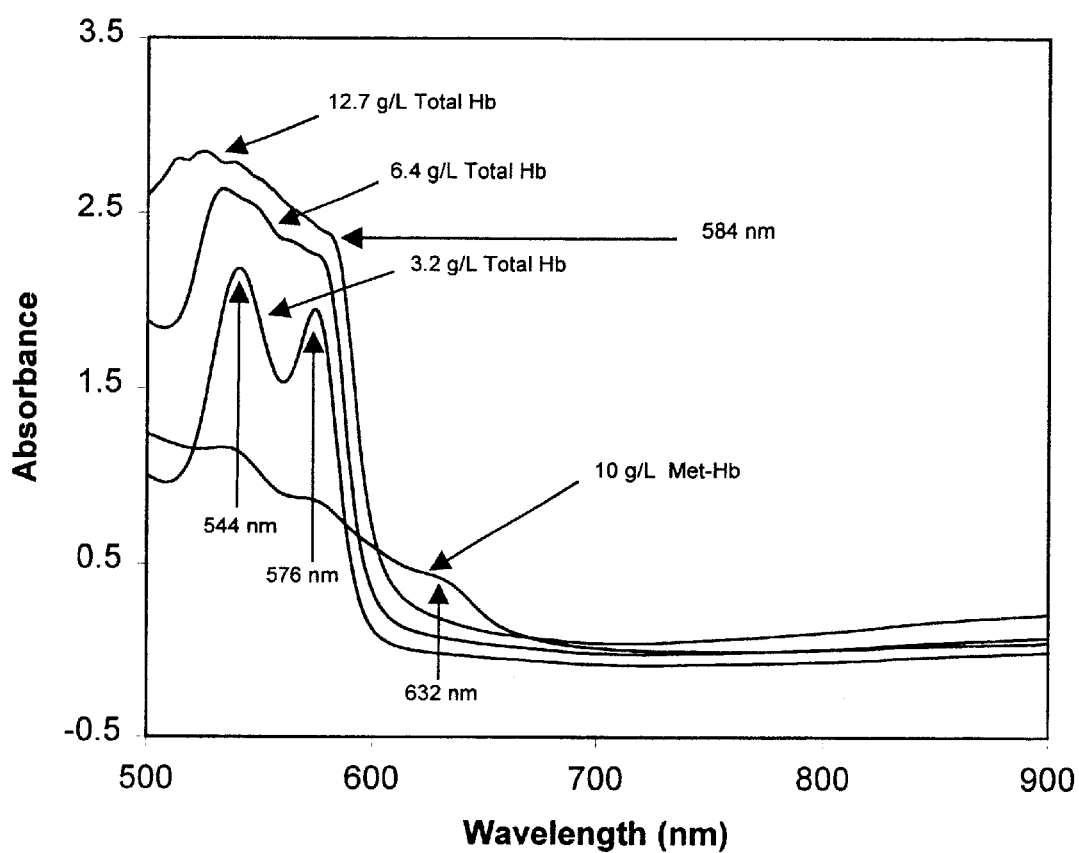
FIG. 1 is a graphic representation of the absorbance spectra of three different concentrations of total Hb, and one concentration of met-Hb as shown.

As used herein, g/L means grams per liter and mg/dL means milligrams per deciliter.

DESCRIPTION OF THE INVENTION

This invention relates to the field of reagentless spectrophotometric measurements of analytes. More specifically, the invention relates to the calibration and monitoring of calibration algorithm(s) of spectrophotometric apparatus used for analyte measurements.

The following description is of preferred embodiments by way of example only and without limitation to the combination of features necessary for carrying the invention into effect.

In the present application the following abbreviations are used:

| | |
|---|---|
| BR | Bilirubin |
| BV | Biliverdin |

-continued

| | |
|---|---|
| Hb | Hemoglobin |
| IL | Intralipid ™ |
| Met-Hb | Methemoglobin |
| MB | Methylene Blue |
| QC | Quality Control |
| QCM | Quality Control Material |
| Hg | Mercury |
| RBC | Red blood cell |
| PEG | Polyethylene Glycol |
| PVP | Polyvinylpyrrolidone |

By "Primary Calibration" it is meant a process used to develop a "primary calibration algorithm" for an apparatus for a given analyte.

By "Derivative of Absorbance" it is meant an order derivative of the absorbance spectrum. Zero order derivative of absorbance is the measured absorbance. The first order derivative of absorbance at a particular wavelength is the slope of the absorbance spectrum at that wavelength; the second order derivative of absorbance at a particular wavelength is the slope of the first derivative absorbance spectrum at said wavelength. Higher order derivative (third, fourth etc.) of absorbance can similarly be obtained by taking the slope of the derivative absorbance spectrum of the order immediately below (second, third etc.) Methods of calculating a derivative of absorbance at a particular wavelength are well known by those skilled in the art. The calculation of the first derivative of absorbance at a particular wavelength may consist in taking the difference in absorbances at the two wavelengths that encompass the wavelength of interest. Other methods of calculating derivative of absorbance may use the absorbances at several different wavelengths, where smoothing is an integral part of the derivative process. It should be understood that with a greater degree of smoothing, there is also a greater loss of signal details in the absorbance spectrum or derivative of absorbance spectrum. The minimum number of wavelengths that may be used to calculate a derivative of absorbance is two wavelengths.

By "Primary Calibration Algorithm" it is meant a linear combination of the type $Y=A(x)+Bx_1+ \ldots +C$ where Y is the concentration of a given analyte, A, B and C are contants and $x, x_1, \ldots$ are the order derivative of absorbance values at specified wavelengths. The equation is preferably obtained by multiple linear regression of a sample set, but other statistical techniques for example but not limited to, simple linear regression, PLS and PCA may also be used and are within the scope of this invention. The sample set used for calibration is relatively large, and the samples are natural or very close to natural samples. The primary calibration set should include all the variability expected in a sample, in order to develop robust calibration algorithm(s). The term "calibration algorithm" when used and unless otherwise specified, means the primary calibration algorithm, or any modification of the primary calibration algorithm, whereby the modification is for improvement in accuracy of predicted values of an analyte.

By analyte it is meant a substance being measured in a sample.

By "quality control material (QCM)" it is meant a solution comprising one or more absorbing or light scattering substances that may be used for monitoring the performance of primary calibration algorithms as will be described below. Substances comprising QCMs include but are not limited to synthetic substances, for example but not limited to copper sulfate and dyes, and non-synthetic substances, including biological molecules such as total Hb, Oxy-Hb, carboxy-Hb and "total Hb minus met-Hb;" and modified biological materials such as cyanmethemoglobin (cyanmet-Hb), and Hb-based blood substitutes, or a combination thereof, as a mimic of an indicator of hemolysis. Other biological substances that may be used as QCM's include bilirubin, biliverdin, or a lipid emulsion, for example but not limited to IL, or perfluorocarbon-like blood substitutes, in any combination, as a mimic of themselves (e.g., BR used to mimic BR and BV used to mimic BV, but not limited to BR and BV) or, in the case of IL or perfluorocarbon-like blood substitutes, as a mimic of a simulator of turbidity. However, the use of bilirubin as a QCM is not preferred due its light sensitivity. If human Hb is obtained by obtaining a hemolysate of whole blood from a normal subject, there will be low levels of bilirubin in the hemolysate, according to the normal serum or plasma BR concentration. Therefore, if a sample is supplemented (or spiked) with the hemolysate and not spiked with BR, the sample will still contain some BR from the serum or plasma in the hemolysate. It should therefore be understood that although it is preferred not to spike the sample with BR, the sample may still contain some BR from the other blood products.

Furthermore, in respect of alternatives to mimic a simulator of turbidity, any substance that produces an absorbance pattern similar to the "apparent" absorbance in the region used by a calibration algorithm, may be used. One such example is copper sulfate, which is a non-light-scattering transparent substance. Turbidity causes an increase in the "apparent" absorbance. Apparent absorbance is based on the fact that transmitted light is measured and converted to absorbance units, therefore an apparatus cannot distinguish true absorbance from loss of light due to scattering. In some cases, as shown for IL (a lipid emulsion) in FIG. 6, turbidity produces absorbance that is inversely proportional to wavelength. QCM may also comprise spectrum modifiers. The term "simulator of turbidity" is used to refer to the analyte measured to quantify turbidity.

QCMs are preferably stable under storage and measurement conditions. It should be understood that any one or more antimicrobiological agents that does not affect the absorbance spectrum of the QCM significantly, can be added to the QCM as preservatives By spectral modifiers it is meant any substance or physico-chemical conditions that can modify the absorbance spectrum of the absorbing or light scattering substances. For example, it is well known that the pH of a solution can influence the absorbance spectrum of certain compounds. Such spectral modifiers may be used to mimic the physico-chemical conditions in a sample such as blood. Some spectral modifiers, when added to a QCM may result in a non-additive shift in the resultant absorbance spectrum. Examples of a substance that may result in an unexpected spectral shift include amaranth, polymers such as PVP and PEG, or proteins such as albumin. However, a pH change may also result in an unexpected non-additive spectral shift, for example but not limited to, modifying the pH of a phenol red solution.

Figure 2:
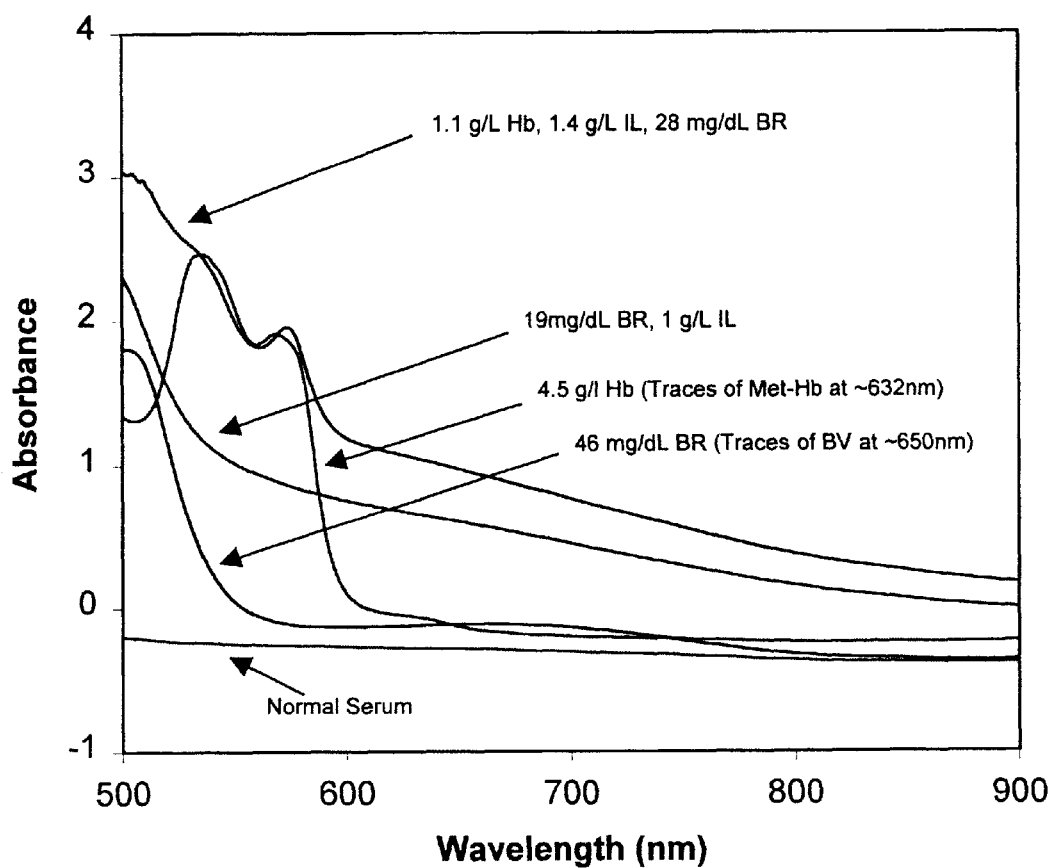
FIG. 2 is a graphic representation of the absorbance spectra of normal serum, Br with traces of BV, Hb with traces of met-Hb, a mixture BR and IL, a mixture Hb, IL and BR with concentrations shown.

QCM may be used to monitor the primary calibration algorithm of an apparatus prior to the measurement of either biological or non-biological samples, these samples maybe liquid, semi-solid or soft solid. Furthermore, the samples can be measured in any transparent or translucent container or vessel. Suitable samples are samples capable of producing an absorption spectrum in the NIR region and adjacent visible spectrum (about 450 nm to about 3000 nm) and include but are not limited to: whole blood, plasma, serum, synovial fluid, cerebrospinal fluid, urine, mucus, lymphatic fluid, feces, semen, milk, cheese, cottage cheese, yogourt, ice cream, wine and other beverages and semi-solid food, soft solid food and the like. It is not required that the absorbance spectrum of a QCM resemble the absorbance spectrum of an analyte, since a mixture of analytes can produce an absorbance spectrum that is very different from any one pure analyte, for example but not limited to a mixture of Hb, IL and BR as shown in FIG. 2, and this mixture may be used as a QCM as described herein. One requirement of a QCM is that the order derivative of absorbance of the QCM, when processed by a calibration algorithm, should produce a suitable predicted value, as defined earlier.

By "Primary Calibration Set" it is meant the samples used for primary calibration.

By "Primary Calibration Wavelength(s)" it is meant the wavelength(s) used in a primary calibration algorithm.

By "Principal calibration wavelength" it is meant a wavelength of the primary calibration algorithm exhibiting a high correlation between an order derivative of absorbance, and the analyte concentration. The principal calibration wavelength may be different for the same analyte in different compositions. The primary calibration algorithm may optionally comprise one or more other wavelengths exhibiting low correlations between an order derivative of the absorbance and the analyte concentration. These other wavelengths are referred to as secondary calibration wavelengths. Secondary calibration wavelengths add robustness to the primary calibration algorithm especially in the presence of interferents which may have absorption bands overlapping that of the principal calibration wavelength(s) and therefore affect the correlation between the absorbance at the principal calibration wavelength and the analyte concentration. A continuous spectral segment of about 5 to 200 nm that contain at least one principal calibration wavelength is referred to as a "Principal calibration section."

By "absorbance" it is meant a reduction of light intensity caused by a sample. According to Beer's law, Absorbance= Log(1/Transmitted light), which applies to non-light-scattering samples. The measured parameter is the amount of light transmitted through a sample, and the transmitted light (or transmittance) is then converted to absorbance units. When a sample is light-scattering and Beer's law is applied, an apparatus cannot distinguish "true absorbance" from loss of light due to scattering, hence the term "apparent absorbance" should be used. It should be understood that when the term "absorbance" is used, it could mean either "true absorbance" or "apparent absorbance," or both, since it is not always obvious whether the sample is light-scattering or non-light-scattering. Although all examples are given with respect to absorbance, it should be understood that absorbance can be replaced with Log(1/Reflectance), when reflectance is measured instead of transmittance, and reflectance measurement is within the scope of the present invention.

By "interferents" it is meant an analyte whose presence in a sample, particularly a serum or plasma sample, interferes with the determination of the presence and/or quantification of another analyte.

Intralipid™ (IL) is an example of a lipid emulsion that simulates naturally occurring chylomicrons in blood. The major cause of turbidity in serum and plasma is fat particles, for example chylomicrons, therefore IL, or other lipid emulsions may be used to simulate turbidity in blood. The term "simulator of turbidity" is used to refer to the "analyte" measured to quantify turbidity. The term "mimic of a simulator of turbidity" is used to refer to a QCM, for example but not limited to, perfluorocarbon-like blood substitute is a QCM that mimics a simulator of turbidity, or in the case of a non-light-scattering transparent substance, copper sulfate is another QCM that can mimic a simulator of turbidity.

By "indicator of hemolysis" it is meant any substance present within a red blood cell (RBC) and not present in the plasma that surrounds the RBC. An example of an indicator of hemolysis includes, but is not limited to, total Hb, Oxy-Hb or "total Hb minus met-Hb." A sample of known oxy-Hb concentration where the Oxy-Hb fraction is about 95% or the total Hb, can be considered to have a total Hb concentration of same value as the oxy-Hb concentration. Similarly, a sample of known total Hb concentration that comprises about 95% oxy-Hb, can be considered to have an oxy-Hb concentration of the same value as the total Hb concentration. Acceptability of the aforesaid approximation of total Hb or oxy-Hb concentration, depends on the required accuracy of the predicted value of the total Hb or the oxy-Hb.

By "predicted value," it is meant a value of an analyte obtained when the primary calibration algorithm for the analyte is applied to the order derivative of absorbance of a sample. As indicated earlier, a primary calibration algorithm is an equation comprising a predicted value of the analyte as the dependant variable, and a linear summation of a constant and one or more terms. Each term is the product of a constant and an independent variable (Examples 1 to 7). The independent variable is the order derivative of absorbance of the sample at a specific wavelength.

By "reference value" of an analyte, it is meant the value of the analyte assigned to a sample. A reference value is typically estimated by a method known within the art, which has a suitable level of accuracy. For example which is not to be considered limiting in any manner, known amounts of an analyte added to a sample can be used as the reference value, or, as in the case of an indicator of hemolysis, the indicator of hemolysis can be measured. In the case of an indicator of hemolysis, the preferred indicators are total Hb, oxy-Hb and "total Hb minus met-Hb.". The cyanmethemoglobin (cyanmet-Hb) method, which is well known to a person of skill in the art will measure all the Hb species present, i.e., oxy-Hb, deoxy-Hb, carboxy-Hb and met-Hb. Oxy-Hb can be measured by known reagentless spectrophotometric methods, for example Harboe or Tietz (Harboe, M., 1959, A method of determination of hemoglobin in plasma by near ultraviolet spectrophotometry. Scand. J. Clin. Lab. Invest, pp. 66–70; Tietz Textbook of Clinical Chemistry, $2^{nd}$ Ed, 1994, pp 2022–2025), which is incorporated herein by reference. The Hb species actually measured by the reagentless spectrophotometric apparatus depends on both the reference method used to measure the analyte, and the substances included in the primary calibration method. This is discussed in details under the heading of "QCM for an indicator of hemolysis." A sample of known oxy-Hb concentration where the Oxy-Hb fraction is about 95% or the total Hb, can be considered to have a total Hb concentration of same value as the oxy-Hb concentration. Similarly, a sample of known total Hb concentration that comprises about 95% oxy-Hb, can be considered to have an oxy-Hb concentration of the same value as the total Hb concentration.

By "blood substitutes" it is meant any substance that can be used instead of whole blood or RBC's for transfusion. Blood transfusion is a life-saving process after severe blood loss during trauma or surgery. Some advantages of using a blood substitute instead of blood or red blood cells are as follows: blood substitutes are expected to be universally compatible with all blood types, therefore cross-matching will not be necessary; maximum storage time of blood is 42 days, whereas the blood substitutes could have a much longer shelf-life; the purification process of the blood substitute may include heat treatment, which can eliminate the threat of hazardous viruses.

Most blood substitutes under development are made from human or bovine Hb. Hemoglobin comprises four protein subunits, which are two pairs of identical polypeptide chains. Each subunit has a molecular weight of about 16,000, with a cleft that contains a heme (iron-porphyrin) group that is the site of oxygen uptake. The subunits are not covalently linked, and require the red cell membrane to keep the subunits together. A hemoglobin molecule is too big to be filtered by the kidney, but the subunits are small enough to become lodged in the kidney and cause kidney failure. In Hb-based blood substitutes, the subunits of the Hb are chemically cross-linked with each other or to large polymers, for stability. The Hb subunits may be inter- or intra-molecularly cross-linked. Regardless of the protein or polymer surrounding the heme groups, the absorbance spectrum looks very much like normal Hb. T. M. S. Chang provides a detailed review of blood substitutes in volumes I and II of "Blood Substitutes: Principles, Methods, Products and Clinical Trials" 1998, published by Karger Landes Systems.

Another type of blood substitute has been reported, which is a milky-white emulsion containing tiny beads of perfluorocarbons wrapped in a surfactant. These "milky-white" blood substitutes will be referred to in this disclosure as "perfluorocarbon-like" blood substitutes. It should be understood that perfluorocarbon-like blood substitutes includes all blood substitutes that are milky-white emulsions.

Any suitable spectrophotometric apparatus may be used for the measurement of calibrator materials, QCMs, plasma and serum samples, or a combination thereof, as described herein. An example, which is not to be considered limiting, of such an apparatus and the primary calibration algorithms is given in WO9838961. If more than one apparatus is to be used, for example for the purposes for calibration, then it is preferred that each apparatus has similar components. The major components of an apparatus may comprise:

1. A spectrophotometer comprising: A diffraction grating, focussing lenses, slits, and a linear diode array detector (sometimes referred to as simply a linear diode array). It is preferred that spectrophotometers have similar components, including the number of pixels in the linear diode array. It should be understood that other arrays, for example but not limited to CCD (charged coupled detector) arrays, may also be used as described herein. The spectrophotometer can operate in a single or dual beam configuration. If the spectrophotometer is a dual beam spectrophotometer, one of the beams acts as a reference beam and the other is the sample beam; two shutters are required to facilitate the sample and reference measurements. It should be understood that the measurable wavelength range of the spectrophotometer depends on the grating, the light source and the detector, and a wavelength range of about 450 nm to about 3000 nm is within the scope of this invention.
2. A light source
3. A power supply
4. A sample holder with light coming from the lamp through an optical fiber or glass rod, and light transmitted through the sample to the spectrophotometer via a second optical fiber or glass rod.
5. A circuit board that includes an amplifier and an analog to digital converter, is required to interface the linear diode array detector and a microprocessor. The Primary Calibration Algorithm and other information like the wavelength calibration table may be imbedded in an EPROM.
6. Software that may comprise features for: utilizing the calibration algorithm(s); interpolating absorbances; mapping absorbances to a standard set of wavelengths; smoothing; creating derivatives of absorbances; calculating analyte concentrations.

Differences in absorbances for the same sample may occur between apparatus for a number of reasons including:

1. The corresponding pixels in similar linear diode array detectors respond differently to the same amount of light.
2. The incremental wavelength per pixel or pixeldispersion may vary between any two similar linear diode array detectors.
3. The physical distances between pixels in the linear diode array are not always constant within a linear diode array, and also between similar linear diode arrays.
4. Spectrophotometers contain wavelength inaccuracies, depending on the method used for wavelength calibration.
5. Variability in other components of the spectrophotometers, e.g., the diffraction grating, filters, and slits.

The differences in absorbances between spectrophotometers, differences in sample containers, and differences in sample composition, all contribute to the identification of different principal calibration wavelengths, and the derivation of different primary calibration algorithms. An example of various different primary calibration algorithms for the same analyte, for example Hb, can be found in equations 1–6 of Examples 1–5 below.

In one aspect of the present invention there is provided a method for selecting QCMs that can be used to monitor calibration algorithms and to calibrate a spectrophotometric apparatus used to measure the concentrations of blood analytes.

Thus, in one embodiment of the present invention there is provided a method for selecting one or more substances as a quality control material for monitoring at least one primary calibration algorithm on a spectrophotometric apparatus comprising:

i) identifying a principal calibration wavelength for each of one or more of a blood analyte;
ii) screening absorption spectra of said one or more substances; and
iii) selecting one or more of said substances exhibiting a negative slope of said absorbance spectra, for a continuous spectral segment from about 5 nm to about 400 nm, said spectral segment including said principal calibration wavelength.

This method requires that a primary calibration algorithm is already present on a spectrophotometric apparatus. Primary calibration of an apparatus is a cumbersome, time intensive exercise because it requires the measurements of absorbance of a relatively large set of samples referred to as primary calibration sets. The samples in the primary calibration set should be real or very close to real samples. Preferably, samples include all the absorbance variability expected in a sample, whereby the sample variability becomes built into the primary calibration algorithm. Vessels also contribute variability, and it is possible to develop one or more primary calibration algorithm using a combination of more than one vessel, whereby the vessel variability becomes built into the primary calibration algorithm. However, development of primary calibration algorithms that are specific to a particular type of vessel is preferred.

A primary calibration algorithm can be obtained as follows: Absorbance spectra are obtained for several samples that cover a concentration range of a given analyte for which the primary calibration algorithm is being developed. It is preferred that the samples include all the absorbance variability expected in a sample, whereby the sample variability becomes built into the primary calibration algorithm. A multiple linear regression is then performed to develop a linear combination having the order derivative of absorbance at specific wavelengths as the independent variable, and the concentration of the analyte as the dependent variable. Other statistical methods, for example simple linear regression that uses only one wavelength, partial least squares (PLS) and principal component analysis (PCA), may also be used. The equation thus obtained is a primary calibration algorithm.

Zero order derivative of absorbance (also referred to as raw absorbance) or any order derivative of absorbance may be used in the calibration process with second order derivative of absorbance being preferred, and first order derivative of absorbance being more preferred. One exception is for a simulator of turbidity (for example IL), where both zero order derivative of absorbance and the first derivative of absorbance are preferred. With respect to a lipid emulsion, for example IL, for samples in containers that attenuate light in a reproducible manner, zero order derivative of absorbance is preferred over first order derivative of absorbance, because the resulting primary calibration algorithm covers a wider analytical range i.e. a wider range wherein the relationship between the predicted values and actual concentrations of a lipid emulsion, for example IL, is linear. For samples in, for example, blood bag tubing, which may or may not contain black writing in the light path, as discussed in U.S. Pat. No. 6,268,910 B 1, the first order derivative of absorbance is preferred.

Software tools used for developing primary calibration algorithms comprises of the following: Matlab™ used to create programs for smoothing absorbances and obtaining derivative of absorbances. MS Excel™ may be used to develop macros for calculating derivative of absorbances; StatView™ used to create algorithms by a process called "step-wise multiple linear regression." In the step-wise linear regression, the order derivative of absorbance measurements for all the wavelengths is presented to the StatView™ program; only the wavelengths at which the order derivative of absorbance contribute to the calibration fit at a predetermined level of significance are selected for the algorithms. Pirouette™ may be used to create calibration algorithms by PLS or PCA, using the measurements for all the wavelengths, or selected sections of the absorbance spectra. It will be appreciated however that other software tools may also be used. Examples of the primary calibration procedure, in respect of blood analytes, are given in the example section below. It will be appreciated that a primary calibration algorithm may contain from a single wavelength term, in the simplest case, to multiple terms that use many wavelengths.

In order to practice the present invention, it is preferred that at least one apparatus that contains at least one primary calibration algorithm for at least one analyte is used.

The primary calibration algorithms can vary in robustness, depending on the make up of the primary calibrators. Once a primary calibration algorithm has been obtained for a given analyte, the concentration of the analyte in a sample (a predicted value) can be obtained by acquiring an absorption spectrum of the sample, and applying the primary calibration algorithm for the analyte. No reagents are required. Primary calibration algorithms for any number of analytes can be installed in an apparatus, and they can be applied to the same absorbance data, in order to obtain concentrations of the analytes. Furthermore, more than one primary calibration algorithm can be installed for one analyte. The use of multiple primary calibration algorithms may be used to extend the analytical range of the spectrophotometric apparatus at higher or lower analyte concentrations.

The next step in the method of selecting a QCM for monitoring the calibration algorithm is to identify one or more sections of the absorption spectrum of the analyte that comprises at least one principal calibration wavelength. The identified one or more sections of the absorbance spectrum preferably have a continuous spectral segment of about 5 nm to 400 nm. These one or more sections are referred to as "principal calibration sections." In a preferred embodiment, an identified principal calibration section exhibits a negative slope in the absorption spectrum for a continuous spectral segment of about 5 to 200 nm in length and more preferably of about 10 to 150 nm in length; for a simulator of turbidity or a perfluorocarbon-like blood substitutes, the spectral segment is preferably from about 5 nm to about 400 nm. It is preferred that the slope of the identified section or the absorption spectrum at the principal calibration wavelength is negative.

A QCM for a given analyte can then be selected by screening substances that may be potential QCMs, and selecting those having an absorption spectrum exhibiting a negative slope for a continuous spectral segment of about 5 nm to 200 nm (or about 5 nm to about 400 nm in the case of a simulator of turbidity or a perfluorocarbon-like blood substitutes) in the principal calibration section.

The process of selecting a QCM for Hb will now be described with the following non-limiting example. Equation 1 (see Example 1) provides a primary calibration algorithm for Hb in which the primary calibration wavelengths are 584 nm, 599 nm and 617 nm. This primary calibration algorithm uses the first order derivative, of the absorbance. It can be seen from FIG. 1 that the 584 nm and 599 nm wavelengths are in the broad shoulder of the absorption sprectrum of Hb between approximately 576 nm and 650 nm. Furthermore this shoulder exhibits a negative slope. In this example the principal calibration wavelength is at 584 nm, and lies in the region of the absorbance spectrum that exhibits a negative slope. It should be understood that depending on the software used to calculate the first derivative of absorbance, the calculated number could be either positive (+) or negative (−) number. In the examples shown, the signs (+or −) given to the calculated first derivatives were not disclosed in the references; the calibration algorithm (or equation) takes this into account and assigns the appropriate sign to the constants. In the particular equation referred to above, where an example of a principal wavelength is 584 nm, the negative slope was given a negative value. Once this negative value is known, it helps to identify the principal calibration wavelength; the product of the first derivative of absorbance (when given the appropriate sign) and the constant must be a positive value. This explains why the constant term in the same equation is "−16.81".

Figure 7A:
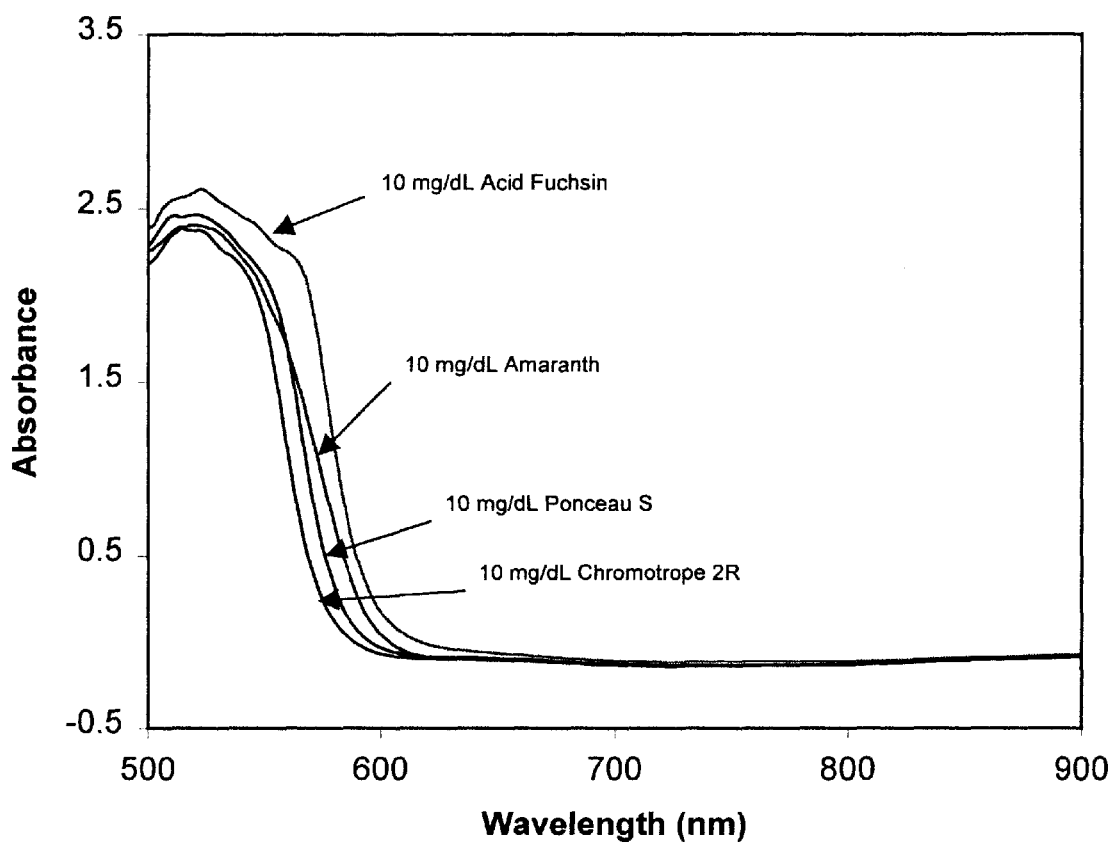
FIGS. 7(A–C) is a graphic representation of the absorbance spectra of 8 different substances (Methyl Orange, Phenol Red, Basic Fuchsin, Acid Fuchsin, Crystal Ponceau, Amaranth, Ponceau S, and Chromotrope 2R) with negative absorbance slopes between about 500 nm and about 670 nm. For clarity, 4 are shown in Figure A and 4 in Figure B. Figure C shows a mixture of equal amounts of all 8 substances.
Figure 7B:
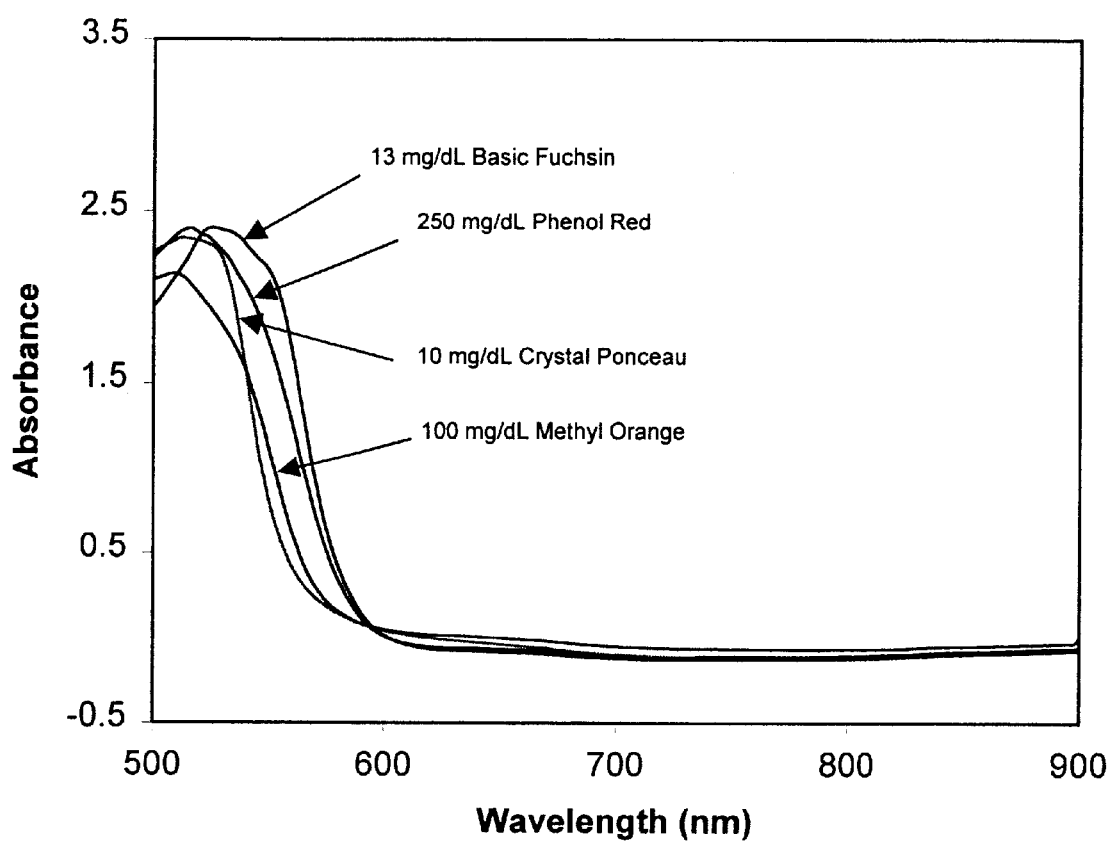
Figure 7C:
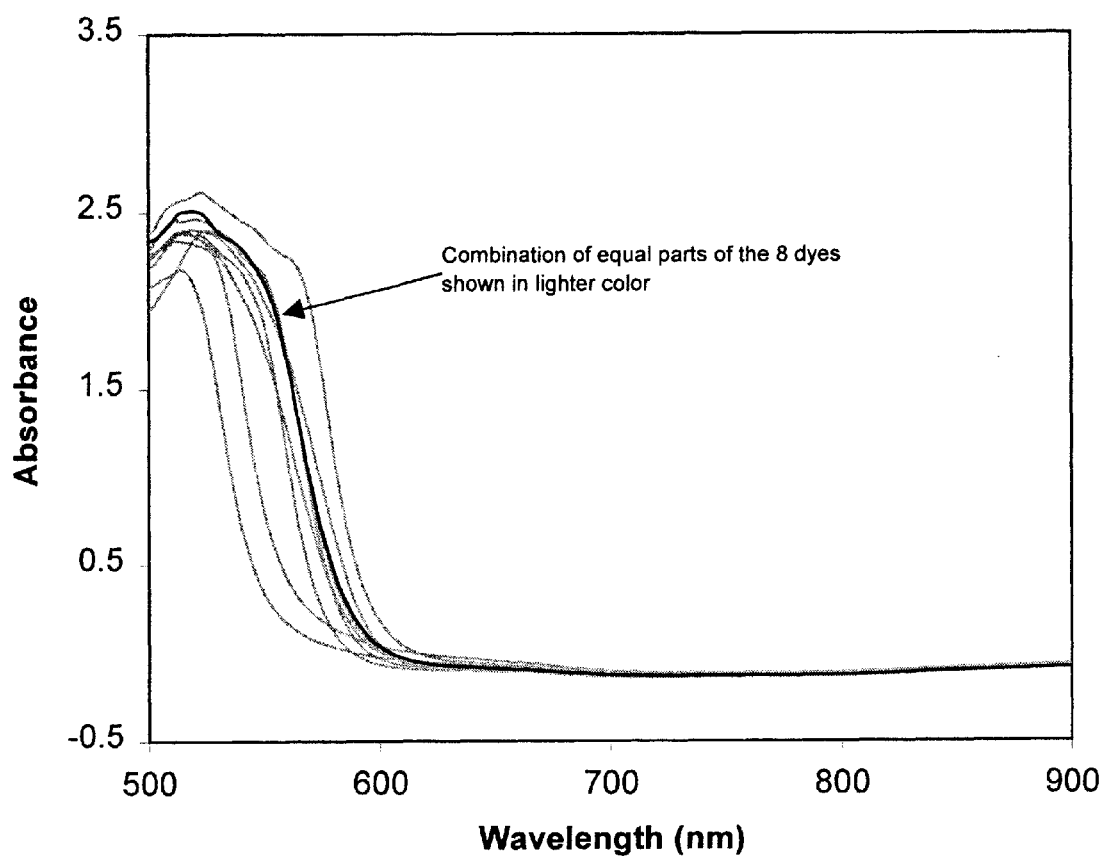

Thus a principal calibration section can be identified which corresponds to the 576 nm–600 nm region of the absorbance spectrum. A QCM can now be selected by screening potential QCM's and selecting those having an absorption spectrum exhibiting a negative slope for a continuous spectral segment of about 5 to 200 mm in the region from 576 nm to 600 nm. As can be seen in FIGS. 7A–C several QCMs have been identified that comply with this requirement and include, but are not limited to, solutions of methyl orange, phenol red, basic fuchsin, acid fuchsin, crystal ponceau, ponceau S, chromotrope 2R, amaranth or any combination thereof.

Further non-limiting examples of QCM for various analytes are provided below. It should be understood that any material with light-scattering and/or light-absorbing characteristics, and that match the criteria as described herein, may be used and is considered within the scope of the invention The QCMs described in the present invention, were designed for calibration algorithms that use the first derivative of absorbance for all specific analytes disclosed except IL and perflurocarbon-based blood substitutes, but other order derivatives of absorbance may also be used. Intralipid™ (IL), is a fat emulsion and may be used to simulate turbidity. It should be understood that when IL measurement is discussed, turbidity measurement is implied, unless indicated otherwise. To those skilled in the art, it is understood that IL is commonly used to simulate turbidity. Calibration algorithms for IL shown in example 5, use both zero and first order derivative of absorbance. Analogous calibration algorithms, to those of IL, may be derived for perfluorocarbon-like blood substitutes, as these calibration algorithms also measure turbidity caused by these analytes (IL or perflurocarbon-like blood substitutes).

As would be obvious to those skilled in the art, a calibration algorithm using the first order derivative of absorbance would yield different prediction values of samples than if using the same wavelengths but the second order derivative of absorbance, in which case the assigned analyte values to a QCM would be different for different primary calibration algorithms. Therefore, QCM's of the present invention can be designed for calibration algorithms that use any order derivative of absorbance. Further, QCM's of the present invention can be designed for calibration algorithms developed by other statistical techniques, for example but not limited to, simple linear regression, PLS or PCA.

Figure 6:
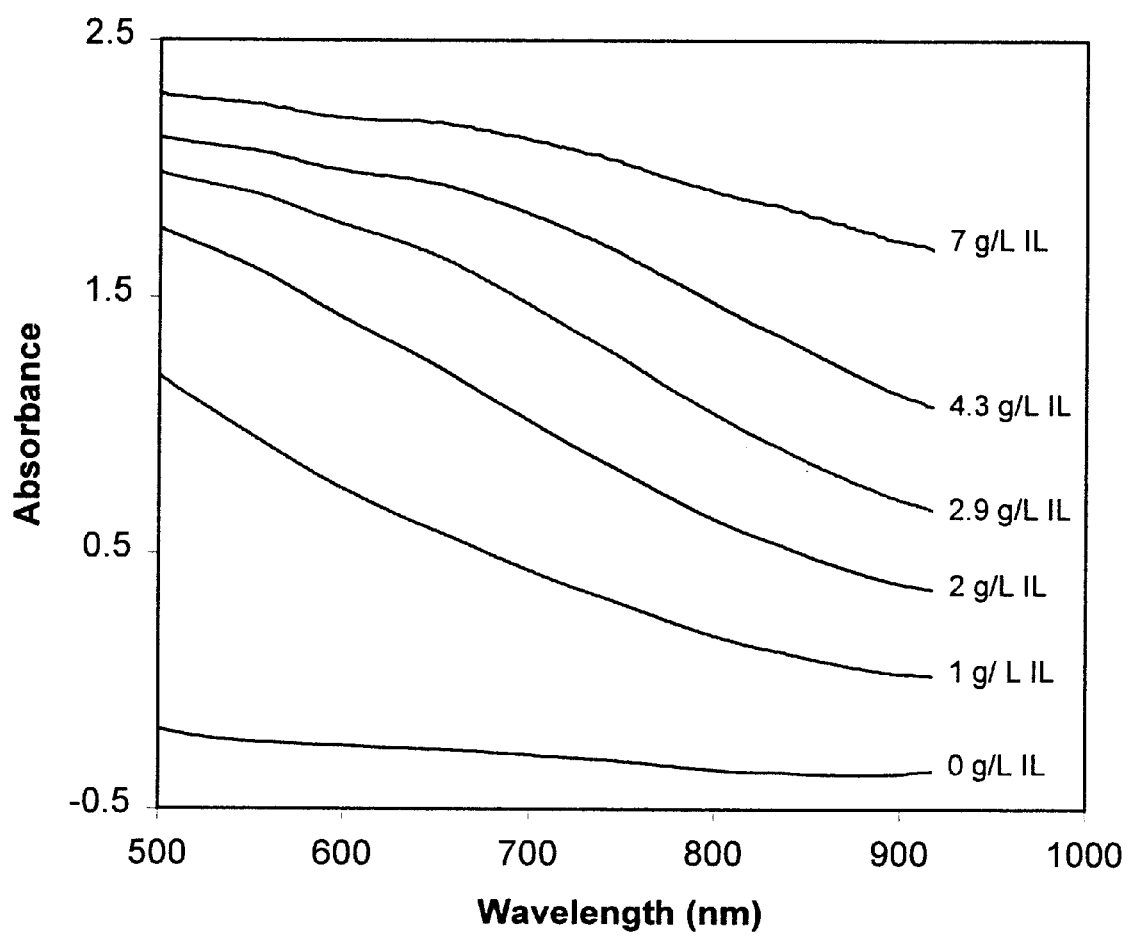
FIG. 6 is a graphic representation of the absorbance spectra of five different concentrations of IL in PBS, and PBS alone.

For IL, when the zero order absorbance is used, any absorbing or light scattering material may be used, provided that the material scatters or absorbs light at the calibration wavelength(s). FIG. 6 shows the absorbance of different concentrations of IL, revealing that any wavelength of the absorbance spectrum can be used for calibration. A preferred primary calibration wavelength may be positioned where there is insignificant absorbance occurring in the sample due to other analytes. The selected wavelength may also be limited by the wavelength range provided by the apparatus. Several non-limiting examples of primary calibration algorithms for IL are given in Example 5, and examples of the wavelengths used may be found in Table 1.

Figure 10:
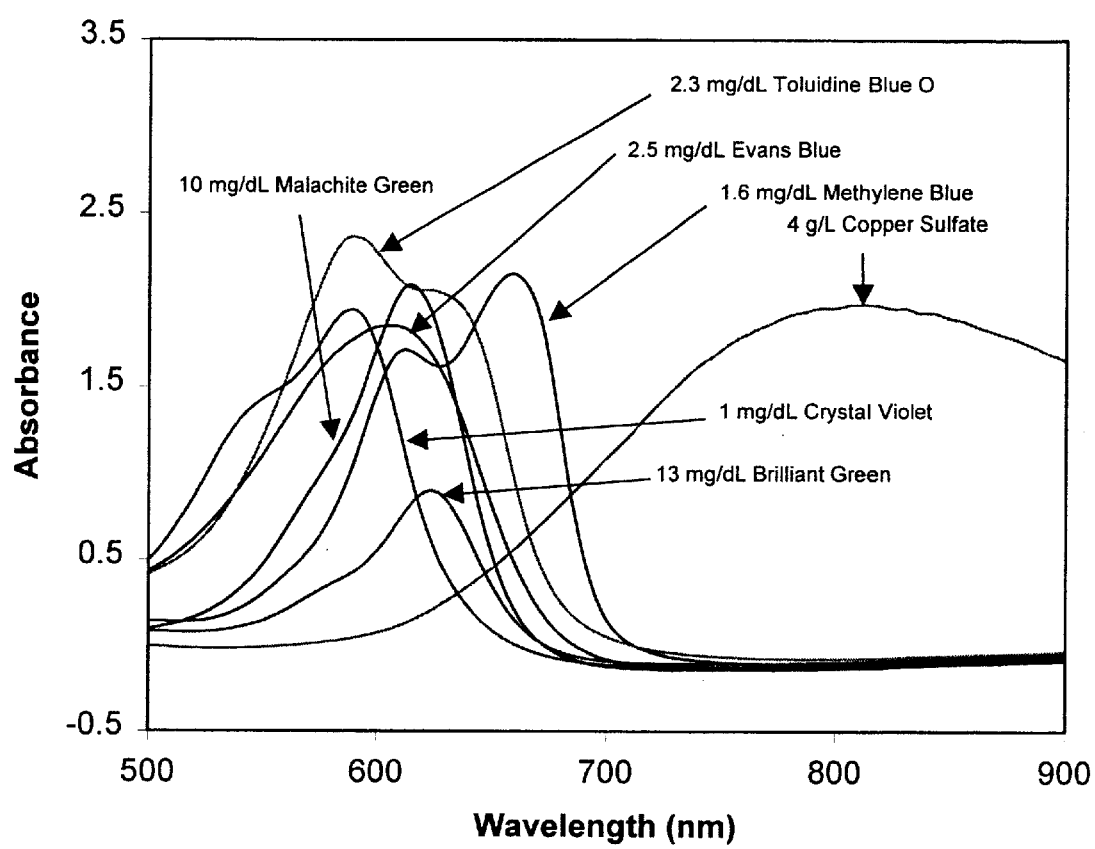
FIG. 10 is a graphic representation of the absorbance spectra of 6 different substances (Malachite green, Brilliant Green, Toluidine blue 0, Evans Blue, Methylene Blue, and Crystal Violet) with negative absorbance slopes between about 600 nm and about 750 nm. Also shown is the absorbance spectrum of copper sulfate with a negative absorbance slope from about 800 nm to about 1100 nm (900 nm actually shown due to wavelength limitation of the apparatus).
Figure 11A:
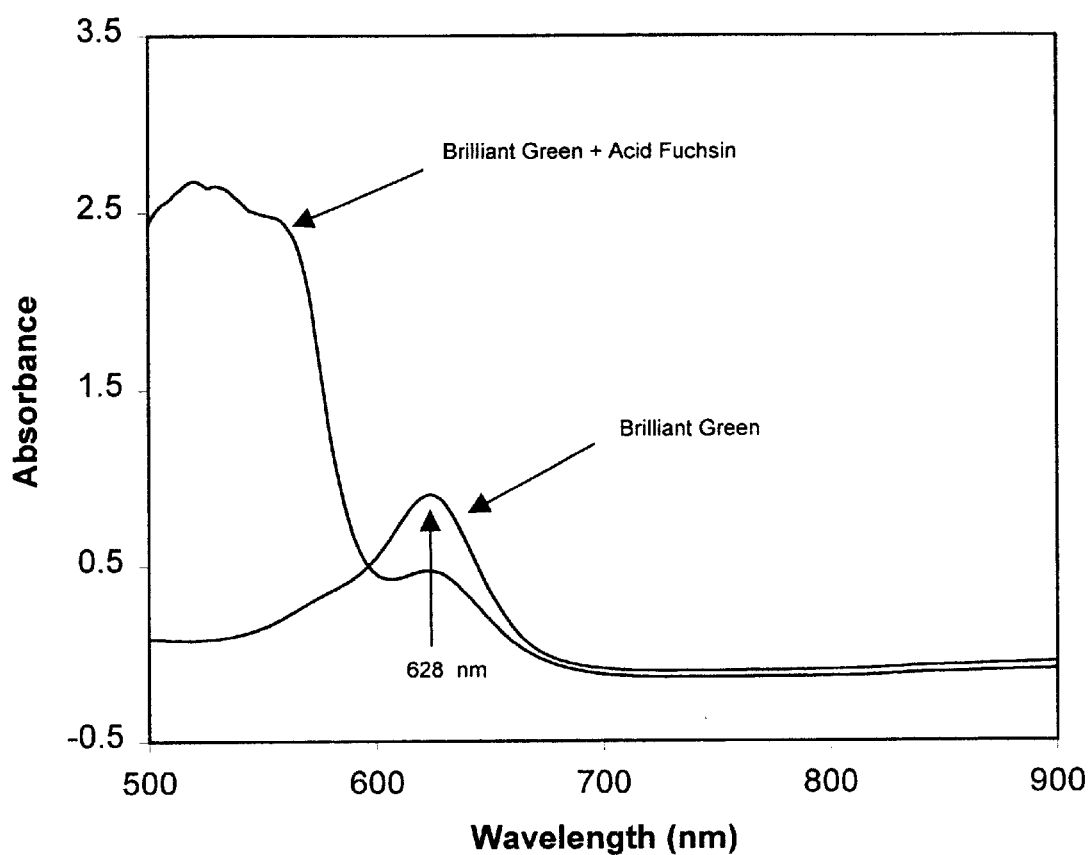
FIGS. 11(A–F) is a graphic representation of the absorbance spectra of the 6 different substances shown in FIG. 10, alone and mixed with Acid Fuchsin (FIGS. A–F).
Figure 11B:
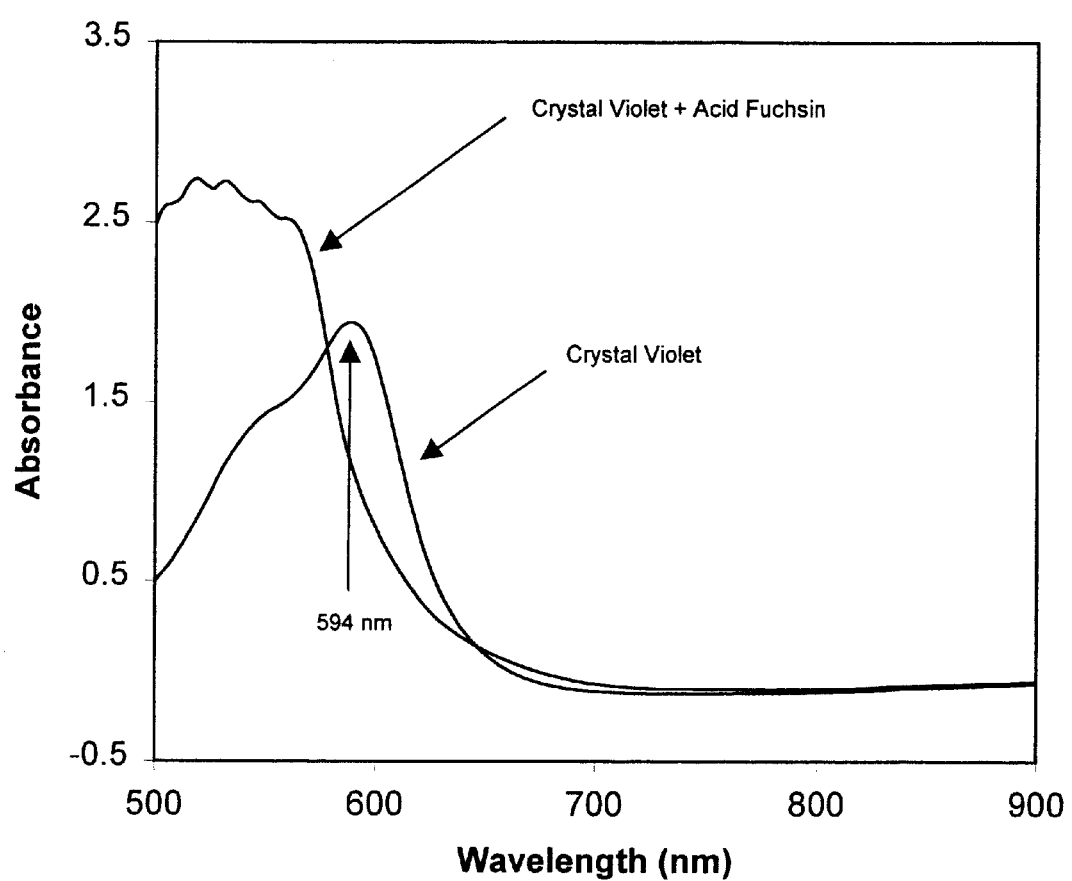
Figure 11E:
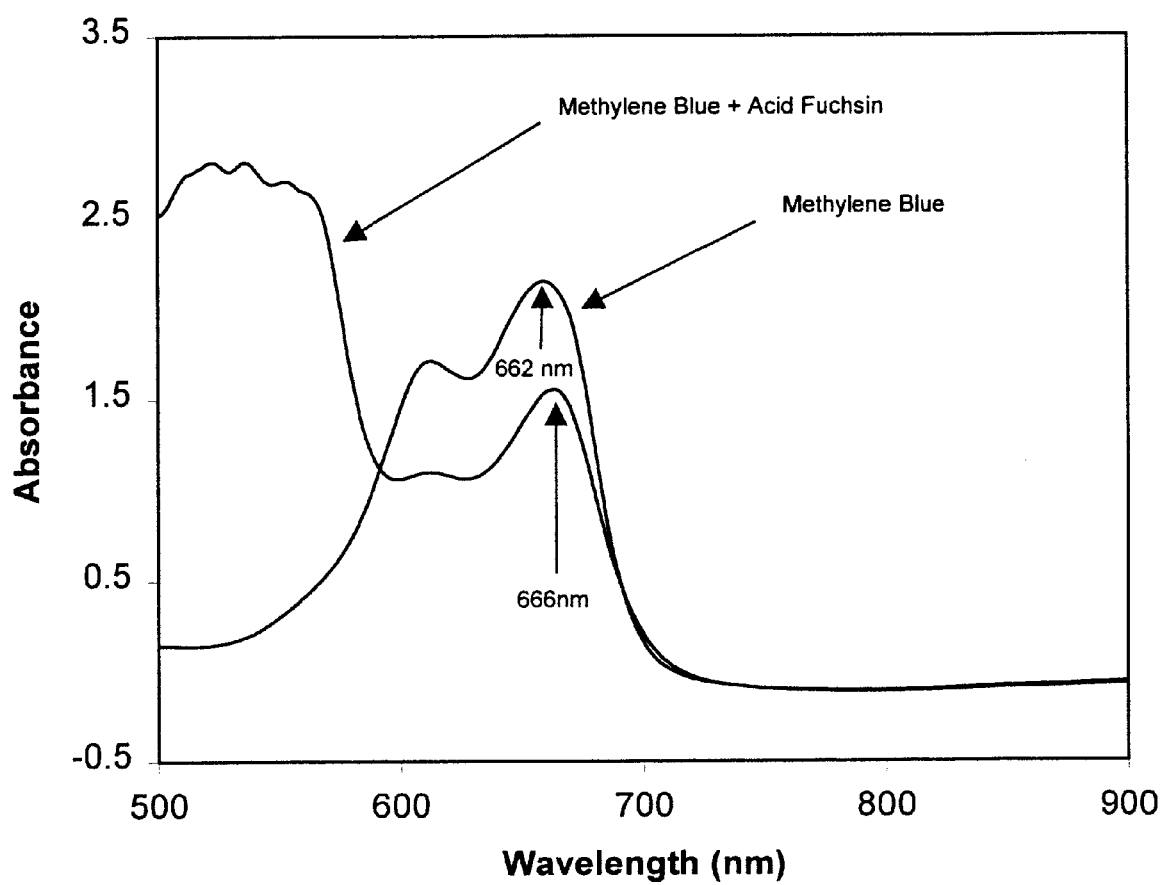
Figure 11F:
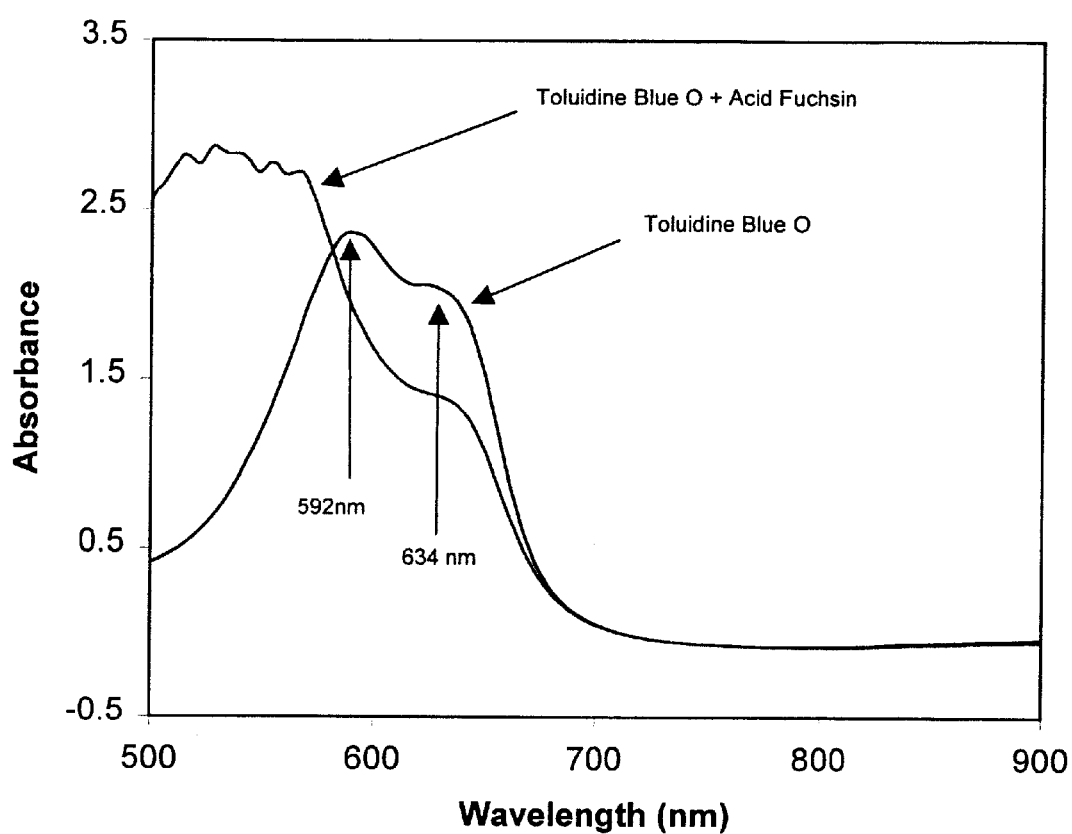
Figure 15:
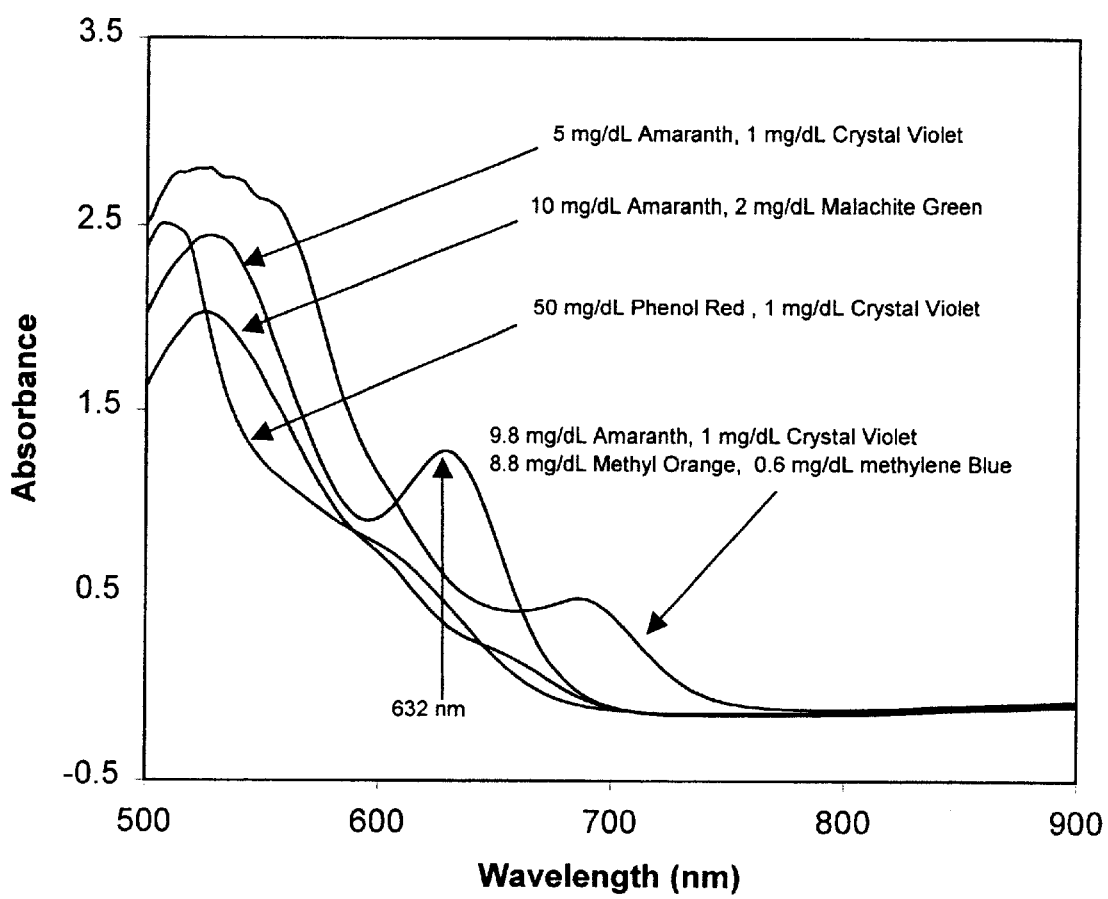
FIG. 15 is a graphic representation of the absorbance spectra of Amaranth plus Crystal Violet, Amaranth plus Malachite Green, and Phenol Red.
Figure 16:
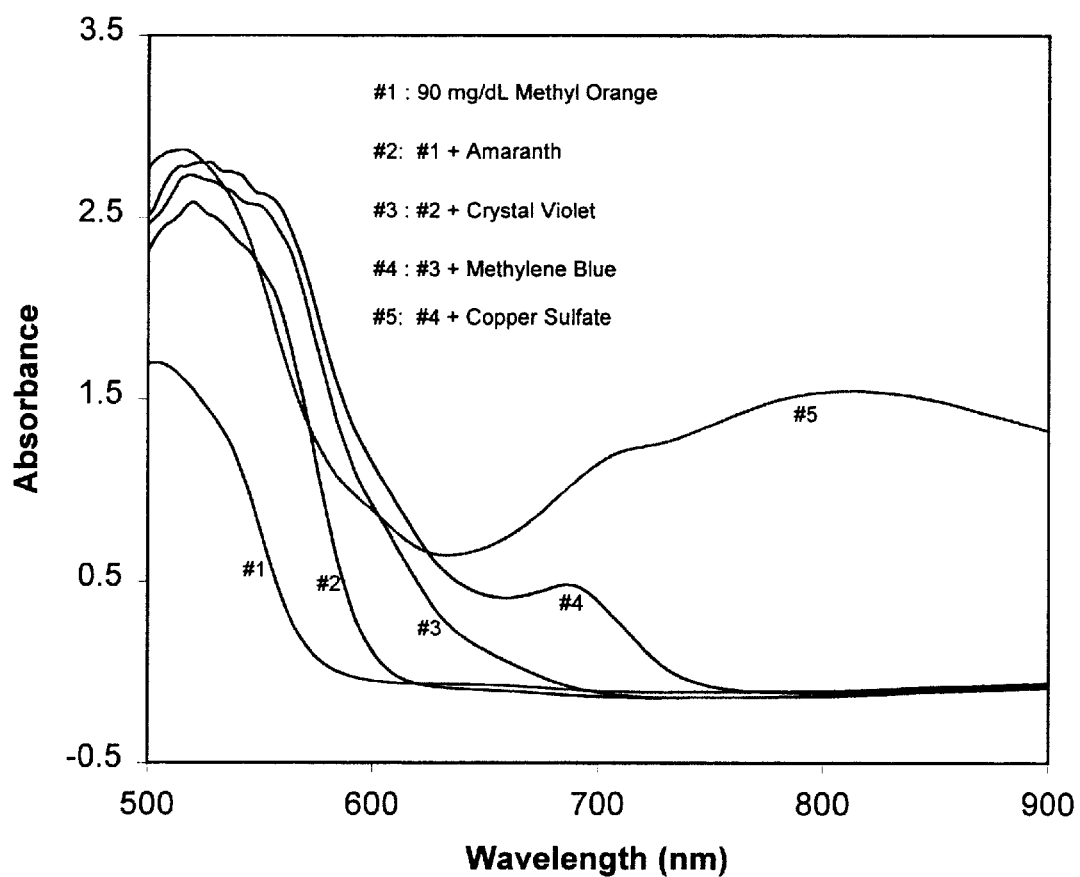
FIG. 16 is a graphic representation of the absorbance spectra of Methyl Orange, and the progressive addition to the Methyl Orange of substances in the order of Amaranth, Crystal Violet, Methylene Blue, and Copper Sulfate.
Figure 17:
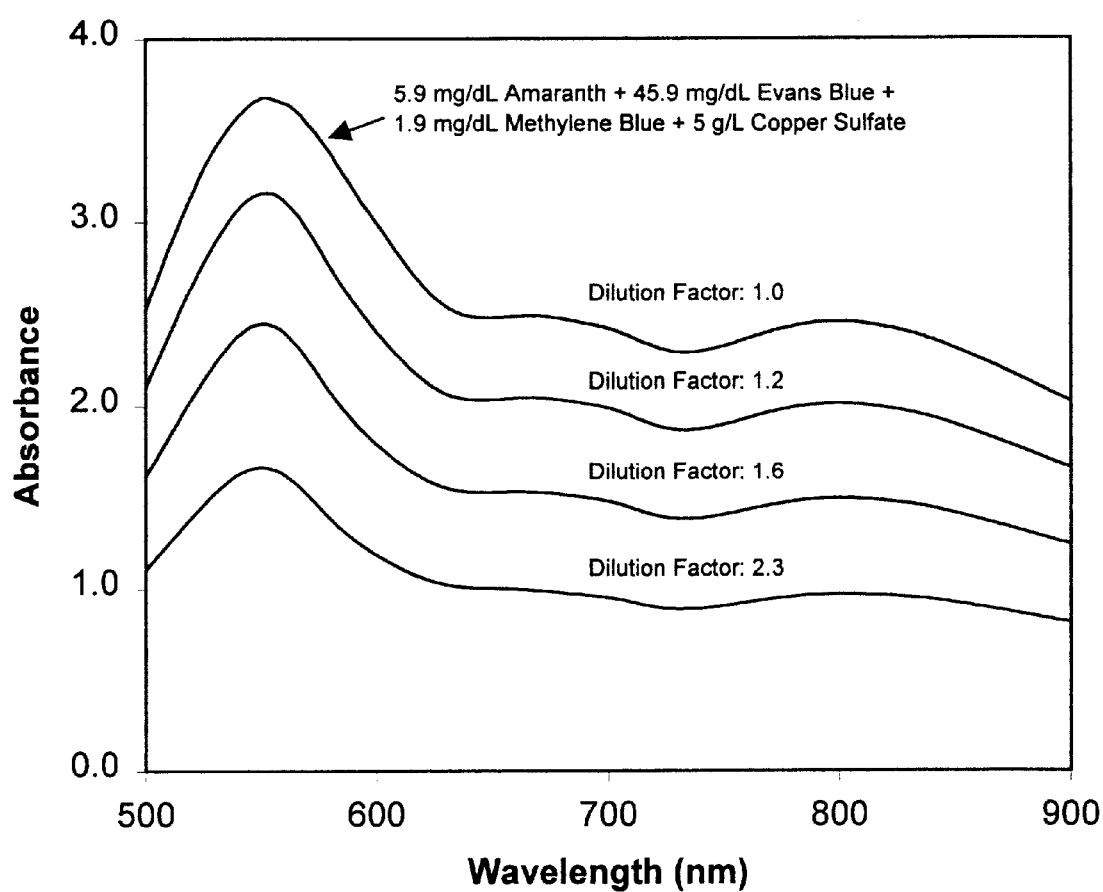
FIG. 17 is a graphic representation of the absorbance spectra of a combination of Amaranth, Evans Blue, Methylene Blue, and Copper Sulfate; four different dilutions are shown.

Since turbidity causes an increase in the "apparent" absorbance, when selecting a QCM used to monitor primary calibration algorithms of analytes that create turbidity for example IL, other lipid emulsions, or perfluorocarbon-like blood substitutes, any substance that produces an absorbance pattern similar to the apparent absorbance of the analyte in the region used by a calibration algorithm, may be used. One such example of a QCM is a non-light-scattering transparent substance, copper sulfate which mimics a simulator of turbidity as expressed in primary calibration algorithms, for example as shown in equations 16–21 in Example 5. Turbidity usually produces absorbance that is inversely proportional to wavelength, as can be seen for IL, in FIG. 6. When the primary calibration algorithm uses raw absorbance at a shorter wavelength, for example 700 nm as shown in equation 16, any other material, including transparent materials (as shown in FIG. 10) or a combination of materials (as shown in FIGS. 15–17) that absorb light at 700 nm (for example), can be used.

In another aspect of the present invention, substances that can be used as QCM's for the calibration algorithms used for the analytes are identified. The substances were chosen based on the absorbance signals provided by the substances, around the principal calibration wavelengths for each analyte. Some of the substances used for illustration are as follows:

1. Methyl Orange
2. Phenol Red
3. Basic Fuchsin
4. Acid Fuchsin
5. Crystal Ponceau
6. Amaranth
7. Ponceau S
8. Chromotrope 2R
9. Malachite green
10. Brilliant Green
11. Toluidine blue O
12. Evans Blue
13. Methylene Blue
14. Crystal Violet
15. Copper sulfate All the substances listed above were dissolved in 0.1 M acetate buffer, but any other buffer at any other pH may be used to obtain the necessary absorbance spectra. For example, phenol red dissolved in water is deep red, but when phenol red is dissolved in 0.1 M acetate buffer, the color is orange.

Non-synthetic substances that can be used for QCM's include total-Hb, oxy-Hb, carboxy-Hb, cyanmet-Hb, Hb-based blood substitutes, a lipid emulsion, perfluorocarbon-like blood substitutes, biliverdin, bilirubin, or a combination thereof However, the use of bilirubin is not preferred due to its light sensitivity.

In developing QCM's, it may be necessary to adjust the shape of the absorbance spectrum to ensure that the QCM exhibits a negative slope of the absorbance spectrum at a principal calibration wavelength of an analyte or as explained earlier for turbidity, the absorbance is high at the primary calibration wavelength. Furthermore, it may be desired to produce a QCM that may be used for monitoring one or more calibration algorithms for one or more different analytes on a spectrophotometric apparatus. Adjusting the shape of the absorbance spectrum by any means is within the scope of this invention. Some examples, which are not to be considered limiting in any manner, of ways to adjust the shape of the section of the absorbance spectrum include: pH adjustment as in the case of phenol red turning from deep red at neutral pH, to orange at acidic pH; mixing two or more substances to give rise to the absorbance spectrum of the two or more materials; or mixing two or more substances, where at least one of the substances can cause an unexpected spectral shift (i.e., non-additive shift in the resultant absorbance spectrum) of the absorbance peak(s) of a second substance that is present. Examples of a substance that may result in an unexpected spectral shift include amaranth (causes spectral shift of several dyes see FIGS. 12A–F, except 12C), polymers such as PVP and PEG, or proteins such as albumin. However, a pH change may also result in an unexpected spectral shift, for example but not limited to, modifying the pH of a phenol red solution. These substances or conditions that cause an unexpected non-additive spectral shift are referred to as spectral modifiers.

QCM for an Indicator of Hemolysis

Figure 5:
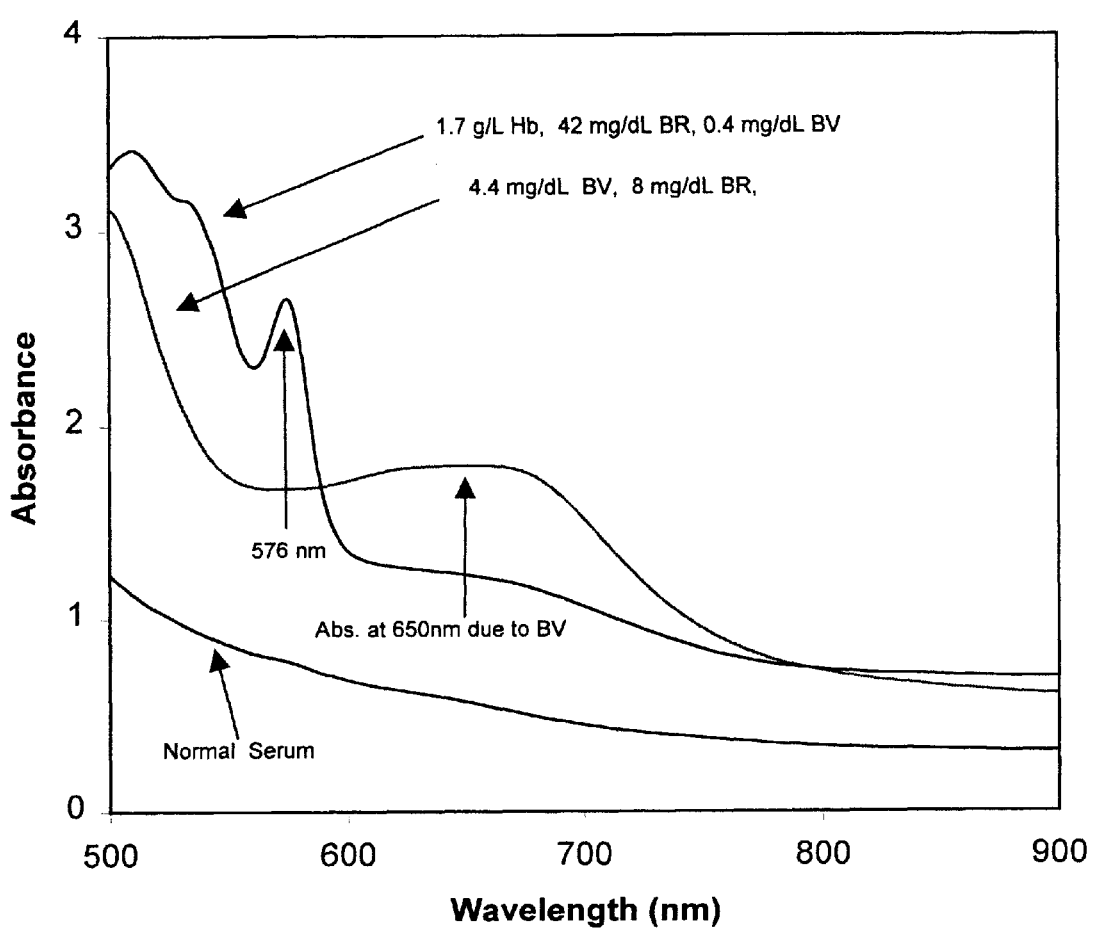
FIG. 5 is a graphic representation of the absorbance spectra of normal serum, mixture of BR and BV, and mixture of Hb, BR and BV.

Hb absorbance spectrum has a negative absorbance slope between about 570 nm and about 670 nm as shown partly in FIGS. 1, 2 & 5. The absorbance maximum for this section of the absorbance spectrum is identified in FIGS. 1 & 5 as 576 nm. The slope and an apparent right spectral shift increases with the concentration of Hb. Hb has other strong absorbing signals, as shown in FIG. 1, but they are usually lost when the Hb concentration is high and/or when turbidity is present. A reliable visible signal is the negative absorbance slope of the 576 nm peak, which can be seen in FIG. 1 for 6.4 g/L Hb and greater, and can also be seen in FIG. 2 for a mixture of 1. 1 g/L Hb+1.4 g/L IL+28 mg/dL BR.

Amaranth is an example of a substance that can be included in a QCM to mimic the absorption of Hb as an indicator of hemolysis. Amaranth concentration can be increased to mimic higher levels of Hb illustrated by high levels of normal human Hb in FIGS. 1 & 4, and it may also be used to mimic Hb-based blood substitutes. Amaranth can mimic the negative slope of the peak of the absorption spectrum of Hb at 576 nm. Amaranth does not have multiple absorbance peaks as Hb (absorbance peaks for Hb are at 544 nm and 576 nm as shown in FIG. 1) and the absorbance maximum of amaranth in the NIR and adjacent visible spectrum is at about 522 nm.

Other substances that may be used to mimic Hb are methyl orange, phenol red, basic fuchsin, acid fuchsin, crystal ponceau, ponceau S, chromotrope 2R, or any combination thereof, as illustrated in FIGS. 7A–C. As would be recognized by one of skill in the art, any other substance with an absorbance maximum of about 500 nm to about 600 nm may be used, depending on the upper limit of the analytical range for the Hb, or Hb-based blood substitute. A non-limiting example of such a substance is crystal violet (shown in FIG. 10) which is deep blue-purplish. Other substances that can be used to mimic Hb, and are within the scope of this invention are total Hb, oxy-Hb, carboxy-Hb, cyanmet-Hb, "total Hb minus met-Hb," and Hb-based blood substitutes.

Furthermore, one or more substances characterized as having a negative slope in their absorption spectrum for a continuous spectral segment of at least 5 nm or more, within the wavelengths of 550 nm and 670 nm, can be used as a mimic of an indicator of hemolysis. In the present invention, an indicator of hemolysis may be selected from total Hb, Oxy-Hb, "total Hb minus met-Hb", or a combination thereof.

U.S. Pat. Nos. 6,268,910 B1, 5,846,492, WO-98/39634, and WO-97/47972 describe calibration algorithms for Hb as an indicator of hemolysis. However, none of these documents indicate the Hb species used as an indicator of hemolysis, or whether the indicator of hemolysis was total Hb. The accuracy of measurement of Hb as an indicator of hemolysis, depends upon three things: 1) The Hb species selected as the indicator of hemolysis; 2) The constituents of each sample in the primary calibration set used to develop the primary calibration algorithm; and 3) The Hb species included in the reference value for the indicator of hemolysis. It should be appreciated by those of skill in the art, that although a primary calibration algorithm is developed for a particular analyte using accurate estimates of the reference values for the analyte, other analytes or substances that are present in a sample may introduce errors in the predicted values for the analyte. This applies particularly to the predicted values of an indicator of hemolysis, where the Hb could exists as several Hb species, and these Hb species need to be accounted for within the primary calibration algorithm. For example, the indicator of hemolysis could be total Hb, which may be measured using standard methods, for example but not limited to, cyanmet-Hb reference method for total Hb measurement (Tietz Textbook of Clinical Chemistry, $2^{nd}$ Ed, 1994, p2020). If the total Hb in the primary calibration samples are not comprised of a suitable variation of the Hb species, the total Hb predicted value for a sample with a high proportion of met-Hb, could be underestimated significantly.

A sample of known oxy-Hb concentration where the Oxy-Hb fraction is about 95% or the total Hb, can be considered to have a total Hb concentration of same value as the oxy-Hb concentration. Similarly, a sample of known total Hb concentration that comprises about 95% oxy-Hb, can be considered to have an oxy-Hb concentration of the same value as the total Hb concentration.

European Patent No. 0132399, U.S. Pat. No. 4,116,336, and WO 87/06343 do not describe any QCM for use as a mimic of an indicator of hemolysis in serum or plasma.

The required accuracy of measurement of the indicator of hemolysis depends on the application of the indicator of hemolysis. Any substance present within a red blood cell (RBC) and not present in the plasma that surrounds the RBC, can be used as an indicator of hemolysis, as hemolysis liberates substances contained within the RBC's into the plasma or serum. Hb is an example of a substance contained inside the RBC's, and is only present in serum and plasma if hemolysis has occurred. Hemolysis can occur in vitro, for example if the sample was handled roughly, or hemolysis can occur in vivo, for example in patients with fragile RBC membrane or in patients with prosthetic heart valves. Therefore, three reasons for measuring an indicator of hemolysis are: 1) To know the full extent of a combination of in vivo and in vitro hemolysis; 2) To know the true level of hemolysis for the sake of understanding by how much the concentration of a substance like potassium can become artificially elevated in serum or plasma, due to in vitro hemolysis (potassium is another example of a substance released from hemolyzed RBC's, as its concentration within the RBC's is about 25 times that of plasma); and 3) To determine the increase in absorbance of the serum or plasma due to the release of hemoglobin, in an effort to understand how and to what extent the artificially increased absorbance due to Hb, affects spectrophotometric assays for other analytes.

Figure 3:
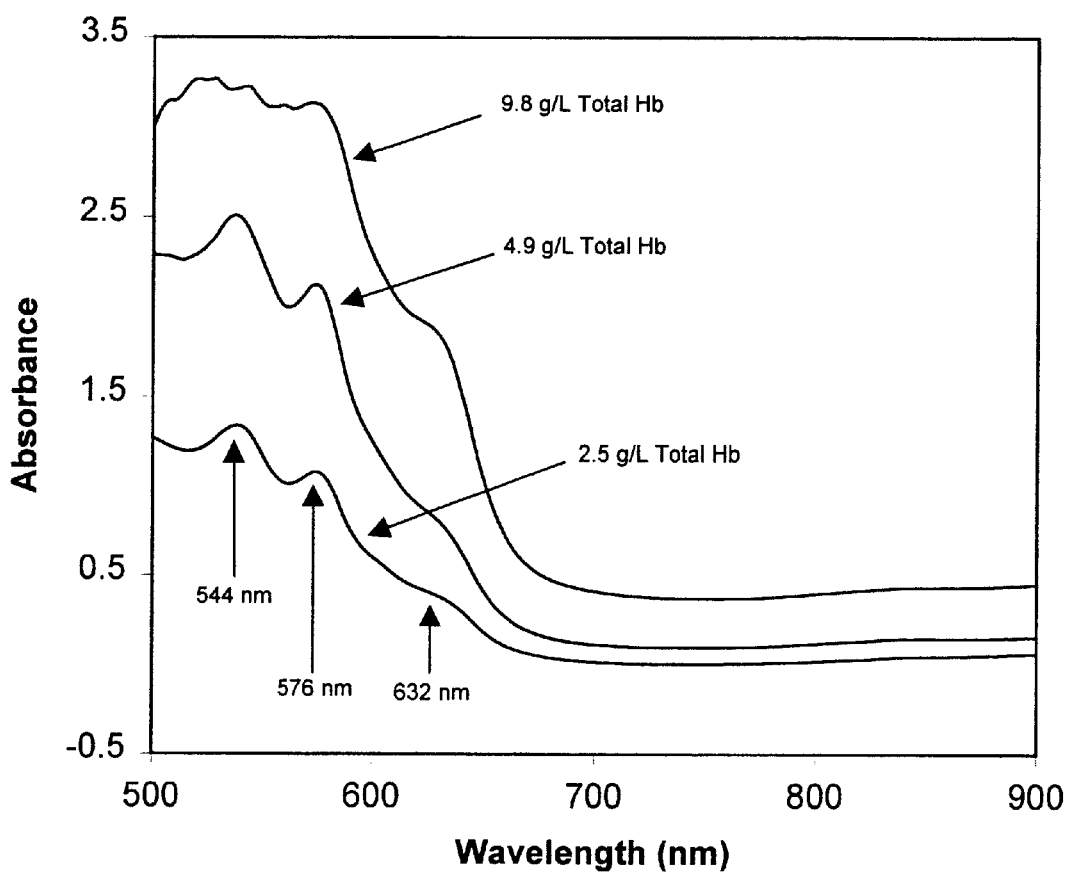
FIG. 3 is a graphic representation of the absorbance spectra of three different concentrations of total Hb, from the same pool, which was allowed to become partly oxidized to produce met-Hb.

Total Hb is a sensitive indicator of hemolysis, and provides a good estimate of the extent of hemolysis. The composition of normal Hb in arterial blood is about 95% oxy-Hb, about 1% met-Hb, about 2% carboxy-Hb, and about 2% deoxy-Hb, measured in an arterial blood sample by co-oximetry. The art of co-oximetry is well known and deals with the measurement of hemoglobin species in whole blood: oxy-Hb, deoxy-Hb (or reduced-Hb), met-Hb, and carboxy-Hb. The proportion of the Hb species seen in most serum and plasma samples with hemolysis, is similar to that described for arterial blood, even though the serum and plasma is usually obtained from a venous blood sample. The percentage of oxy-Hb of total Hb, called the Hb oxygen saturation, is usually much higher in an arterial blood sample, compared to that of a venous blood sample, because of the increase in deoxy-Hb in venous blood. The increase level of oxy-Hb in a venous sample (serum or plasma) is due to exposure of the sample to air, which contains 20% oxygen (i.e., a partial pressure of oxygen of 152 mm Hg, 20% of 760 mm Hg). Therefore, oxy-Hb is another sensitive indicator of hemolysis, especially in blood samples with normal Hb species. FIG. 1 shows normal Hb as well as 10 g/L met-Hb; the met-Hb shown is reconstituted lyophilized human met-Hb obtained from Sigma. An increase in met-Hb within the sample is shown in FIG. 3, but the fraction of the total Hb that is in the met-Hb form is unknown. The met-Hb shown in FIG. 3 was created by spontaneous oxidation of Hb. The blood donor used to provide the hemolysate with absorbance spectra shown in both FIGS. 1 and 3 is the same, and the absorbance spectra of the fresh hemolysate, made on different days, were indistinguishable.

The absorbance spectra for oxy-Hb, deoxy-Hb and carboxy-Hb are very similar in the region from about 576 nm to 700 nm, compared with absorbance of met-Hb, (which is much lower) in the same wavelength region. Met-Hb also exhibits a characteristic absorbance peak at about 632 nm. Therefore, if a calibration algorithm for total Hb is developed, for example, using reference values that are estimates of total Hb, comprising about 95% oxy-Hb as shown in FIG. 1, large quantities of deoxy-Hb and carboxy-Hb in a sample will be included in the measurement of total Hb. However, the absorbance of met-Hb is low in the 576 nm to 700 nm region, which could result in a significant underestimation of total Hb compared to the reference measurement of the total Hb. In this case, the predicted values derived from the calibration for total Hb as the indicator of hemolysis, would be more reflective or the "total Hb minus met-Hb." Therefore, in this case, the indicator of hemolysis may be more appropriately called, "total Hb minus met-Hb." In the example where the oxy-Hb is about 95% of all the Hb species, the reference values of oxy-Hb can be used. The predicted values of oxy-Hb will not be significantly affected by met-Hb, if affected at all, but the predicted values of oxy-Hb will not be a reliable estimate of hemolysis, since most of the met-Hb will not be measured.

Therefore, an aspect of one of the methods of the present invention is to overcome the underestimation of total Hb in the presence of large quantities of met-Hb as follows:

1) Add met-Hb to the primary calibration set, and include met-Hb in the reference values of total Hb for the development of a calibration algorithm; or
2) Add met-Hb in the primary calibration set, and do not include the met-Hb in the reference value for "Hb" during development of the primary calibration algorithm.

In the second approach, the calibration algorithm will predict "total Hb minus met-Hb".

In another aspect of the present invention, a separate primary calibration algorithm is developed for met-Hb. This calibration algorithm may be used for determination of met-Hb in a sample and it can be used to flag samples with met-Hb that exceed a predetermined value. The predicted met-Hb may also be added to the "total Hb minus met-Hb" described above, for a determination of total Hb. This method is an accurate method of obtaining total Hb in the presence of met-Hb. In a preferred embodiment for developing a primary calibration algorithm for "total Hb minus met-Hb", the samples in the primary calibration set should contain various amounts of oxy-Hb, deoxy-Hb and carboxy-Hb, and the amounts of each of the three species should be summed to produce the concentration of total Hb, which is actually "total Hb minus met-HB". The name of the substance used as an indicator of hemolysis is usually the same as the substance or substances included in the reference values. However, it should be understood that the actual substance or substances included in the reference values depend on the composition of the primary calibrators.

In yet another aspect of the present invention, the indicator of hemolysis is oxy-Hb, and a corrected total Hb value can be obtained by adding the predicted values for oxy-Hb and met-Hb. To those skilled in the art, it will be understood that a significant proportion of deoxy-Hb and/or carboxy-Hb, if present in a sample, could be measured as oxy-Hb.

As noted above, about 95% of the Hb in a hemolyzed sample is usually in the oxy-Hb state, unless the blood donor was recently exposed to carbon monoxide or the person suffers from methemoglobinemia. Exposure to carbon monoxide (mainly due to smoke inhalation) causes an elevation of carboxy-Hb, and methemoglobinemia causes an elevation of met-Hb. Oxidation of the iron in the heme moiety of Hb molecules, is a normal process that occurs in vivo; enzymes are continually at work reversing the process and thus preventing the accumulation of met-Hb. Methemoglobinemia is a condition of people that lack enzymes required to reverse this oxidation process. Lack of these enzymes also cause spontaneous oxidation of Hb to met-Hb in hemolyzed serum or plasma over time, causing the sample to darken in the color. FIG. 3 shows how the absorbance spectra of a hemolyzed sample changes as it ages. The absorbance peak at about 632 nm that accompanies the darkening of color indicates a conversion of Hb to met-Hb. Accumulation of met-Hb could also occur in serum or plasma of patients transfused with Hb-based blood substitutes. A calibration algorithm for met-Hb in hemolyzed serum or plasma samples or in a serum or plasma sample from a patient transfused with Hb-based blood substitutes can therefore be developed, preferably using the negative absorbance slope of the peak with an absorbance maximum at about 630 nm. Example 6 (Equation 22) gives an example of a primary calibration algorithm for met-Hb, which uses 645 nm as the principal calibration wavelength.

The method of measuring met-Hb according to the present invention is different from the method used by cooximetry, as cooximetry determines the measurement of hemoglobin species in whole blood. The measurement of met-Hb as described herein, is used in the measurement of an indicator of hemolysis in serum, plasma, urine, cerebrospinal fluid, lymphatic fluid and synovial fluid, for measuring the oxidation of Hb into met-Hb, and also for measuring the oxidation of Hb-based blood substitutes into their met-Hb form.

The absorbance spectrum of hemoglobin-based blood substitutes is very similar to natural Hb as shown in FIG. 1. The above analysis for Hb can therefore be applied to Hb-based blood substitutes. More specifically, one or more substances with a negative slope in the absorption spectrum for a continuous spectral segment of at least 5 nm, within the wavelengths of 550 nm and 700 nm, can be used as a mimic of hemoglobin-based blood substitutes.

When Hb is converted to cyanmethemoglobin (cyanmet-Hb), the 544 nm and 576 nm absorbance peaks of Hb merge into a broad peak with an absorbance maximum between these two maxima. Therefore, cyanmethemoglobin is a good substance that can be used as a mimic of an indicator of hemolysis or Hb-based blood substitute. Since Hb is oxidized to met-Hb as the first of two steps in producing cyanmethemoglobin, oxidation of Hb to met-Hb is not an issue with cyanmethemoglobin.

The combination of cyanmethemoglobin or Hb-based blood substitutes with a lipid emulsion, for example IL, or perfluorocarbon-like blood substitutes may be used to mimic Hb, turbidity, blood substitutes, or a combination thereof. The combination of one or more of the above may also be used to mimic additional analytes. The product may be autoclaved for sterility, or any suitable preservative may be added. Storage may be at any suitable temperature.

QCM for met-Hb

The absorbance spectrum for met-Hb is shown in FIG. 1. The absorbance spectra for three different concentrations of total Hb that was allowed to age, is shown in FIG. 3. As Hb is allowed to age, the Hb oxidizes to met-Hb spontaneously. The appearance of the absorbance peak at 632 nm is characteristic of met-Hb formation. Therefore, one or more substances with a negative absorbance slope for a continuous spectral segment of at least 5 nm or more, within the wavelengths of 610 nm and 690 nm, can be used as a mimic of met-Hb. Non-limiting examples of substances that can be used to mimic met-Hb include brilliant green, crystal violet, evans blue, malachite green, and toluidine blue O. The absorbance spectra of these substances are shown in FIG. 10.

The absorbance spectra of brilliant green, crystal violet, evans blue, malachite green, and toluidine blue O in composition with acid fuchsin, amaranth, methyl orange and phenol red, are shown in FIGS. 11, 12, 13 and 14, respectively. Each of FIGS. 11, 12, 13 and 14 contains FIGS. A to F representing brilliant green, crystal violet, evans blue, malachite green, methylene blue and toluidine blue 0, respectively. The addition of amaranth to brilliant green, crystal violet, malachite green, and toluidine blue O causes significant right shift (towards longer wavelengths) in these substances. No spectral shift was noted in compositions comprising amaranth and evans blue. Furthermore, no spectral shift is observed for brilliant green, crystal violet, evans blue, malachite green, and toluidine blue O in compositions comprising acid fuchsin, methyl orange or phenol red, and brilliant green, crystal violet, evans blue, malachite green, and toluidine blue O. These substances can be used alone or in combination with one or more substances, in order to mimic met-Hb alone, or with one or more of BR, an indicator of hemolysis, for example total Hb, oxy-Hb, or "total minus met-Hb," Hb-based blood substitutes, a simulator of turbidity, for example but not limited to IL, perfluorocarbon-like blood substitutes and non-light-scattering transparent substances (like copper sulfate), MB, and BV. The spectral shift caused by amaranth can be used to fine tune the negative absorbance slope of the substances used to mimic met-Hb.

QCM for BR

BR absorbance spectrum has a negative absorbance slope between about 500 nm and about 600 nm as shown partly in FIGS. 2 & 5. The slope and an apparent right spectral shift increases with the concentration of BR. BR has an absorbance maximum of about 454 nm. Therefore, the principal calibration wavelength could be from about 450 nm to about 600 nm.

Calibration for BR is very similar to calibration for Hb, except that the slope of the BR absorption spectrum occurs at shorter wavelengths. Equation 11 (Example 4) shows that the principal calibration wavelength for BR is most likely 524 nm, which is shorter than all the primary calibration wavelengths used for Hb. Table 1 gives several examples of primary calibration wavelengths that can be used for BR, where the first wavelength in each row (each row represents a different calibration algorithm or equation) is most likely the principal calibration wavelength for BR.

One or more substances with a negative absorbance slope for a continuous spectral segment of at least 5 nm or more, within the wavelengths of 500 nm and 600 nm, can be used as a mimic of bilirubin.

By comparing the absorbance spectrum of BR (FIG. 2) to several non-limiting examples of substances, as shown in FIGS. 7A–B, substances may be selected that exhibit overlapping spectra with the absorbance spectrum of BR. Examples of suitable substances include phenol red (at acidic pH) and methyl orange. However, it is to be understood that other substances that may be used to mimic an indicator of hemolysis as identified above (see QCM for an indicator of hemolysis), may also be used, depending on the principal calibration wavelengths used for BR. Therefore, the same substance can be used to mimic an indicator of hemolysis alone, or BR alone, or both an indicator of hemolysis and BR. Also, one or more substances can be used to mimic an indicator of hemolysis alone, or BR alone, or both an indicator of hemolysis and BR. This is best illustrated by FIG. 7C that shows the absorbance spectra of 8 substances that may used singly to mimic an indicator of hemolysis alone, or BR alone, or both an indicator of hemolysis and BR, or that may be combined to produce a composition exhibiting properties that are similar to each of the 8 substances, and that may mimic an indicator of hemolysis alone, or BR alone, or both an indicator of hemolysis and BR.

Figure 8:
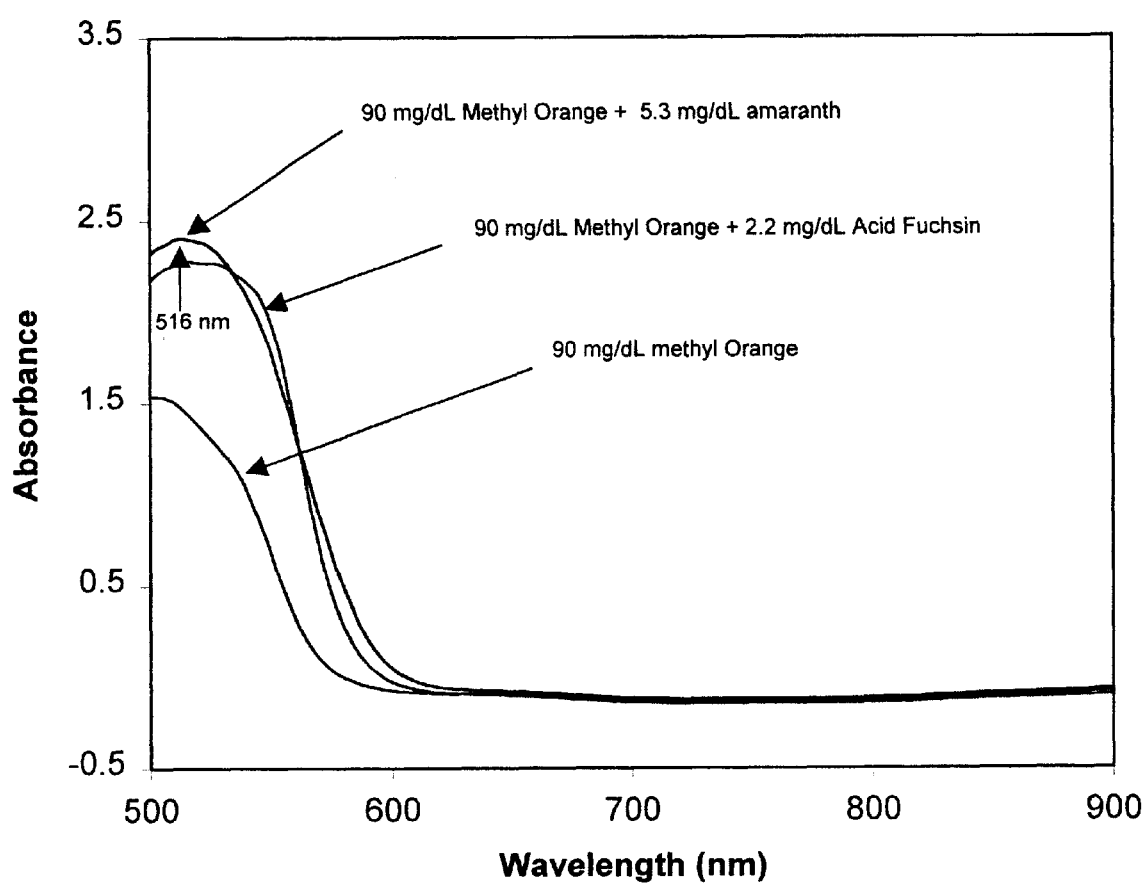
FIG. 8 is a graphic representation of the absorbance spectra of Methyl Orange alone, Methyl Orange plus Acid Fuchsin, and Methyl Orange plus Amaranth.
Figure 9:
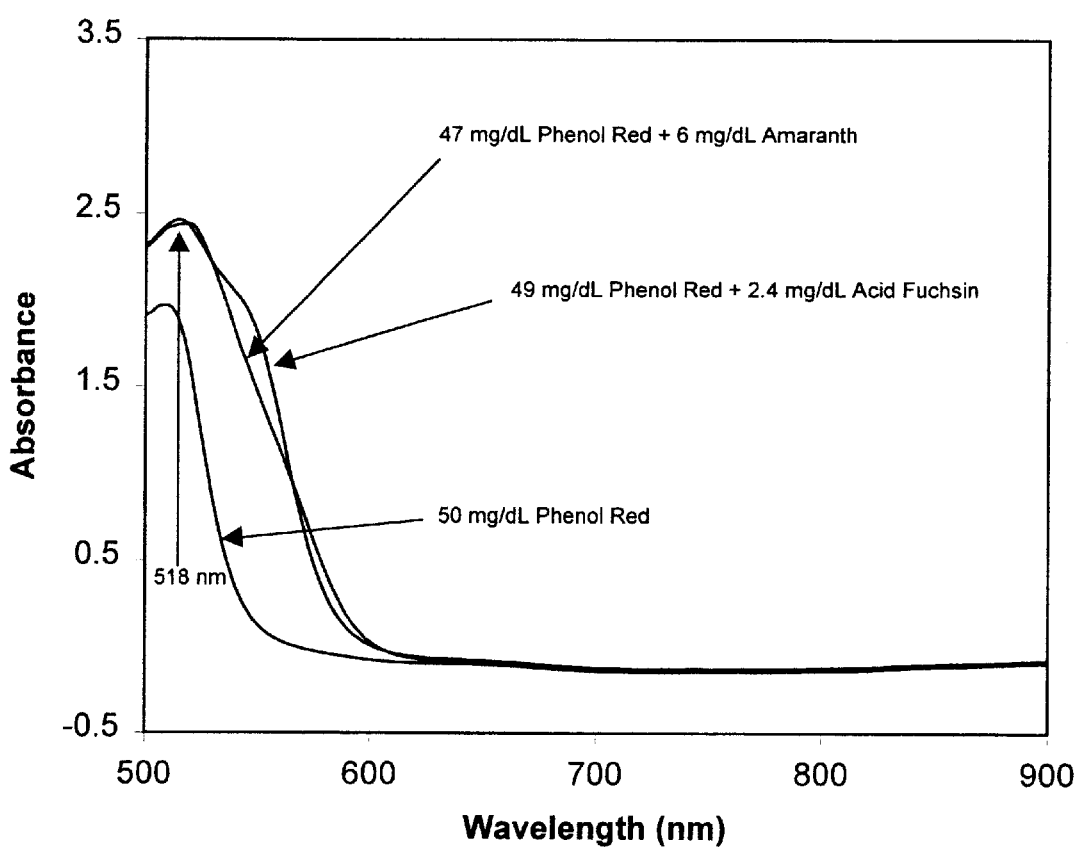
FIG. 9 is a graphic representation of the absorbance spectra of Phenol Red alone, Phenol Red plus Acid Fuchsin, and Phenol Red plus Amaranth.

Examples of other substances that can be combined to mimic both BR and an indicator of hemolysis are shown in FIGS. 8, 9 & 15. FIG. 8 shows a combination of methyl orange and amaranth and FIG. 9 shows a combination of phenol red and amaranth, and phenol red and acid fuchsin that can mimic both BR and an indicator of hemolysis. However, it is to be understood that any substance (or more than one substance), with an absorbance maximum between about 450 nm and about 520 nm, may be combined with another substance (or more than one other substance), with an absorbance maximum between about 500–600 nm, to mimic an indicator of hemolysis alone, or BR alone, or both an indicator of hemolysis and BR, provided that composition of substances is characterized as having a negative absorbance slope for a continuous spectral segment of at least 5 nm or more, within the wavelengths of about 450 nm and about 670 nm. These substances can be used alone or in combination with one or more substances, in order to mimic BR alone, or optionally in addition to one or more of an indicator of hemolysis, for example total Hb, oxy-Hb or "total Hb minus met-Hb,", Hb-based blood substitutes, a simulator of turbidity, for example but not limited to IL, perfluorocarbon-like blood substitutes, and non-light-scattering substances (like copper sulfate), MB, and BV. The spectral shift caused by amaranth can be used to fine-tune the negative absorbance slope of the substances used to mimic met-Hb.

QCM for MB

Figure 4:
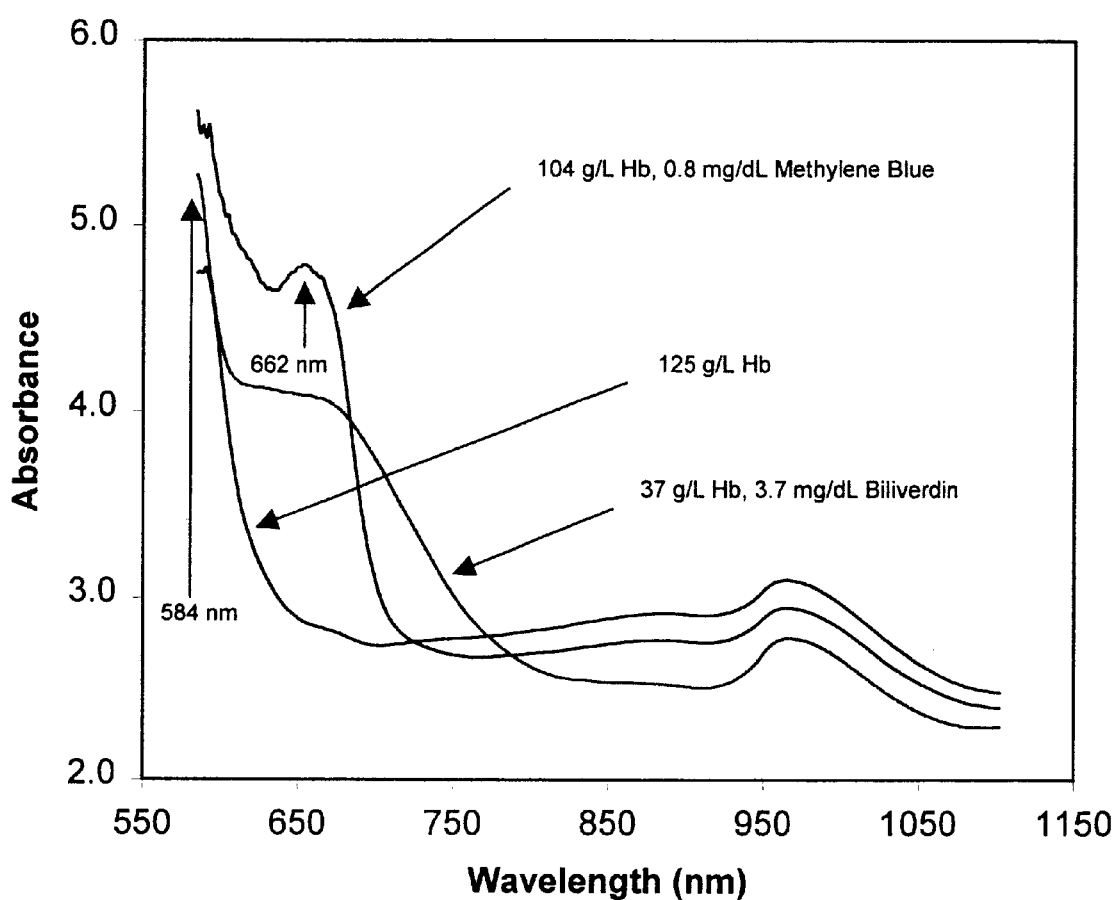
FIG. 4 is a graphic representation of the absorbance spectra obtained on a different apparatus, of 125 g/L Hb, 104 g/L Hb plus 0.8 mg/dL MB, and 37 g/L Hb plus 3.7 mg/dL BV.

The absorbance spectrum of MB is shown in FIGS. 4, 10, 11E, 12E, 13E and 14E. MB absorbance spectrum has a negative absorbance slope between about 650 nm and about 750 nm as shown partly in FIG. 4. The absorbance maximum for this section of the absorbance spectrum is identified in FIG. 4 & 11E (also 12E, 13E and 14E) as 662nm. The second absorbance maximum shown in FIG. 11E cannot be seen in FIG. 4 due to the presence of 104 g/L Hb, as identified in FIG. 4. The slope and an apparent right spectral shift increases with the concentration of MB. In FIG. 4, the negative absorbance slope of MB at the right side of the 662 nm absorbance peak is exposed, while the left side is hidden due to the presence of other compounds for example BR, Hb, turbidity or a combination thereof.

Any one or more substances with a negative absorbance slope for a continuous spectral segment of at least 5 nm or more, within the wavelengths of 650 nm and 750 nm, can be used as a mimic of MB. Examples of one or more substances that may be used as a QCM to mimic MB include brilliant green, crystal violet, evans blue, malachite green, methylene blue and toluidine blue O. As mentioned above for met-Hb, the spectral shift caused by amaranth can be used to fine-tune the negative absorbance slope. These substances can be used alone or in combination with one or more substances, in order to mimic MB alone, or optionally in addition to one or more of BR, an indicator of hemolysis, met-Hb, Hb-based blood substitutes, BV, a simulator of turbidity and perfluorocarbon-like blood substitutes.

Figure 12A:
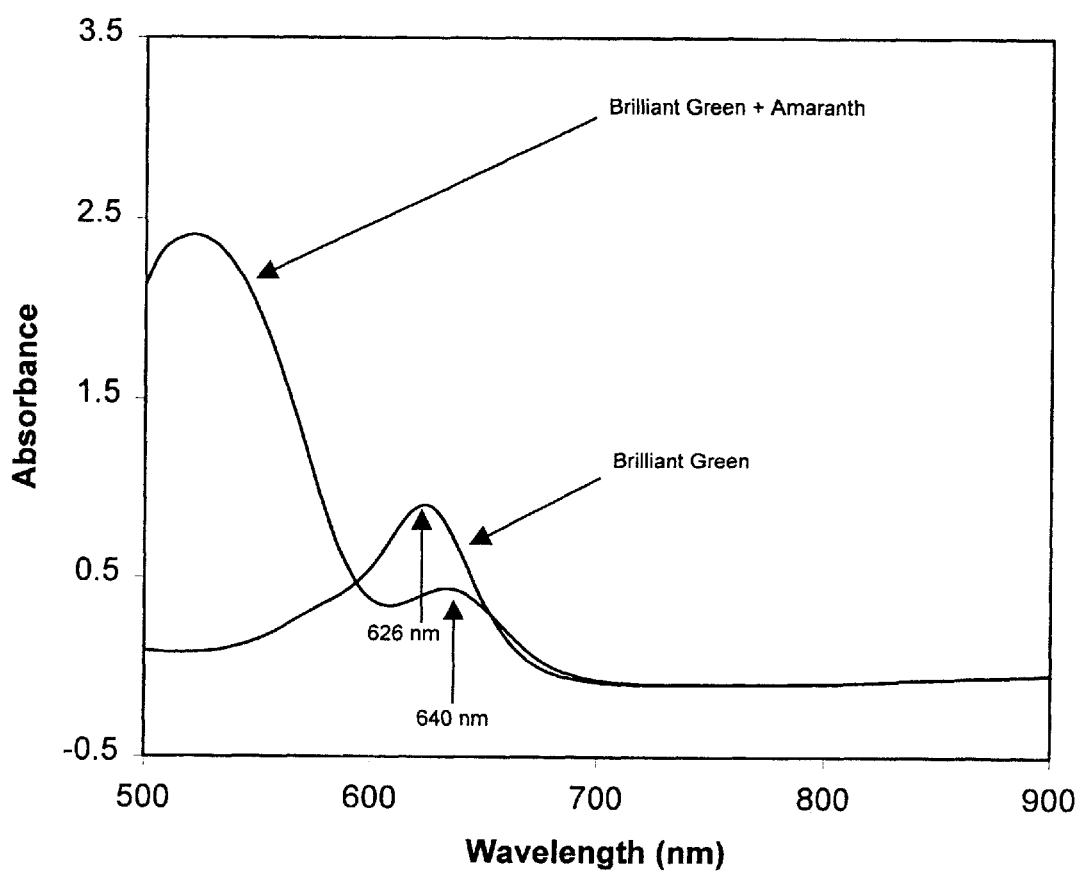
FIGS. 12(A–F) is a graphic representation of the absorbance spectra of the 6 different substances shown in FIG. 10, alone and mixed with Amaranth (FIGS. A–F).
Figure 12B:
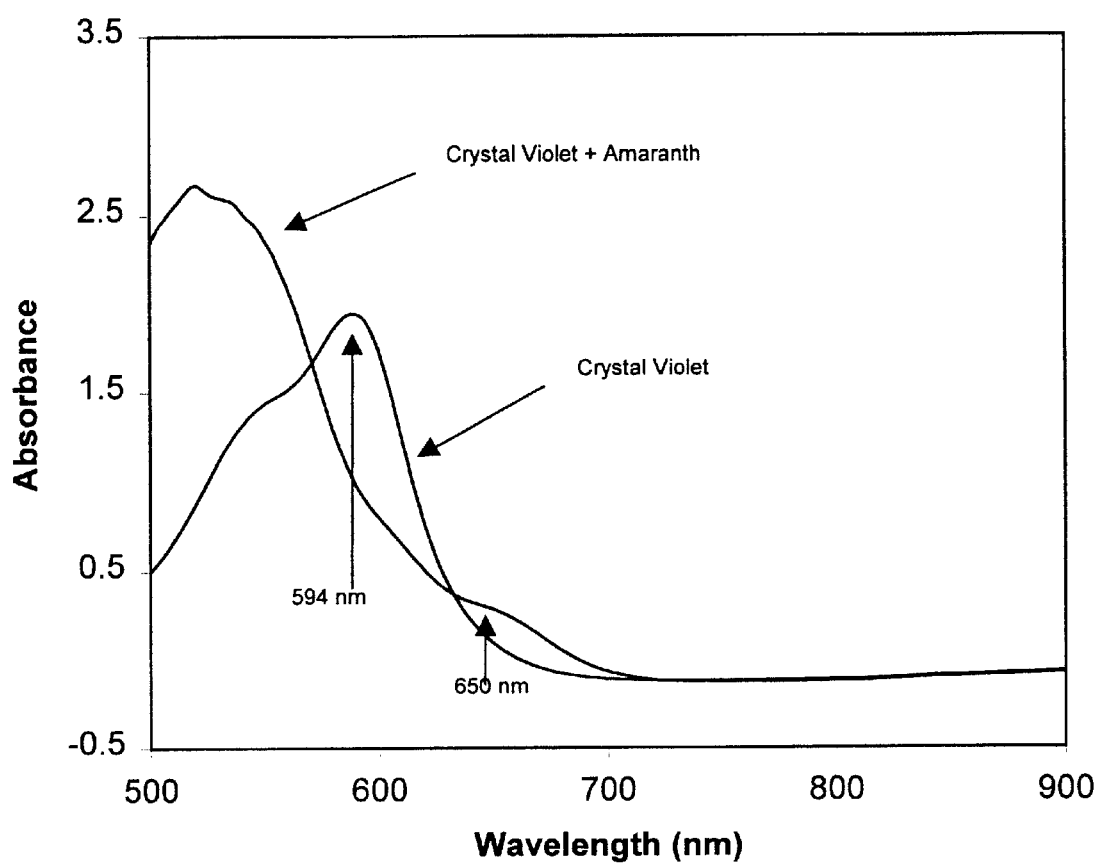
Figure 12C:
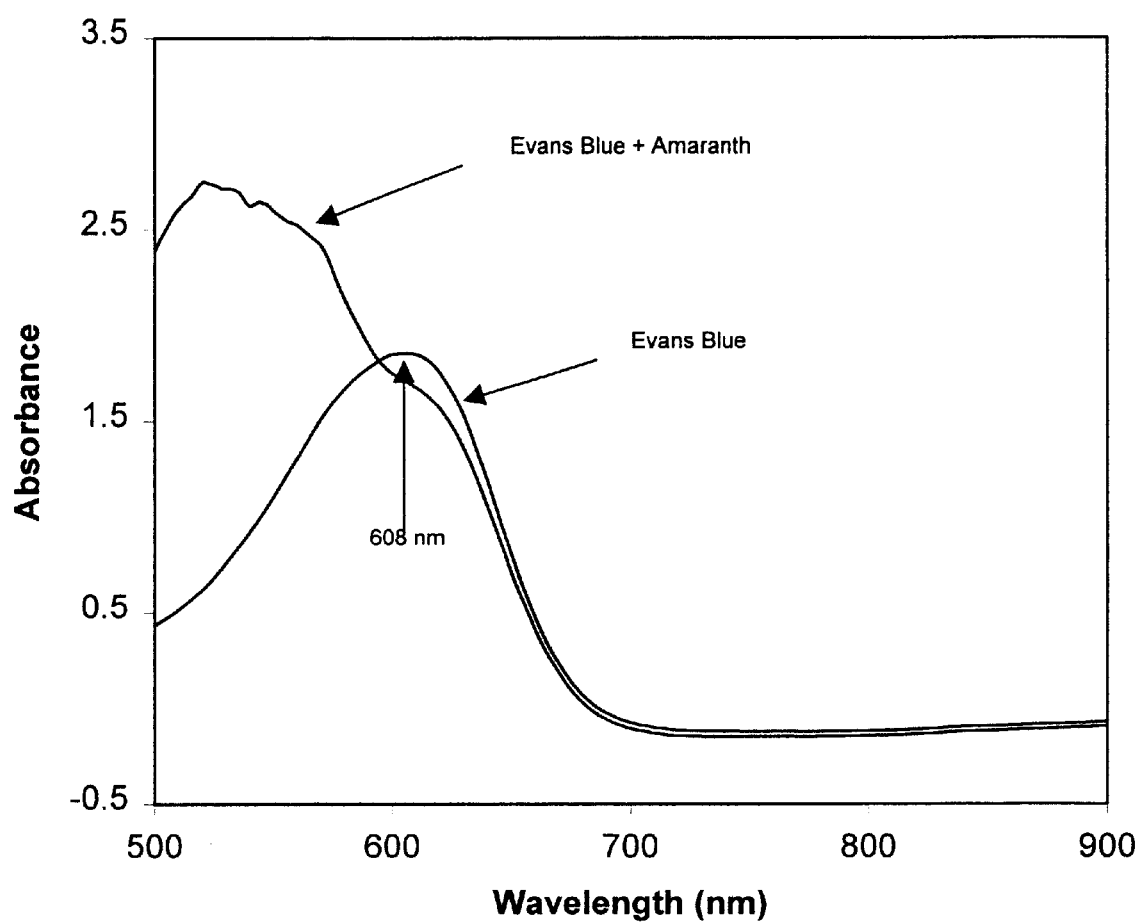
Figure 12D:
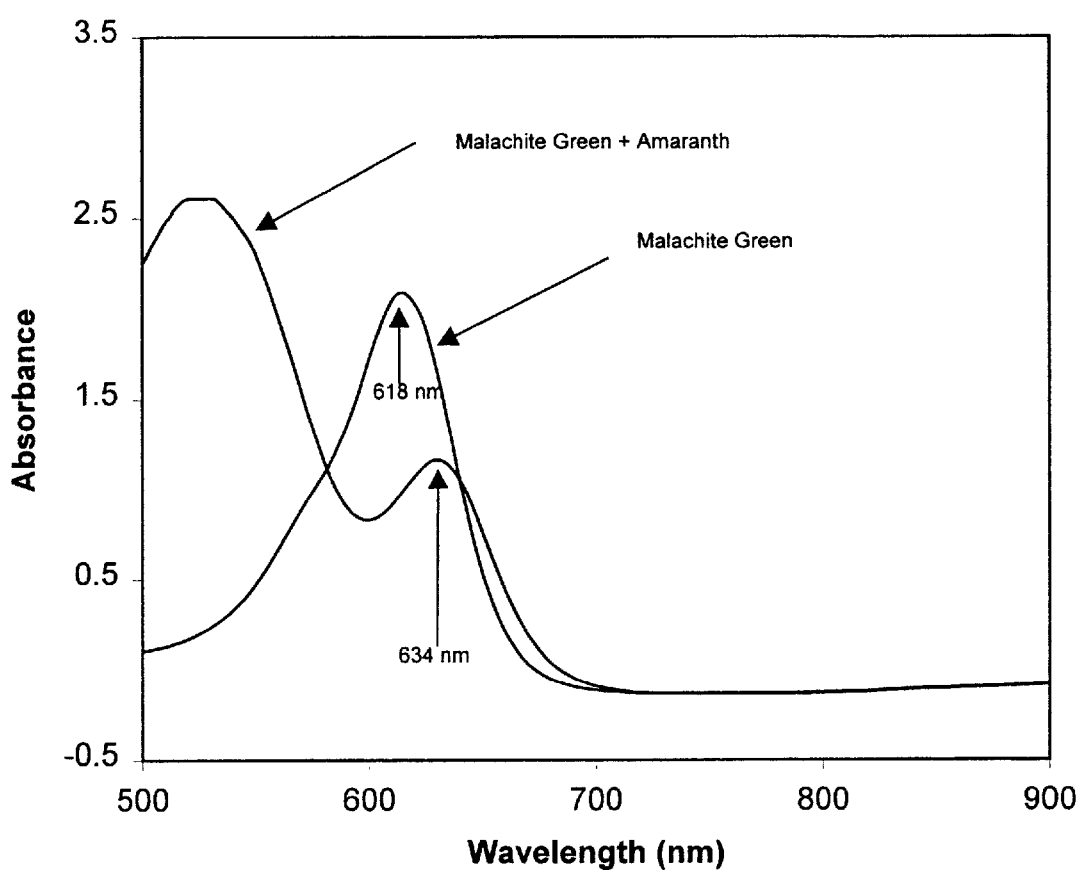
Figure 12E:
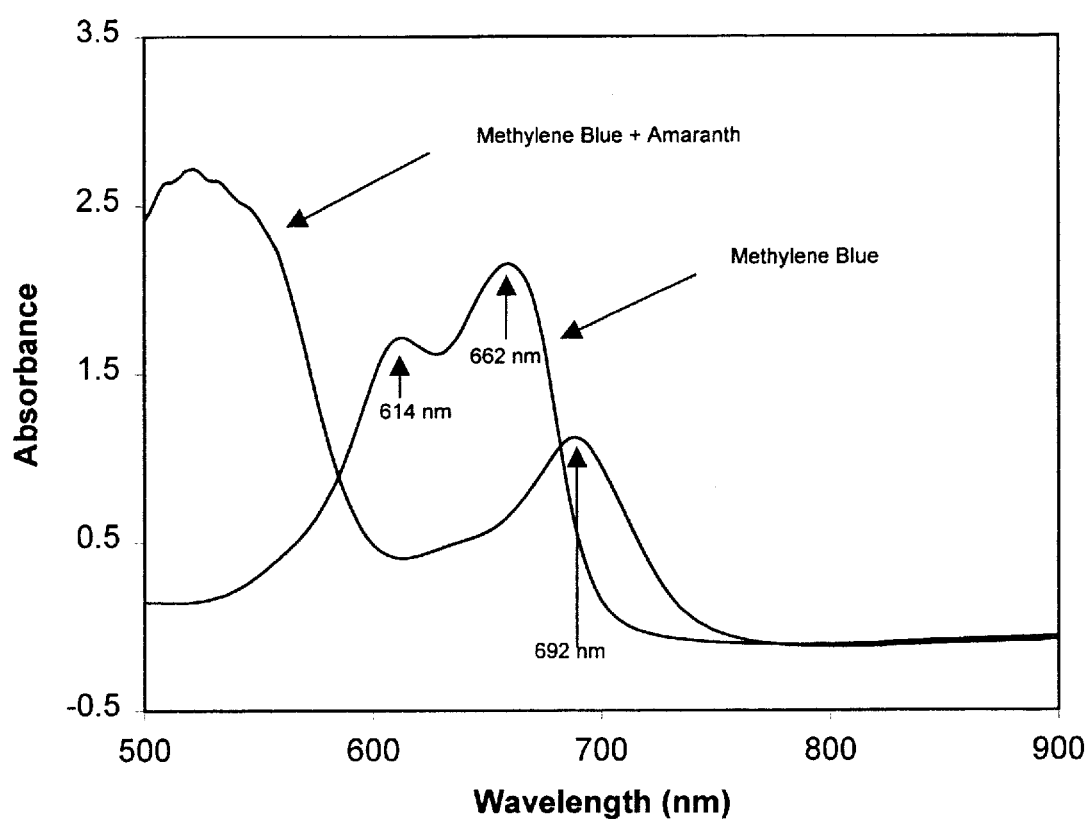
Figure 12F:
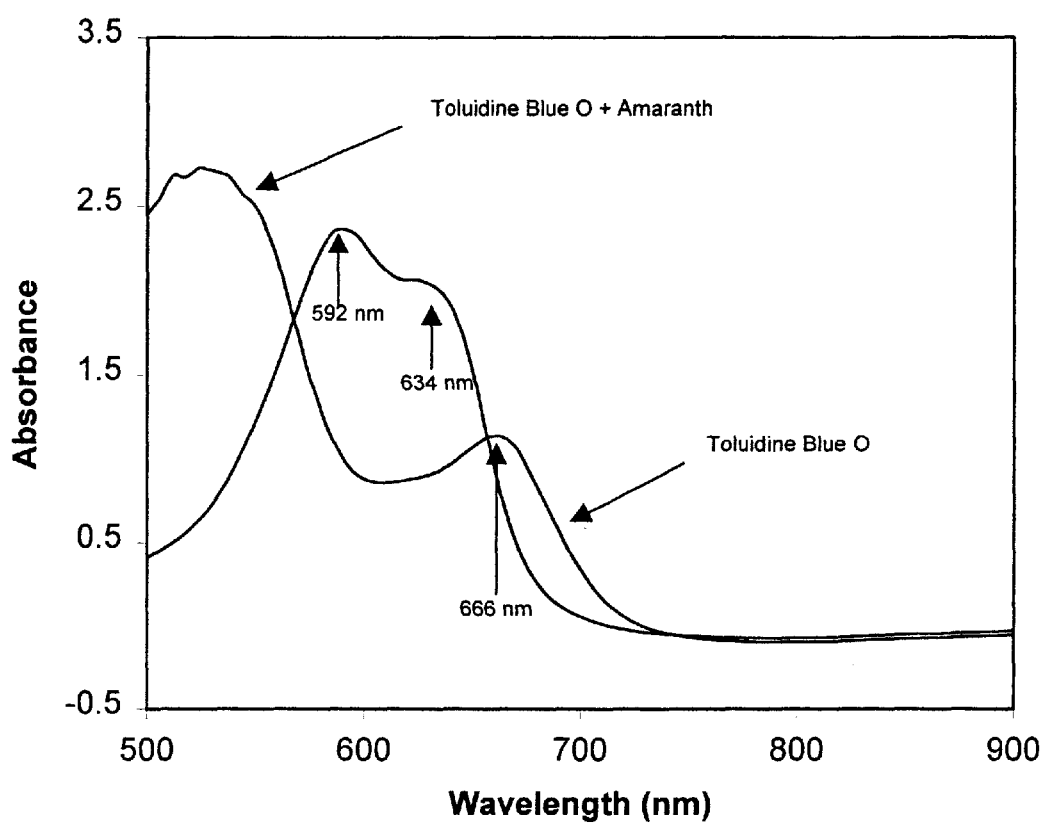
Figure 13A:
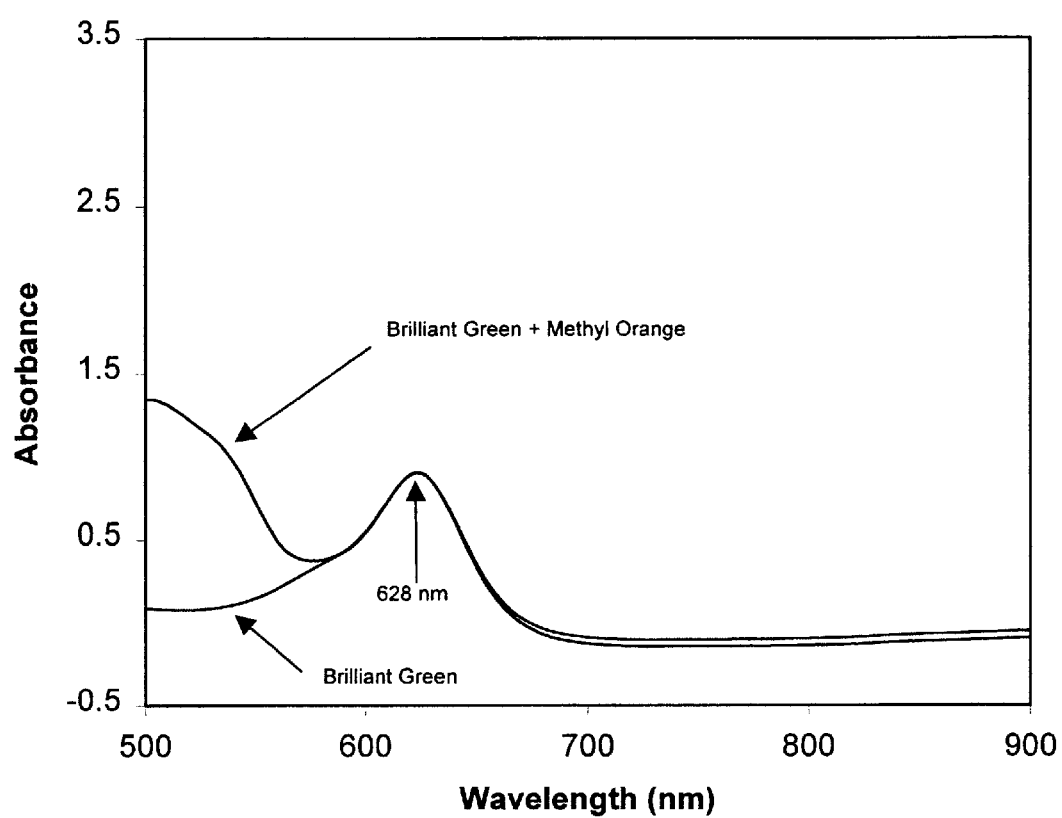
FIGS. 13(A–F) is a graphic representation of the absorbance spectra of the 6 different substances shown in FIG. 10, alone and mixed with Methyl Orange (FIGS. A–F).
Figure 13B:
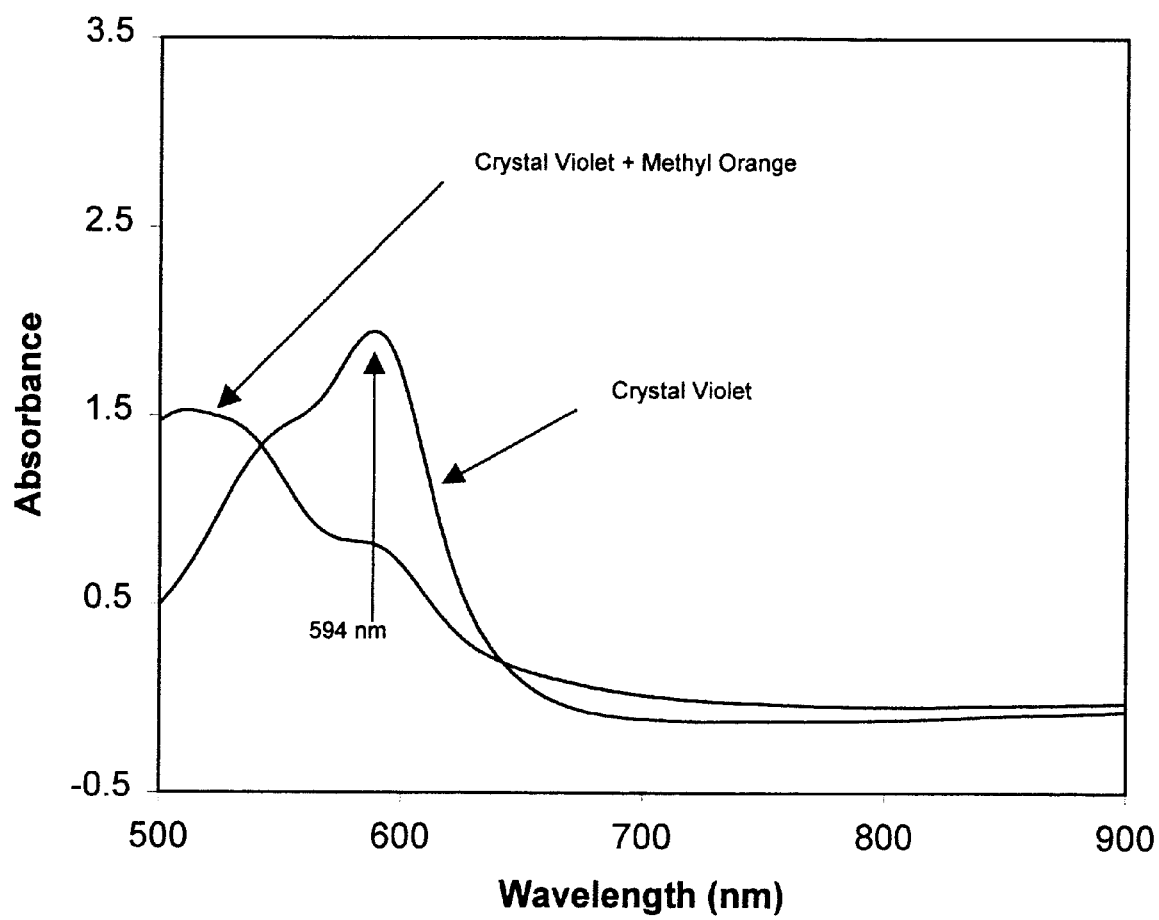
Figure 13C:
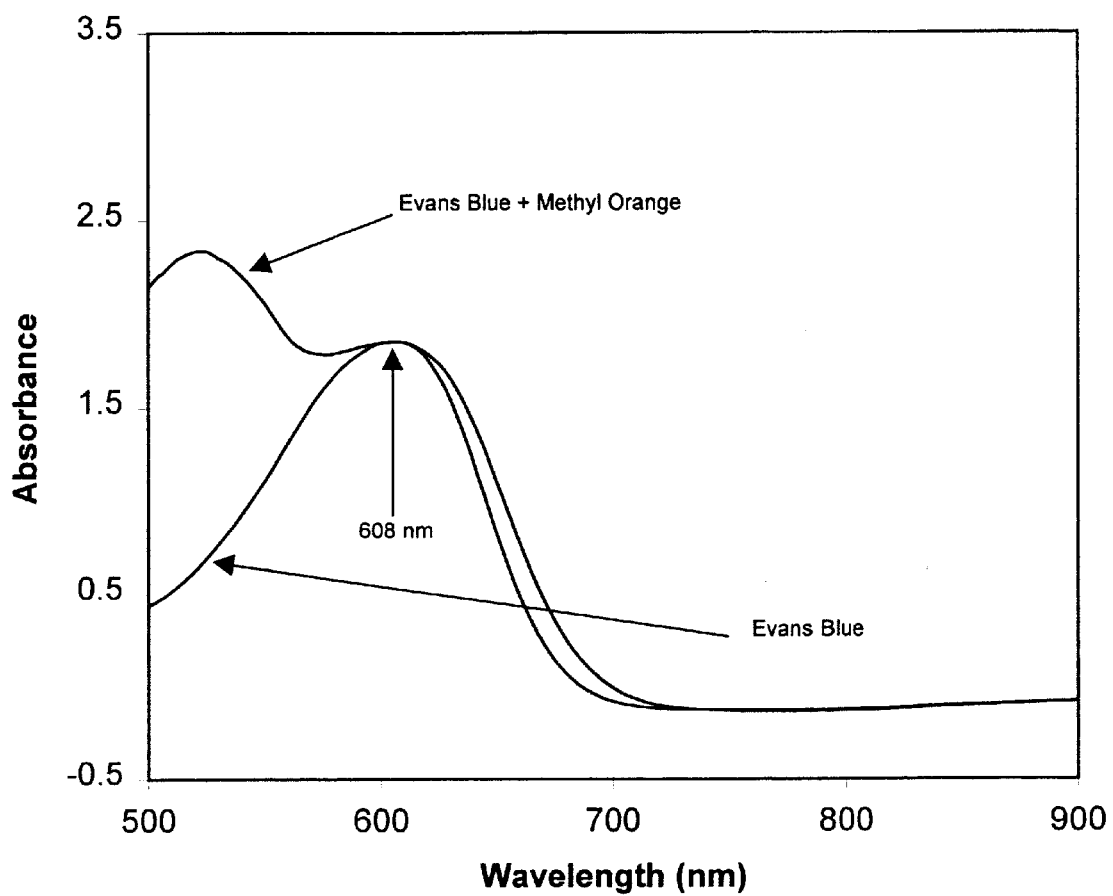
Figure 13D:
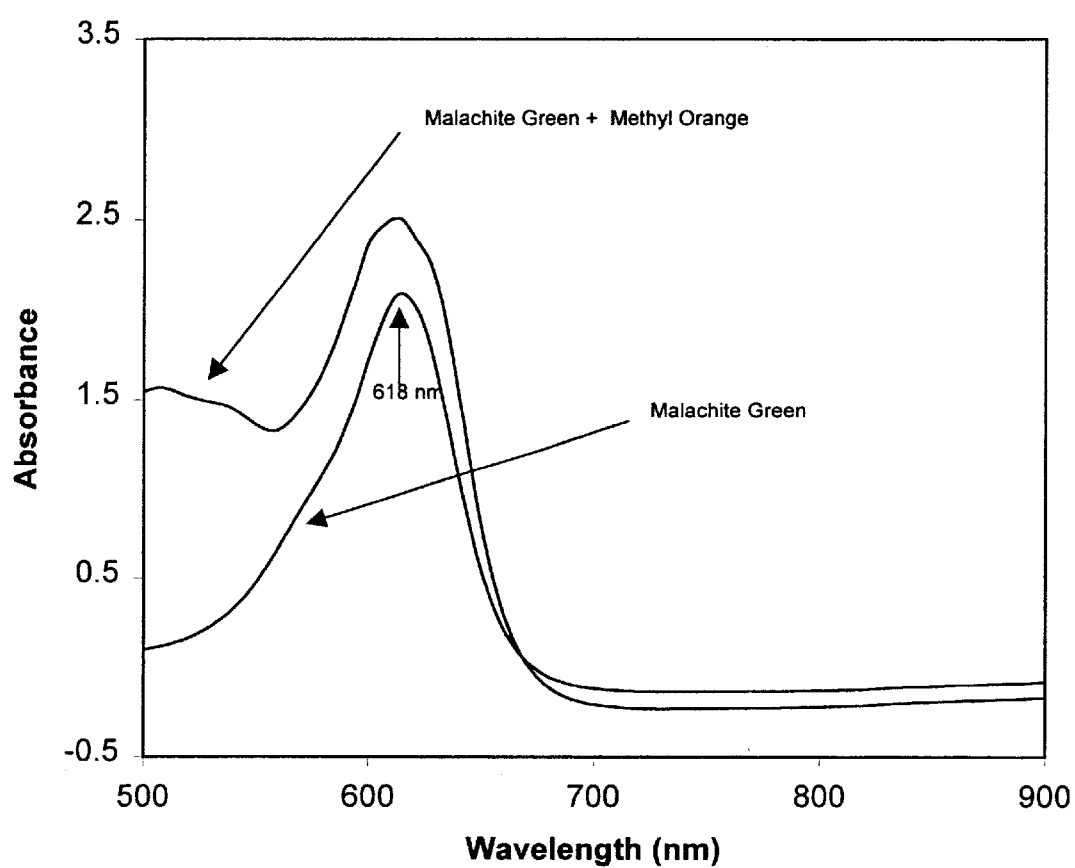
Figure 13E:
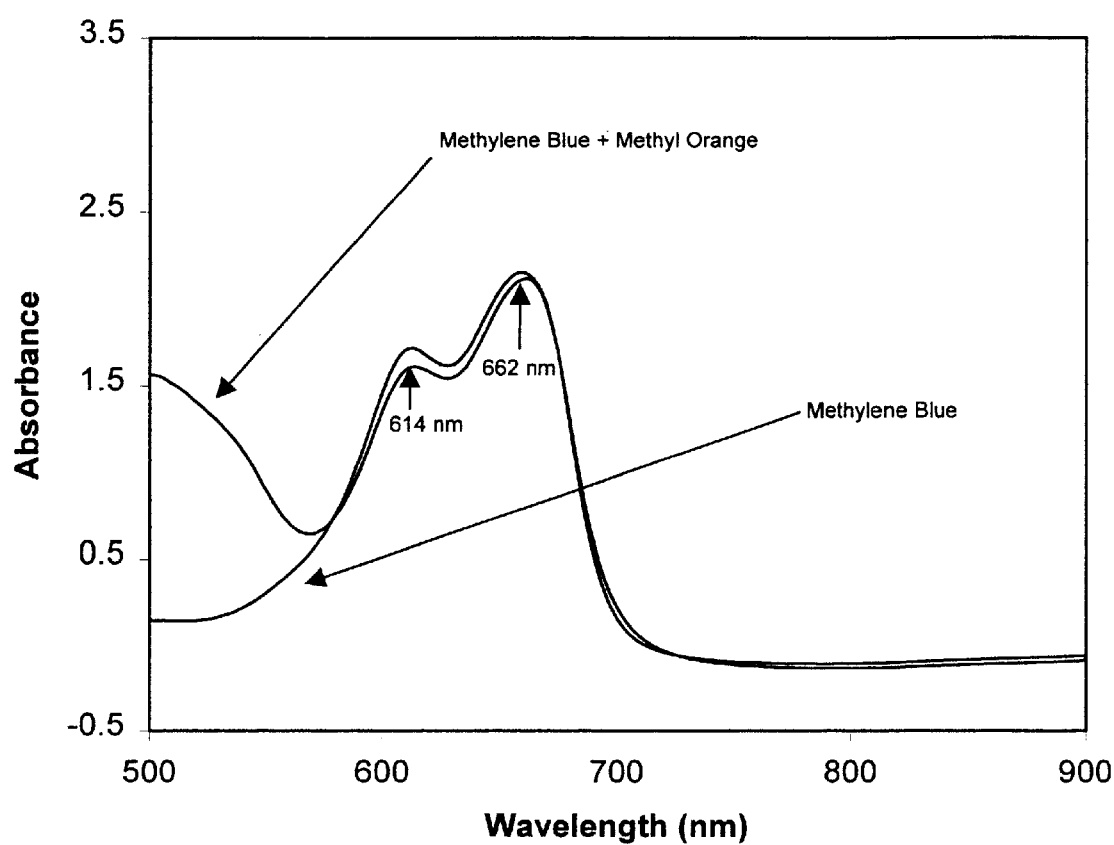
Figure 13F:
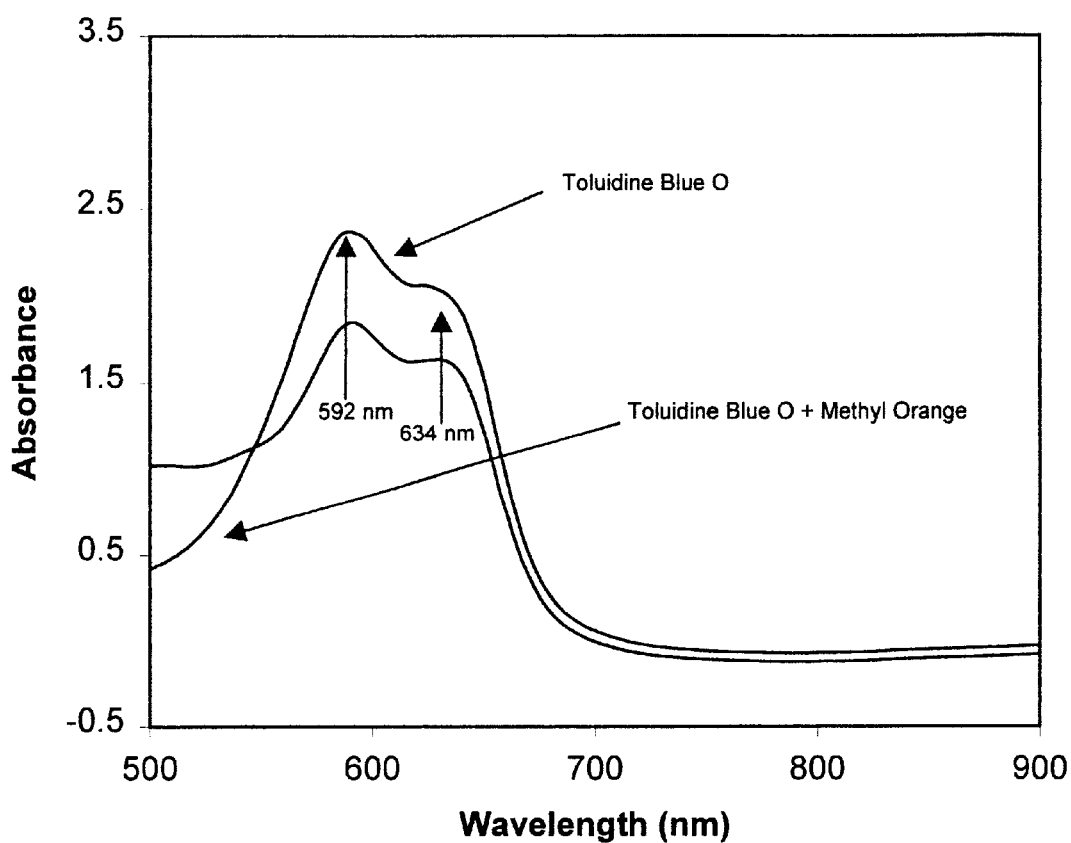
Figure 14A:
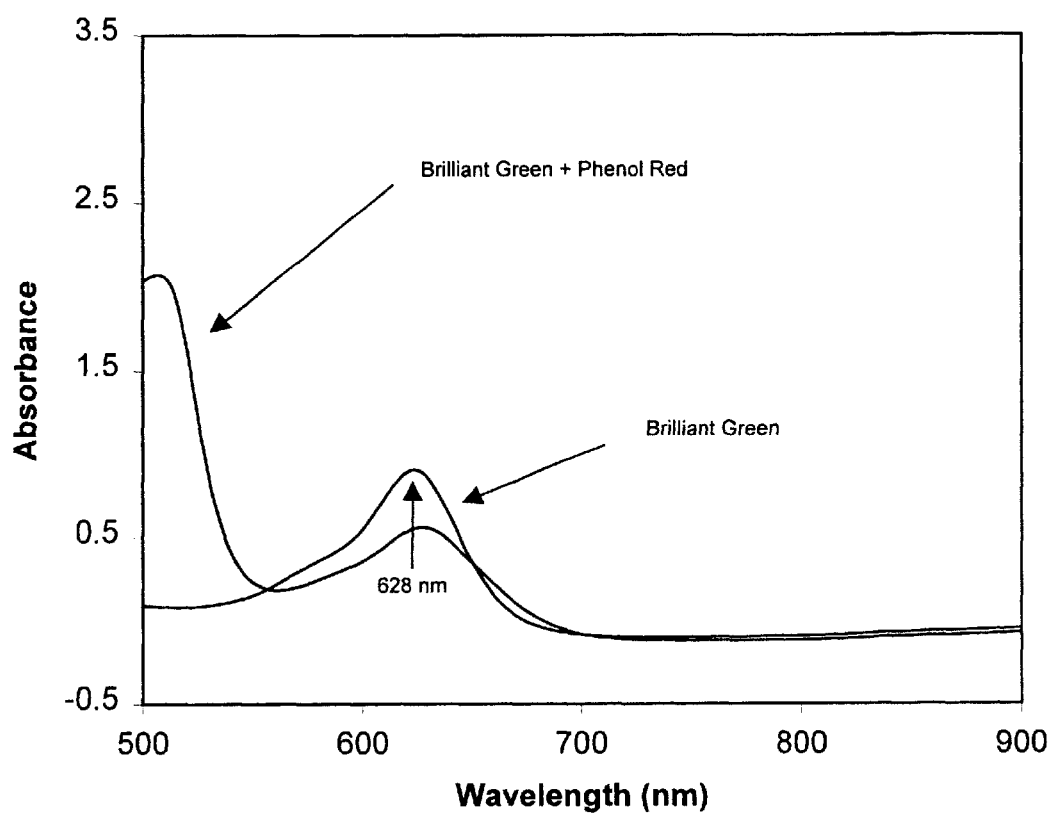
FIGS. 14(A–F) is a graphic representation of the absorbance spectra of the 6 different substances shown in FIG. 10, alone and mixed with Phenol Red (FIGS. A–F).
Figure 14B:
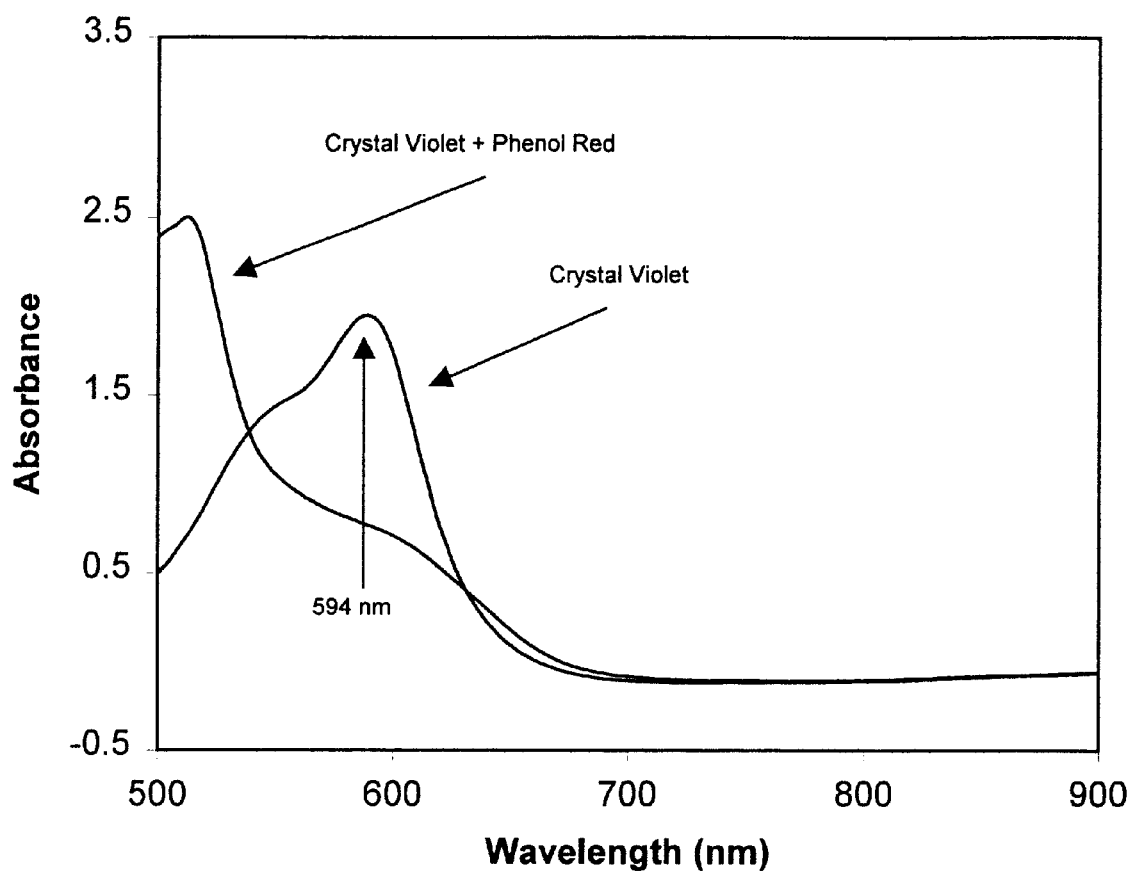
Figure 14C:
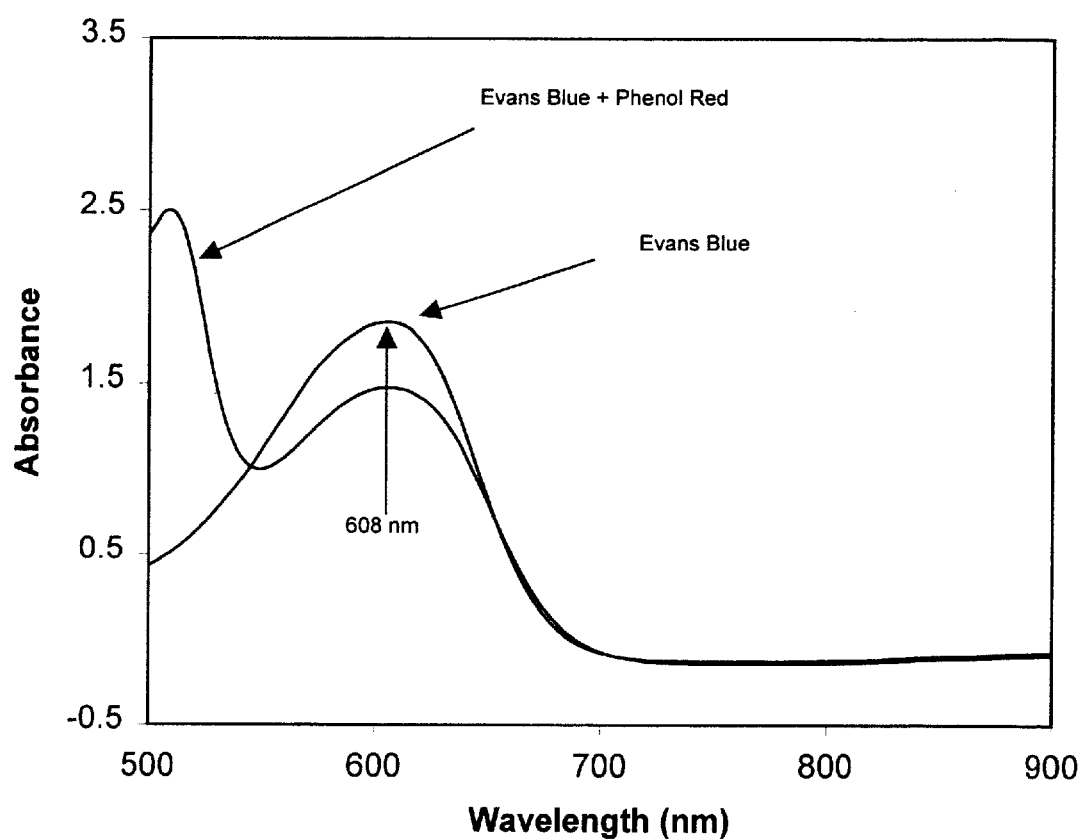
Figure 14D:
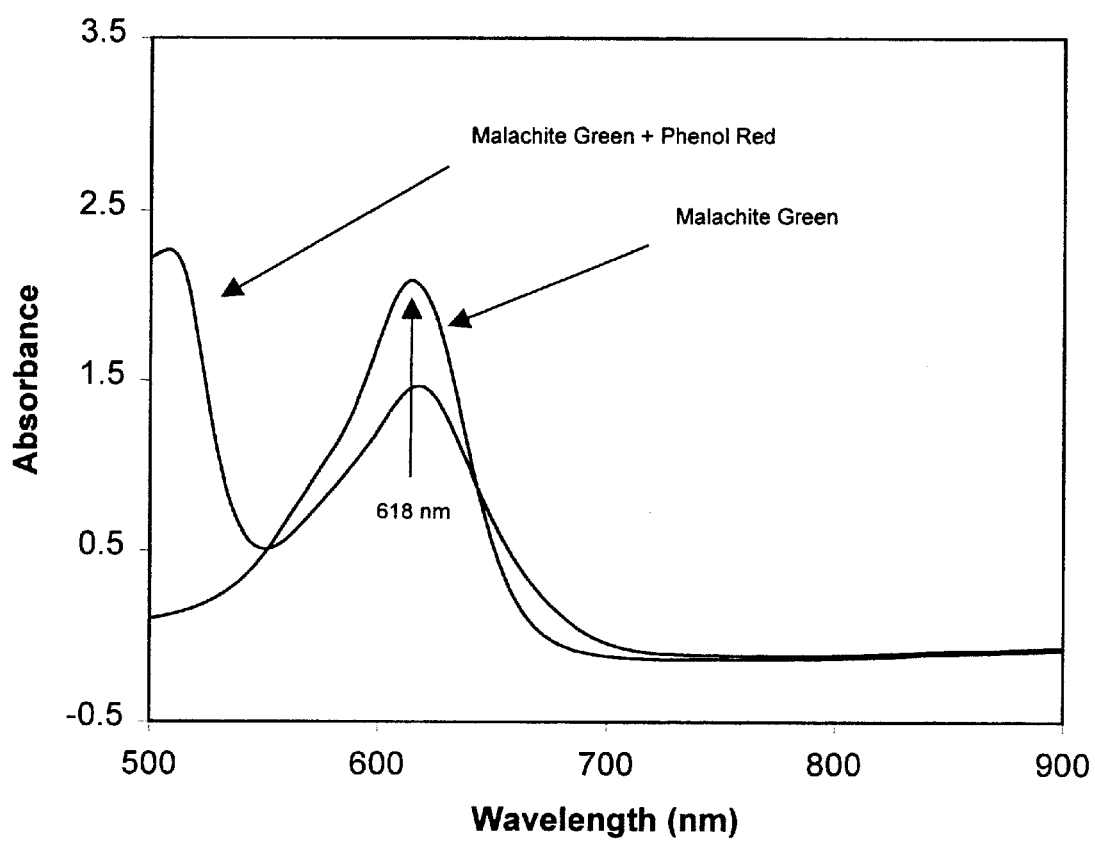
Figure 14F:
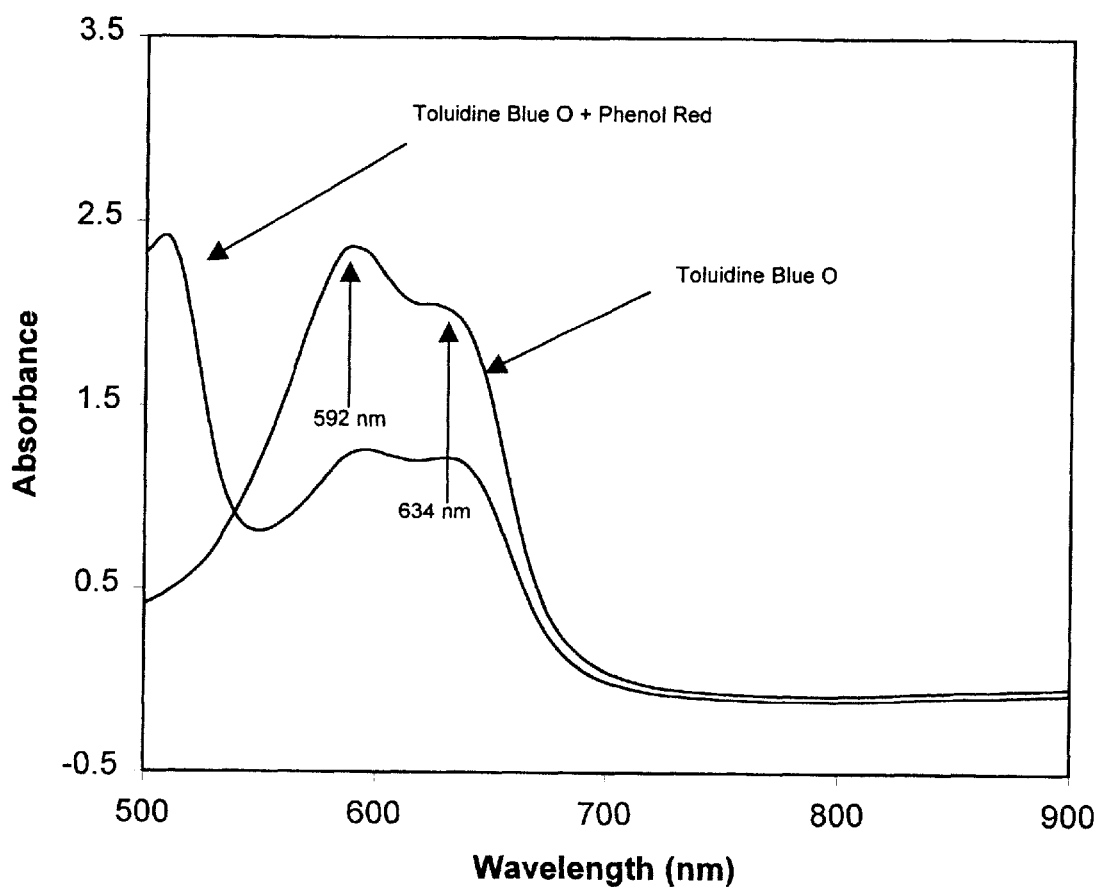

A low concentration of MB in the presence of amaranth may also be used to mimic MB when MB is present in the sample at a higher concentration than the QCM, due to the 30 nm right shift of the 662 nm absorbance peak of MB in the presence of amaranth (see FIG. 12E).

QCM for BV

The absorbance spectrum of BV is shown in FIGS. 4 & 5 as a broad band with an absorbance maximum at about 650 nm. BV absorbance spectrum has a negative absorbance slope between about 650 nm and about 800 nm as shown partly in FIG. 5. The absorbance maximum for this section of the absorbance spectrum is identified in FIG. 5 as 650 nm. The slope and an apparent right spectral shift increases with the concentration of BV. Only the negative absorbance slope of BV at the right of the 650 nm absorbance peak is exposed (FIG. 4); the left side is hidden due to the presence other compounds, for example BR, Hb, substances that cause turbidity, MB or a combination thereof.

Any one or more substances with a negative absorbance slope for a continuous spectral segment of at least 5 nm or more, within the wavelengths of 650 nm and 800 nm, can be used as a mimic of BV. Examples of such substances include brilliant green, crystal violet, evans blue, malachite green, methylene blue or toluidine blue O. Each of these substances may be used alone, or in combination as a mimic of BV. As in the case of met-Hb, the spectral shift caused by amaranth can be used to fine-tune the negative absorbance slope. These substances can be used alone or in combination with one or more substance, in order to mimic BV alone, or optionally in addition to one or more of BR, an indicator of hemolysis, met-Hb, MB, Hb-based blood substitutes, a simulator of turbidity and perfluorocarbon-like blood substitutes.

QCM for a Simulator of Turbidity

The preferred simulator of turbidity is IL, a lipid emulsion. The IL "absorbance" has a negative slope from about 500 nm to about 1100 nm depending on the concentration of IL, but only 500 nm to 900 nm is shown in FIG. 6 due to wavelength limitation of the apparatus used. IL zero order derivative of absorbance (i.e., the raw absorbance) also increases with increasing concentration over the about 500 nm to about 1100 nm range. Since significant spectral interferences by other substances like Hb exists at wavelengths less than about 700 nm, the preferred primary calibration wavelength for IL is greater than about 700 nm, for example from about 700 nm to about 1100 nm. The absorbance due to turbidity is inversely proportional to wavelength, as shown in FIG. 6 for IL (used to simulate turbidity).

FIG. 6 shows the absorbance spectra for 6 different concentrations of IL, which represents turbidity in serum and plasma. Example 5 gives sample primary calibration algorithms for IL, which includes both the zero and first order derivative of absorbance. Upon examination of FIG. 6 and the wavelengths used in the IL calibration algorithms listed in Table 1, any substance comprising an absorbance spectrum greater than about 700 nm, preferably from about 700 nm to about 1100 nm, may be used as a mimic for IL (a simulator of turbidity). Examples of substances that may be used to mimic IL, if the first order derivative of absorbance is used in the primary calibration algorithm, include but are not limited to MB with amaranth, toluidine blue O with amaranth, or copper sulfate alone. If the zero order derivative of absorbance is used, copper sulfate alone can be used. If the primary calibration algorithm is at about 700 nm, copper sulfate can be used in combination with methylene blue and amaranth, as shown in FIG. 16. It should be understood by those skilled in the art that any combination of substances can be used to mimic a simulator of turbidity, and the substances used would depend on the calibration wavelengths and the order derivative of absorbance used in the primary calibration algorithm. As in the case of the previously discussed analytes, these substances can be used alone or in combination with one or more substance, in order to mimic a simulator of turbidity alone, or optionally in addition to one or more of BV, BR, an indicator of hemolysis, met-Hb, MB, Hb-based blood substitutes, and perfluorocarbon-like blood substitutes.

Monitoring of a Primary Calibration Algorithm

Once a QCM has been selected it can be used to monitor a primary calibration algorithm for one or more analytes, without the use of reagents. To do so, an absorbance spectrum of the QCM in the region of interest is obtained. The order derivative of absorbance value is measured at the wavelength(s) of the primary calibration algorithm and these values are used to calculate a concentration. This concentration is compared to an assigned value given to the QCM. It is then determined whether this value falls within certain ranges established using quality control rules such as Westgard's multirules.

Thus in a further aspect of the invention there is provided a method of monitoring calibration of a spectrophotometric apparatus comprising one or more calibration algorithms for one or more analytes comprising:

i) measuring absorbance of a quality control material with the apparatus to obtain a measurement, the quality control material exhibiting an absorbance spectra characterized as having a negative slope for a continuous spectral segment from about 5 nm to about 400 nm in length, the spectral segment including a principal calibration wavelength for the one or more analytes;

ii) calculating one or more concentration values from the measurement using the one or more calibration algorithms;

iii) comparing the one or more concentration values with an assigned value given to the quality control material for each of the one or more analytes; and iv) determining if there is a violation of a pre-established quality control rule, thereby monitoring said one or more calibration algorithms of the spectrophotometric apparatus Determining the Concentration of One or More Analytes in a Sample Once the primary calibration algorithm has been monitored and that there is no violation of quality control rules, the primary calibration algorithm can be used to determine the concentration of an analyte.

Therefore, the present invention also provides a method for determining the concentration of one or more analytes in a sample in an apparatus comprising at least one primary calibration algorithm comprising:
  i) monitoring calibration of the apparatus as described above (see method of monitoring calibration of a spectrophotometric apparatus);
  ii) establishing that there is no violation of a pre-established quality control rule:
  iii) measuring absorbance values of the sample;
  iv) calculating an order derivative of absorbance of the sample; and v) calculating a concentration of the one or more analytes in the sample, by applying the primary calibration algorithm to the order derivative of absorbance value.

QCMs can also be used to calibrate an apparatus. In this respect, the absorbance spectrum of the QCM may or may not be similar to the absorption spectrum of the blood analyte provided that a linear regression equation correlating the absorbance of 2 or more concentrations of the QCM on a first apparatus and the absorbance of 2 or more concentrations of the same QCM on a different apparatus can be obtained. Target ranges of the correlation coefficient, slope and y-intercept may be assigned outside which the apparatus is deemed to be out of calibration. Similarly, the linear regression equation may correlate the absorbance of 2 or more concentrations of the QCM obtained on an apparatus and the absorbance of 2 or more concentrations of the same QCM tested on the same apparatus at a different time. Non-limiting examples of substances that can be used as calibrators are shown in FIG. 17.

A summary of exemplary primary calibration algorithms, which are not to be considered limiting in any manner, using the methods as described herein are presented in Table 1. It is to be understood that other primary calibration algorithms may be readily obtained using different substances, or sample containers, etc, and using the methods as described herein

TABLE 1

Wavelengths used in primary calibration algorithms shown in Examples 1 to 7, arranged according to analyte.

| Equation No. | Analyte | Wavelengths (nm) | | | |
|---|---|---|---|---|---|
| | | 1 | 2 | 3 | 4 |
| 1 | Hb | 584 | 599 | 617 | — |
| 2 | Hb | 600 | 618 | — | — |
| 3 | Hb | 591 | 653 | — | — |
| 4 | Hb | 600 | 663 | — | — |
| 5 | Hb | 558 | 570 | 730 | — |
| 6 | Hb | 591 | 610 | — | — |
| 7 | Hb-based Blood Substitute | 541 | 558 | 600 | 616 |
| 8 | BV | 649 | 731 | 907 | — |
| 9 | BV | 724 | 803 | — | — |
| 10 | BV | 718 | 781 | — | — |
| 11 | BR | 524 | 587 | 602 | — |
| 12 | BR | 534 | 586 | — | — |
| 13 | BR | 504 | 518 | 577 | — |
| 14 | BR | 495 | 512 | 578 | — |
| 15 | BR | 511 | 554 | — | — |
| 16 | IL | 700 | — | — | — |
| 17 | IL | 872 | — | — | — |
| 18 | IL | 988 | 1038 | — | — |
| 19 | IL | 874 | — | — | — |
| 20 | IL | 874 | — | — | — |
| 21 | IL | 900 | — | — | — |
| 22 | Met-Hb | 645 | 669 | — | — |
| 23 | MB | 702 | 759 | — | — |
| 24 | MB | 677 | 953 | — | — |

Also, the lowest and highest wavelengths shown in Table 1 are 504 nm and 1038 nm respectively, but it should be understood that calibration wavelengths within the range of about 450 nm to about 3000 nm are within the scope of this invention.

The above description is not intended to limit the claimed invention in any manner. Furthermore, the discussed combination of features might not be absolutely necessary for the inventive solution.

The present invention will be further illustrated in the following Examples. However, it is to be understood that these examples are for illustrative purposes only and should not be used to limit the scope of the present invention in any manner.

EXAMPLES

Examples of calibration sets used to derive primary calibration algorithms for BR an indicator of hemolysis, Hb-based blood substitutes, met-Hb, MB, BV and a simulator of turbidity are provided below, however, it should be understood that these examples are not to be considered limiting in any manner. It should be understood by those skilled in the art that methods use to develop calibration algorithms for Hb-based blood substitutes, total Hb, oxy-Hb and "Total Hb minus met-Hb" are very similar, and methods used to develop calibration algorithms for perfluorocarbon-like blood substitutes, are very similar to the method for IL.

Example 1

Hemoglobin

To prepare a Primary Calibration Algorithm for hemoglobin, sixty serum specimens with no visible interferents were stored refrigerated or frozen until used. More or fewer specimens may be used so long as a sufficient number is used to provide robust algorithm(s). Hb, IL, BR and BV were added to the normal sera to give final concentrations of 0–6.1 g/L, 0–5.1 g/l, 0–42.7 mg/dL, and 0–4.4 mg/dL respectively. Stock Hb was prepared by replacing the plasma (must be free from all interferents) from a blood sample, with twice its volume of water, and lysing the cells through three freeze-thaw cycles. For each cycle the blood was left in the freezer for 45–60 minutes, and then removed and placed on a rocker at room temperature for 30–45 minutes. Hb content of the lysate was measured by a spectrophotometric method for measuring oxy-Hb described by Tietz (Tietz Textbook of Clinical Chemistry, $2^{nd}$ Ed, 1994, pp 2022–2025), after removing the RBC debris and unlysed RBC's by centrifuging at 10,000×g for 10 minutes. Any method that provides a reliable determination of Hb content may be used. A typical hemolysate contains approximately 100 g/L Hb. CO-oximetry suggests that more than 95% of the Hb is in the oxy-Hb state. Stock BV was prepared by dissolving biliverdin dihydrochloride (preferably obtained from Sigma) initially in 50% methanol-50% water, and diluting further with phosphate buffered saline (PBS). Stock IL also known as Travamulsion™(preferably obtained from Clintec-Nestle & Baxter) has a concentration of 10%. Stock BR was prepared by dissolving Ditauro-Bilirubin (from Porphyrin Products, Logan, Utah, USA) in interferent-free serum, to a concentration of 500 mg/dL. The spectral absorbance data were recorded for the 60 samples using different polypropylene dispensing tips. Out of the 60 samples, odd numbers were used for the calibration set, and even numbers were used as the validation set. This primary calibration set does not contain met-Hb or MB, therefore these substances may contribute to inaccuracies in the Hb measurements. Met-Hb and MB may be included in the absorbance variability of the primary calibration set, in order to obtain more robust primary calibration algorithms.

Examples of primary calibration algorithms for Hb using the method described in the present application are given below. It will be appreciated that the algorithms can differ when the conditions in which they are obtained differ Although the examples below show "g/L Hb" as the dependant variable, it should be understood that the dependant variable could be any indicator of hemolysis related to Hb, for example, total Hb, oxy-Hb and "total Hb minus met-Hb." The true indicator of hemolysis depends on both the reference method used to measure the indicator of hemolysis, and the substances included in the primary calibration set. As another aspect of this invention, methods for making corrections to the indicator of hemolysis are described, and whether correction is performed on the indicator of hemolysis, or the value of the indicator of hemolysis is only flagged to indicator potential error in the value, depends on the required accuracy of the indicator of hemolysis.

Equation 1 (Obtained Using Disposable Polypropylene Dispensing Tips)

$$\text{g/L Hb} = -16.81(1st\ D\ A584) + 79.47\ (1st\ D\ A599) - 60.95(1st\ D\ A617) + 0.24$$

where (1st D A) is the first derivative of the absorbance measurement at the wavelength specified in nanometers.

Equation 2 (Obtained Using 12 mm Disposable Polypropylene Tubes)

$$\text{g/L Hb} = 113.27\ (1st\ D\ A600) - 182.94(1st\ D\ A618) - 0.13$$

where (1st D A) is the first derivative of the absorbance measurement at the wavelength specified in nanometers.

The following other examples of primary calibration algorithms for Hb are described in U.S. Pat. Nos. 6,268,910 B11 and 5,846,492, WO 98/39634 and WO 97/47972.

Equation 3 (Obtained Using Blood Bag Tubing)

$$\text{g/L Hb} = 45.68\ (1st\ D\ A591) - 47.48(1st\ D\ A653) - 0.42$$

where (1st D A) is the first derivative of the absorbance measurement at the wavelength specified in nanometers.

Equation 4 (Obtained Using Disposable Plastic Dispensing Tips)

$$\text{g/L Hb} = 15.89\ (1st\ D\ A600) - 15.88(1st\ D\ A663) - 0.21$$

where (1st D A) is the first derivative of the absorbance measurement at the wavelength specified in nanometers.

Equation 5 (Obtained Using Disposable Plastic Dispensing Tips)

$$\text{g/L Hb} = 30.72\ (1st\ D\ A558) - 17.40(1st\ D\ A570) + 171.14(1st\ D\ A730) - 072$$

where (1st D A) is the first derivative of the absorbance measurement at the wavelength specified in nanometers.

Equation 6 (Obtained Using Translucent Pipette Tips)

$$(g/L)Hb = 30.14(1st\ D\ A591) - 27.98(610)$$

where (1st D A) is the first derivative of the absorbance measurement at the wavelength specified in nanometers.

Example 2

Hb-based Blood Substitutes

The following is an example of a primary calibration algorithm for Hb-based blood substitute as described in WO 98/39634.

Equation 7 (Obtained Using Disposable Polypropylene Dispensing Tips)

$$\text{g/L Hb-based blood substitute} = 23.97(1st\ D\ A541) - 76.01(1st\ D\ A558) + 130.84(1st\ D\ A600) - 113.61(1st\ D\ A616) + 0.30$$

where (1st D A) is the first derivative of the absorbance measurement at the wavelength specified in nanometers.

Example 3

Biliverdin

The following examples of primary calibrations algorithms for biliverdin are described in U.S. Pat. No. 6,268,910 B1 and 5,846,492 and WO 97/47972.

Equation 8 (Obtained Using Blood Bag Tubing)

$$\text{mg/L BV} = -45.40(1st\ D\ A649) + 323.15(1st\ D\ A731) - 493.79(1st\ D\ A907) - 1.14$$

where (1st D A) is the first derivative of the absorbance measurement at the wavelength specified in nanometers.

Equation 9 (Obtained Using Disposable Plastic Dispensing Tips)

$$\text{mg/L BV} = 98.07(1st\ D\ A724\ nm) - 122.73(1st\ D\ A803\ nm) + 0.07$$

where (1st D A) is the first derivative of the absorbance measurement at the wavelength specified in nanometers.

Equation 10 (Obtained Using Translucent Pipette Tips)

$$\text{mg/dL BV} = 160.29(1st\ D\ A718) - 206.15(1st\ D\ A781) + 1.42$$

where (1st D A) is the first derivative of the absorbance measurement at the wavelength specified in nanometers.

Example 4

Bilirubin

The sample set used for Hb calibration is not typically used for BR calibration, because the absorbance due to either Hb>4 g/L or IL>4 g/L, approaches the limit of the apparatus in the region around 524 nm, a primary wavelength used for BR calibration. Instead, a separate set of 60 samples were prepared and tested. As will be readily appreciated by those skilled in the art, the sample set used for primary calibration should be of a size sufficient to include most of the variability encountered with actual patient samples, such as serum or plasma. The samples were prepared as before by adding Hb, IL, BR and BV to the normal sera to give final concentrations of 0–2.6 g/L, 0–3.6 g/l, 0–37 mg/dL, and 0–4.4 mg/dL respectively. The spectral absorbance data were recorded for the 60 samples using different polypropylene dispensing tips. Out of the 60 samples, odd numbers were used for the calibration set, and even numbers were used as the validation set. The stock interferents were prepared as described above for Hb, and the BR concentrations were adjusted by the factor 1.23. The 1.23 factor that was derived previously from the slope of the regression line obtained from a validation set using real icteric serum and plasma samples. Met-Hb and MB is not expected to interfere with BR predictions, but they can only help to create more robust primary calibration algorithms, if they were included in the absorbance variability of the primary calibration set.

Equation 11 (Obtained Using Disposable Polypropylene Dispensing Tips)

$$\text{mg/dL BR} = 293.1(1st\ D\ A524) + 327.8(1st\ D\ A587) - 451.7(1st\ D\ A602) - 7.5$$

where (1st D A) is the first derivative of the absorbance measurement at the wavelength specified in nanometers.

Equation 12 (Obtained Using 12 mm Disposable Polypropylene Tubes)

$$mg/dL\ BR=406.04(1st\ D\ A534)+183.94(1st\ D\ A586)-2.27$$

where (1st D A) is the first derivative of the absorbance measurement at the wavelength specified in nanometers.

The following examples of primary calibrations algorithms for bilirubin are described in U.S. Pat. Nos. 6,268,910 B1, 5,846,492 and WO 97/47972.

Equation 13 (Obtained Using Blood Bag Tubing)

$$mg/dL\ BR=-43.03(1st\ D\ A504)+252.11(1st\ D\ A518)+240.03(1st\ D\ A577)-2.89$$

where (1st D A) is the first derivative of the absorbance measurement at the wavelength specified in nanometers.

Equation 14 (Obtained Using Disposable Plastic Dispensing Tips)

$$mg/dL\ BR=-24.88(1st\ D\ A495)+201.61(1st\ D\ A512)+44.98(1st\ D\ A578\ nm)-6.48$$

where (1st D A) is the first derivative of the absorbance measurement at the wavelength specified in nanometers.

Equation 15 (Obtained Using Translucent Pipette Tips)

$$mg/dL\ BR=142.09(1st\ D\ A511)+89.9(1st\ D\ A554)-4.47$$

where (1st D A) is the first derivative of the absorbance measurement at the wavelength specified in nanometers.

Example 5

Turbidity

Turbidity in serum and plasma is caused Mainly by the presence of fat particles, particularly chylomicrons. Intralipid™ (IL) is a lipid emulsion that simulates naturally-occurring chylomicrons, and therefore may preferably be used to simulate turbidity in serum and plasma.

Samples used for Hb and BR calibration are preferably not used for IL calibration because the Hb stock solution contributes significant light scattering (like lipid particles) due to unlysed RBC's and RBC fragments. Centrifugation of the hemolysate was unable to remove all the unlysed RBC's and RBC fragments.

Forty samples of PBS (phosphate buffered saline) were spiked with 10% Intralipid™ to produce concentrations of 0–20 g/L. The spectral absorbance data were recorded for the 40 samples using different polypropylene dispensing tips. Out of the 40 samples, the odd numbers were used for the calibration set, and the even numbers were used as the validation set. Suitable wavelengths used for IL calibration are from about 700 nm to about 1100 nm.

Turbidity is measured in terms of equivalent IL concentration.

Equation 16 (Obtained Using Disposable Polypropylene Dispensing Tips)

$$\ln(g/L\ IL)=1.867(A700)-0.447(A700)^2+0.041(A700)^3-1.33$$

where (A) is the raw absorbance measurement at the wavelength specified in nanometers.

Equation 17 (Obtained Using 12 mm Disposable Polypropylene Tubes)

$$g/L\ IL=2.72(A872)-3.88(A872)2+1.70(A872)^3+0.19$$

where (A) is the raw absorbance measurement at the wavelength specified in nanometers.

The following examples of primary calibrations algorithms for IL are described in U.S. Pat. Nos. 6,268,910 B1, 5,846,492 and WO 97/47972.

Equation 18 (Obtained Using Blood Bag Tubing)

$$g/L\ IL=432.42(1st\ D\ A988)+40.40\ (1st\ D\ A1038)+0.04$$

where (1st D A) is the first derivative of the absorbance measurement at the wavelength specified in nanometers.

Equation 19 (Obtained Using Blood Bag Tubing)

$$g/L\ IL=305.78\ (1st\ D\ A874)+1.12$$

where (1st D A) is the first derivative of the absorbance measurement at the wavelength specified in nanometers.

Equation 20 (Obtained Using Disposable Plastic Dispensing Tips)

$$g/L\ IL=252.16(1st\ D\ A874\ nm)+0.24$$

where (1st D A) is the first derivative of the absorbance measurement at the wavelength specified.

Equation 21 (Obtained Using Translucent Pipette Tips)

$$g/L\ IL=296.01(A900)-0.04$$

where (A) is the raw absorbance measurement at the wavelength specified in nanometers.

Example 6

Met-Hemoglobin

Twenty nine samples comprising fresh hemolysate that contained about 95% oxy-Hb, met-Hb, MB, BV and IL were used to calibrate an apparatus that used Teflon™ sample holders. BR was not added to the samples because BR does not absorb light at the wavelengths used to calibrate for either met-Hb or MB. The met-Hb was obtained in lyophilized form from Sigma, and was reconstituted in phosphate buffered saline. An absorbance spectrum of 10 g/L of reconstituted lyophilized met-Hb is shown in FIG. 1. Examples of absorbance spectra obtained from the apparatus used are given in FIG. 4. As mentioned above, the primary calibrations described herein is exemplary of the work involved in developing primary calibration algorithms.

Equation 22 (Obtained Using Teflon™ Sample Holders)

$$g/L\ Met\text{-}Hb=69.88\ (1st\ D\ A645)+53.15(1st\ D\ A669)-1.17$$

where (1st D A) is the first derivative of the absorbance measurement at the wavelength specified.

Example 7

Methylene Blue

Equation 23 (Obtained Using Teflon™ Sample Holders)

$$mg/L\ MB=162.53\ (1st\ D\ A702)-112.58(1st\ D\ A759)-1.17$$

where (1st D A) is the first derivative of the absorbance measurement at the wavelength specified.

The following example of a primary calibration algorithm for MB is described in U.S. Pat. No. 6,268,910 B1.

Equation 24 (Obtained Using Blood Bag Tubing)

$$mg/L\ MB=56.04(1st\ D\ A677)+267.21(1st\ D\ A953)+4.49$$

where (1st D A) is the first derivative of the absorbance measurement at the wavelength specified in nanometers.

The Primary Calibration Algorithms referred to herein are non-limiting examples obtained by a process of step-wise multiple linear regression. Other methods like simple linear regression, PLS and PCA may also be used. It must be understood that any order derivative of absorbance can be used, as shown for IL, although no order higher than the first order is given in any of the examples. It should also be understood, that the robustness of a primary calibration algorithm depends on the inclusion of substances in the primary calibration sets that absorb or scatter light around the principal calibration wavelength(s).

All citations are herein incorporated by reference.

While the invention has been particularly shown and described with reference to certain embodiments, it will be understood by those skilled in the art that various other changes in form and detail may be made without departing from the spirit and scope of the invention.

We claim:

1. A method for producing a corrected predicted value for an indicator of hemolysis in a sample, in the presence of methemoglobin (metHb), said method comprising the steps of:
   i) developing a first primary calibration algorithm for one of a total hemoglobin (Hb), an oxy-hemoglobin (oxy-Hb), or a total hemoglobin-methemoglobin (Hb-methb), for predicting a first value for one of said total Hb, said oxy-Hb, or said total Hb-metHb, in said sample wherein said total Hb, said oxy-Hb, or said total Hb-metHb serves as an indicator of hemolysis and said example;
   ii) deriving a second primary calibration algorithm for said met-Hb, for predicting a second value for said met-Hb in said sample; and
   iii) adding said predicted second value for said met-Hb to one said predicted first value for total Hb, said predicted first value for oxy-Hb, or said predicted first value for total Hb-metHb, to produce said corrected predicted value for an indicator or hemolysis.

2. The method of claim 1, wherein said step of developing (step i)) and said step of deriving (step ii)), each comprises the steps of:
   a) collecting an absorbance measurement for each calibration sample in a primary calibration set, said calibration samples having known reference values for total Hb, oxy-Hb, metHb and total Hb-metHb;
   b) calculating an order derivative of absorbance for each of said calibration samples; and
   c) creating a primary calibration algorithm for each of said indicator of hemolysis and said met-Hb using said derivatives of absorbance, said known reference values, and a statistical technique.

3. The method of claim 2, wherein in said step of collecting (step a)), said reference values for either said total Hb or said oxy-Hb, are obtained from the measured amounts of said total Hb or said oxy-Hb, in the presence of one or more of oxy-Hb, deoxy-Hb, carboxy-Hb and met-Hb in said calibration samples.

4. The method of claim 3, wherein said oxy-Hb accounts for about 95% of total Hb in said sample, or wherein said total-Hb in said sample comprises about 95% oxy-Hb.

5. The method of claim 2, wherein in said step of creating (step c)), said statistical technique is selected from the group consisting of simple linear regression, multiple linear regression, partial least squares, and principal component analysis.

6. The method of claim 1, wherein said sample is one of serum, plasma, urine, synovial fluid or cerebrospinal fluid.

7. A method for flagging a predicted value for an indicator of hemolysis in a sample, in the presence of methemoglobin (metHb), said method comprising the steps of:
   i) developing a first primary calibration algorithm for one of a total hemoglobin (Hb), an oxy-hemoglobin (oxy-Hb), or a total hemoglobin methemoglobin (Hb-metHb), for predicting a value for one of said total Hb, said oxy-Hb, or said total Hb-metHb, in said sample, wherein said total Hb, said oxy-Hb, or said total Hb-metHb serves as an indicator of hemolysis in said sample;
   ii) deriving a second primary calibration algorithm for said met-Hb, for predicting a second value for said met-Hb in said sample;
   iii) determining if said predicted met-Hb value exceeds a pre-determined value; and
   iv) flagging said predicted value for said total Hb, said oxy-Hb or said total Hb-metHb, when said predicted met-Hb value exceeds said pre-determined value.

8. The method of claim 7, wherein said step of developing (step i)) and said step of deriving (step ii)), each comprises the steps of:
   a) collecting an absorbance measurement for each calibration sample in a primary calibration set, said calibration samples having known reference values for total Hb, oxy-Hb, metHb and total Hb-metHb,
   b) calculating an order derivative of absorbance for each of said calibration samples; and
   c) creating a primary calibration algorithm for each of said indicator of hemolysis and said met-Hb using said derivatives of absorbance, said known reference values, and a statistical technique.

9. The method of claim 8, wherein in said step of collecting (step a)), said reference values for each of said total Hb or said oxy-Hb are obtained from the measured amounts of said total Hb or said oxy-Hb, in the presence of one or more of oxy-Hb, deoxy-Hb, carboxy-Hb and met-Hb in said calibration samples.

10. The method of claim 9 wherein said oxy-Hb accounts for about 95% of total Hb in said sample, or wherein said total-Hb in said sample comprises about 95% oxy-Hb.

11. The method of claim 8, wherein in said step of creating (step c)), said statistical technique is selected from the group consisting of simple linear regression, multiple linear regression, partial least squares, and principal component analysis.

12. The method of claim 7, wherein said sample is one of serum, plasma, urine, synovial fluid or cerebrospinal fluid.

* * * * *